United States Patent
Marschall et al.

(10) Patent No.: US 12,276,665 B2
(45) Date of Patent: Apr. 15, 2025

(54) METHODS FOR SCREENING AND IDENTIFYING AGENTS THAT INHIBIT OR MODULATE THE NUCLEAR EGRESS COMPLEX OF HERPESVIRUSES

(71) Applicants: AICURIS GMBH & CO. KG, Wuppertal (DE); FRIEDRICH-ALEXANDER-UNIVERSITAT ERLANGEN-NURNBERG, Erlangen (DE)

(72) Inventors: Manfred Marschall, Nuremberg (DE); Yves Muller, Erlangen (DE); Heinrich Sticht, Furth (DE); Jutta Eichler, Erlangen (DE)

(73) Assignee: AICURIS ANTI-INFECTIVE CURES AG, Wuppertal (DE)

(*) Notice: Subject to any disclaimer, the term of this patent is extended or adjusted under 35 U.S.C. 154(b) by 1036 days.

(21) Appl. No.: 17/261,501

(22) PCT Filed: Jul. 19, 2019

(86) PCT No.: PCT/EP2019/069562
§ 371 (c)(1),
(2) Date: Jan. 19, 2021

(87) PCT Pub. No.: WO2020/016433
PCT Pub. Date: Jan. 23, 2020

(65) Prior Publication Data
US 2021/0396761 A1 Dec. 23, 2021

(30) Foreign Application Priority Data
Jul. 20, 2018 (EP) .................................... 18184806

(51) Int. Cl.
*G01N 33/68* (2006.01)
*C07K 14/04* (2006.01)
*C07K 14/05* (2006.01)

(52) U.S. Cl.
CPC ......... *G01N 33/6803* (2013.01); *C07K 14/04* (2013.01); *C07K 14/05* (2013.01); *G01N 2333/04* (2013.01); *G01N 2333/05* (2013.01)

(58) Field of Classification Search
None
See application file for complete search history.

(56) References Cited

U.S. PATENT DOCUMENTS

| | | | |
|---|---|---|---|
| 6,818,418 B1 | 11/2004 | Lipovsek et al. | |
| 8,501,194 B2* | 8/2013 | Spector | A61P 31/22 424/230.1 |
| 9,346,874 B2* | 5/2016 | Grawunder | A61P 31/18 |
| 10,842,863 B2 | 11/2020 | Thirion et al. | |
| 11,058,765 B2* | 7/2021 | Stergiou | A61P 31/22 |
| 2005/0255548 A1 | 11/2005 | Lipovsek et al. | |
| 2015/0051090 A1* | 2/2015 | Shan | G16B 35/00 506/8 |
| 2015/0284458 A1* | 10/2015 | Chen | C07K 16/00 435/252.31 |
| 2015/0307850 A1 | 10/2015 | Fu et al. | |
| 2017/0096480 A1* | 4/2017 | Chen | C07K 16/24 |
| 2019/0202902 A1* | 7/2019 | Chen | A61P 5/14 |
| 2024/0050518 A1* | 2/2024 | Nabel | A61K 38/162 |

FOREIGN PATENT DOCUMENTS

| | | | | |
|---|---|---|---|---|
| WO | WO-0164942 A1 * | 9/2001 | | C07K 14/78 |
| WO | 2011138040 A2 | 11/2011 | | |
| WO | 2014089158 A1 | 6/2014 | | |

OTHER PUBLICATIONS

Norberg, P. et al. (2015). Recombination of Globally Circulating Varicella-Zoster Virus. Journal of virology, 89(14), 7133-7146. (Year: 2015).*
GenBank Accession No. CEQ35959.1, Direct Submission, N.E. Grayson, submitted Feb. 26, 2015 (Year: 2015).*
GenBank Accession No. AWG87739.1, Direct Submission, Palser et al., submitted Oct. 26, 2017 (Year: 2017).*
GenBank Accession No. ABH08462.1, Direct Submission, V.N. Loparev, submitted Jun. 5, 2006 (Year: 2006).*
GenBank Accession No. AKG58208.1, Direct Submission, D.P. Depledge, submitted Feb. 9, 2015 (Year: 2015).*
Schnee, M., Ruzsics, Z., Bubeck, A., & Koszinowski, U. H. (2006). Common and Specific Properties of Herpesvirus UL34/UL31 Protein Family Members Revealed by Protein ComplementationAssay. Journal of Virology, 80(23), 11658-11666. (Year: 2006).*

(Continued)

*Primary Examiner* — Janet L Andres
*Assistant Examiner* — Carey Alexander Stuart
(74) *Attorney, Agent, or Firm* — MILLEN, WHITE, ZELANO & BRANIGAN, P.C.; Ryan R. Pool

(57) ABSTRACT

The present invention generally provides for a novel NEC-targeted strategy for the development of antiherpesviral drugs as well as for a novel antiviral strategy targeting the viral-cellular nuclear egress complex (NEC) for a small molecule-based therapy or prophylaxis to control infections with human cytomegalovirus or other pathogenic viruses of the group of the Herpesviridae. Methods for screening agents/compounds/small molecules modulating/inhibiting the nuclear egress complex of Herpesviridae are provided as well. Specifically novel drug targets of the viral nuclear egress complex of viruses of the Herpesviridae are provided.

21 Claims, 28 Drawing Sheets

Specification includes a Sequence Listing.

(56) References Cited

OTHER PUBLICATIONS

International Search Report for PCT/EP2019/069562 dated Sep. 25, 2019.
Kendra E. Leigh et al. "Structure of a herpesvirus nuclear egress complex subunit reveals an interaction groove that is essential for viral replication," Proceedings of the National Academy of Sciences of the United States of America, vol. 112, No. 29, Jul. 6, 2015, pp. 9010-9015, XP055231618.
Janna M. Bigalke et al., "The Great (Nuclear) Escape: New Insights into the Role of the Nuclear Egress Complex of Herpesviruses" Journal of Virology, vol. 89, No. 18, Jun. 24, 2015, pp. 9150-9153, XP05522872.
Michaela Gebauer: "Engineered protein scaffolds as next-generation antibody therapeutics", Current Opinion in Chemical Biology 2009, 13:245-255.
Jens Milbradt: "Proteomic Analysis of the Multimeric Nuclear Egress Complex of Human Cytomegalovirus", Molecular & Cellular Proteomics 13.8 (2014) 2132-2146.
Mirjam Steingruber; "Cyclins B1, T1, and H differ in their molecular mode of interaction with cytomegalovirus protein kinase pUL97", J. Biol. Chem. (2019) 294(15) 6188-6203.
Thierry Wurch: "Novel protein scaffolds as emerging therapeutic proteins: from discovery to clinical proof-of-concept", Trends in Biotechnology Nov. 2012, vol. 30, No. 11 (575-581).

* cited by examiner

Figure 1:
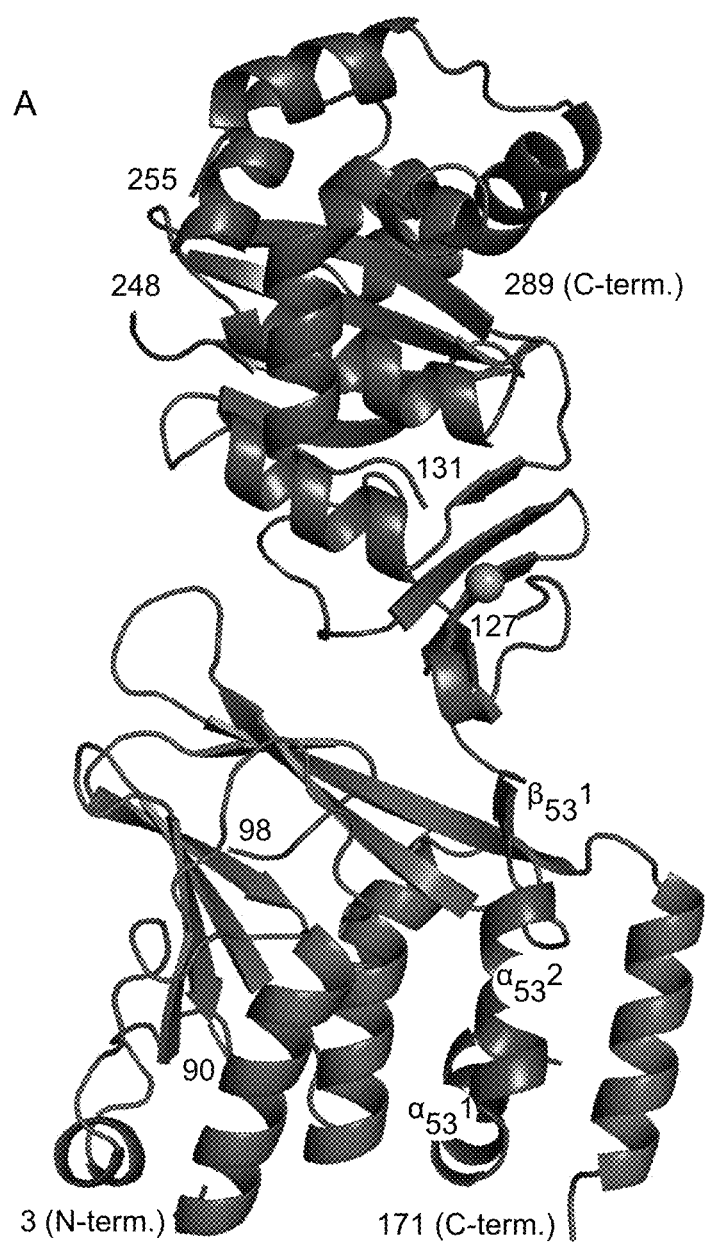
Figure 1:
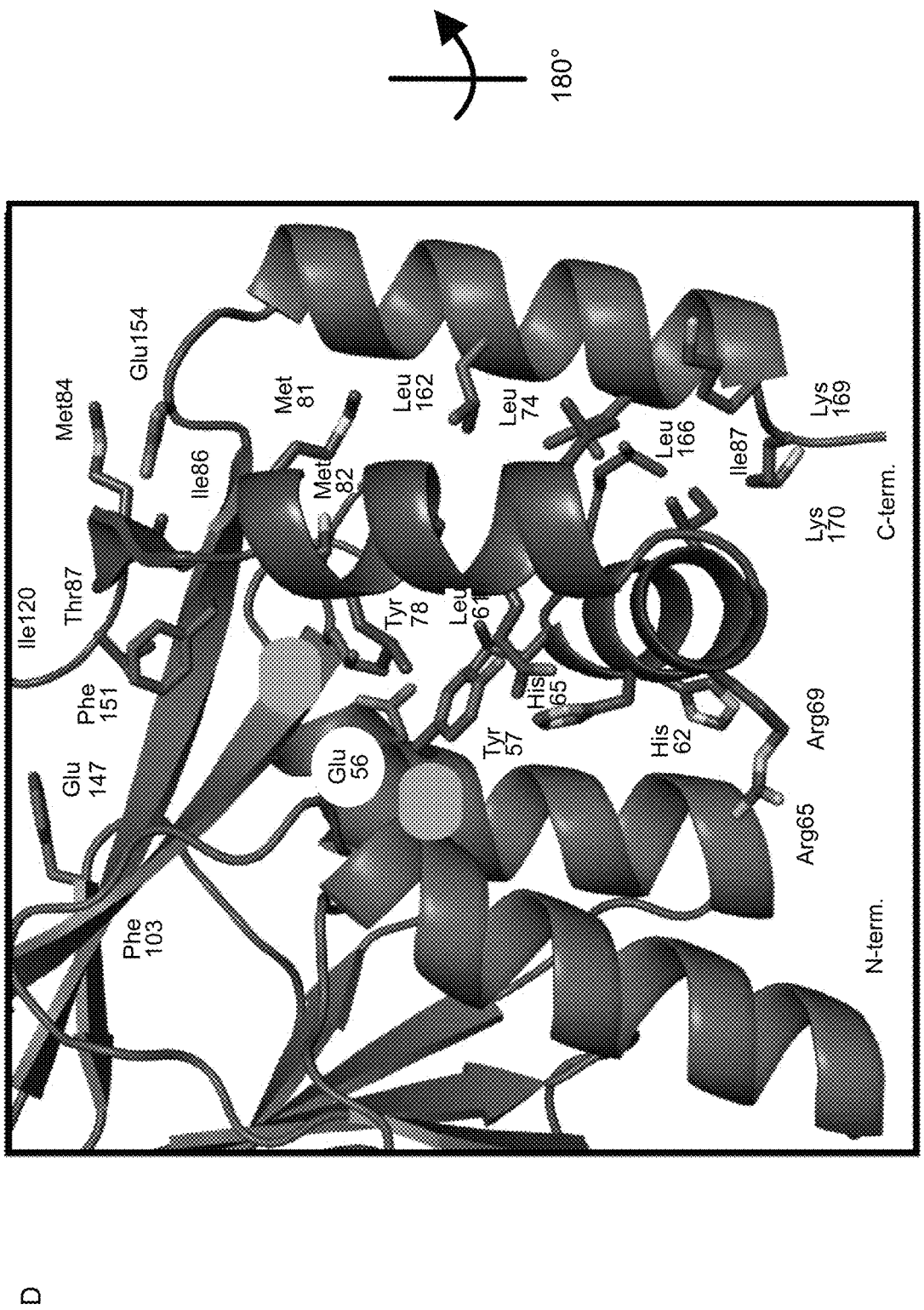
Figure 1:
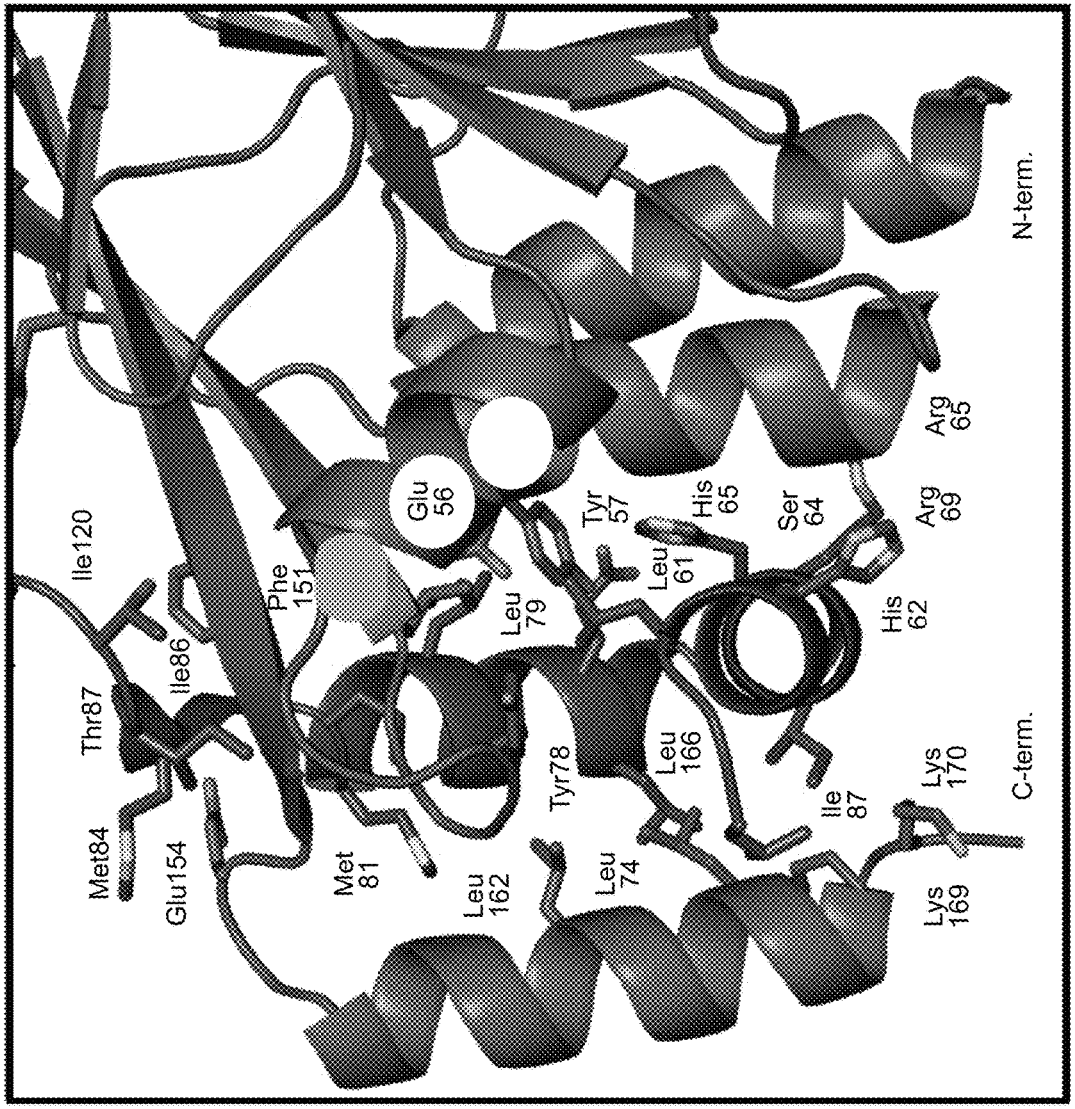

FIG. 1 (continued)
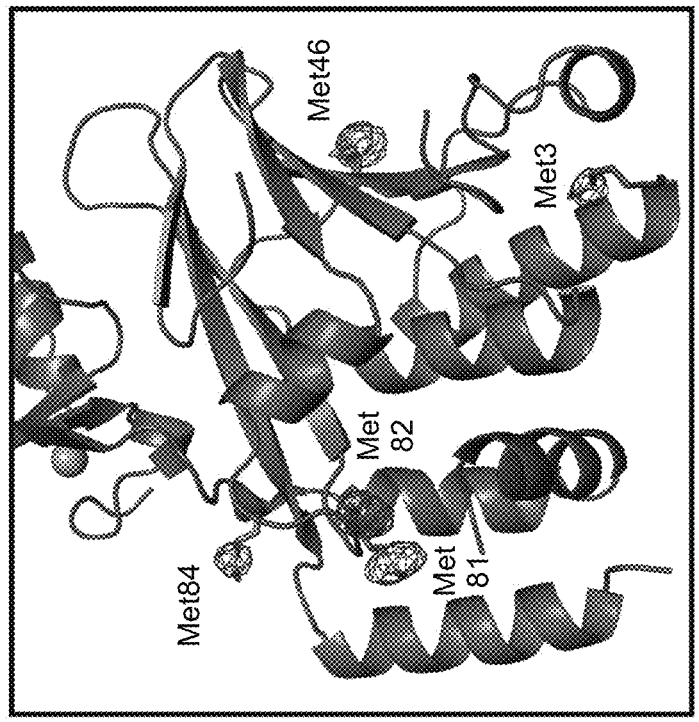
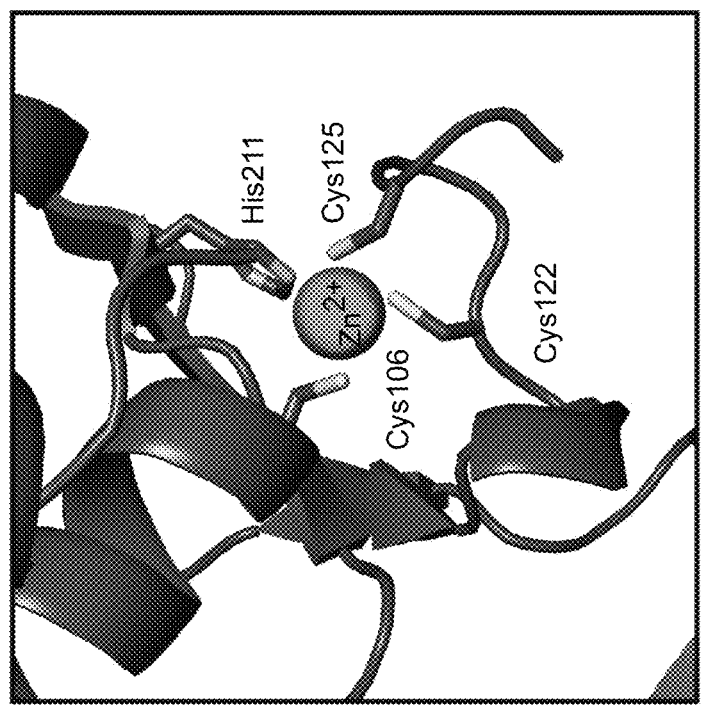

Figure 2:
Figure 2:
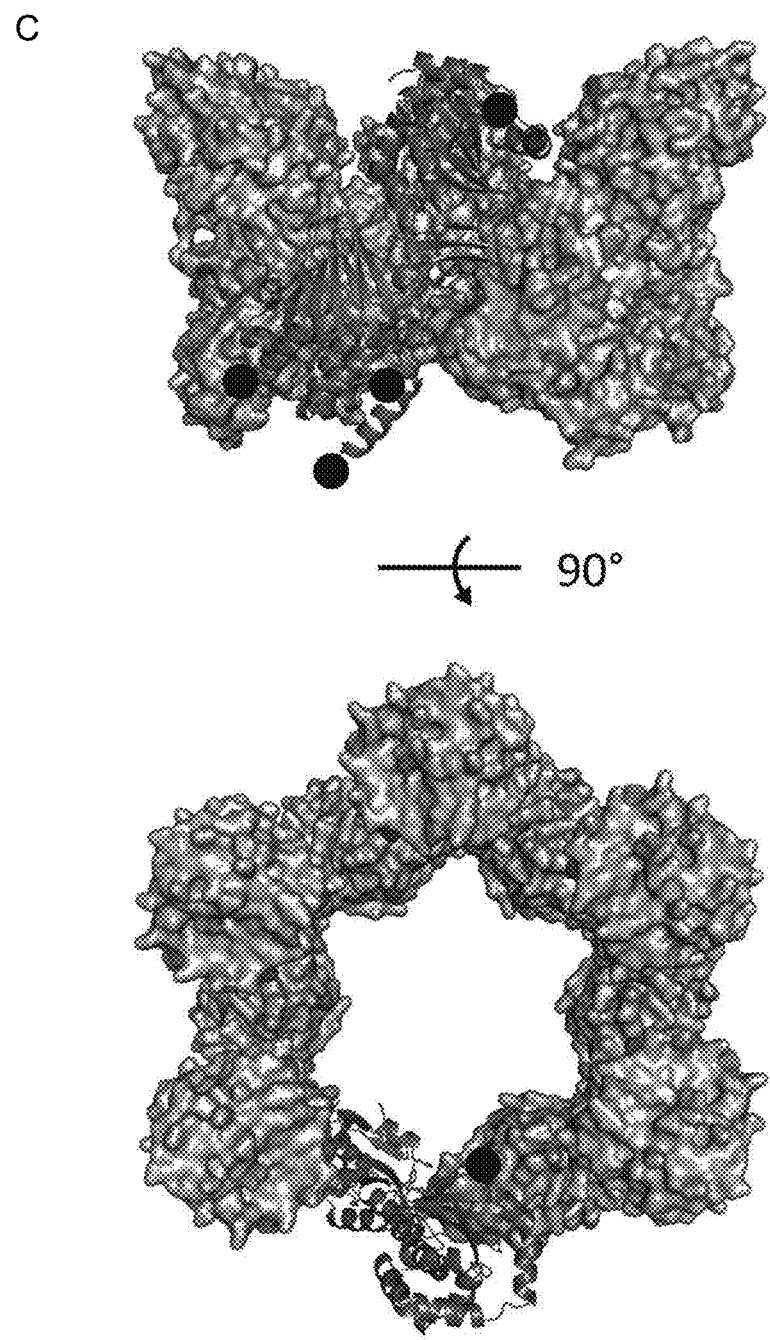

FIG. 2 (continued)
B
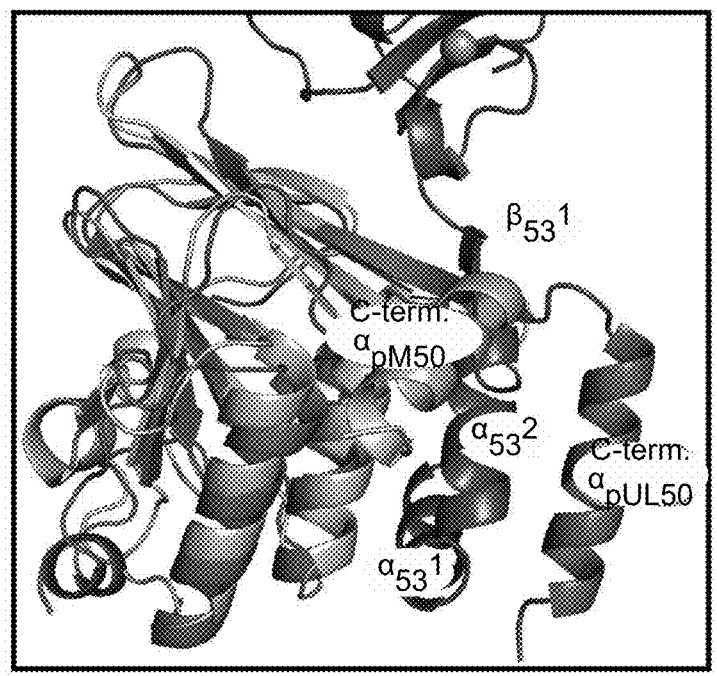
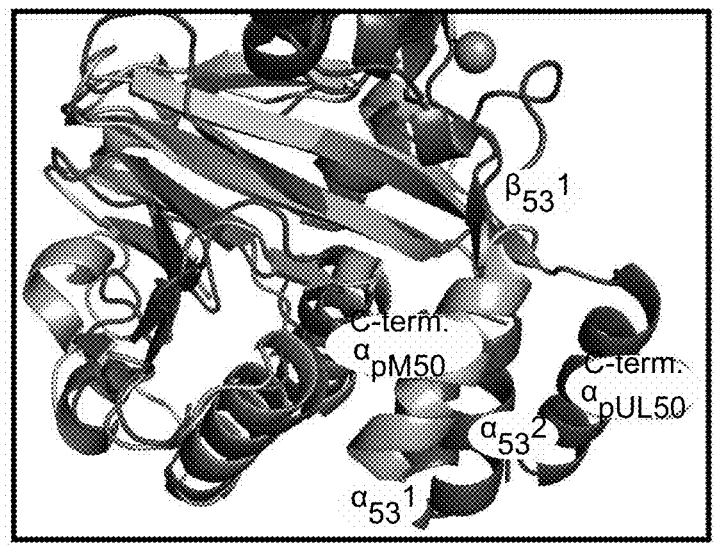

FIG. 4A

Homologues of HCMV pUL53

```
HCMV pUL53   (1)  ------------------------------MSSVSGVRTPRERRSALRSLLRKRRQRELASKVASTVNG
HSV-1 UL31   (1)  -------------------------------MYDTDPHRPGSREGPYHGKERRRSPSSAAGGTLGVVRRA
HSV-2 UL31   (1)  -------------------------------MYDIAPRRSGSREGPGRDKTRRRSPFSAAGNP-GVERRA
VZV orf27    (1)  MHLKPTPFFHANQPPMPHSYEMEDLCFDDMQYRWSPSNTFYRSMSRRYFSVSRSG-FSMR
HHV-6A U37   (1)  --------------------------------------MTVHKSRIRRSPSLSVTHRIQ-----
HHV-6B U37   (1)  --------------------------------------MTVHKNPFRRSPSLSVTHRIQ-----
HHV-7 U37    (1)  ----------------------------------------MAIQSTRRLRPASSLLRK------
EBV BFLF2    (1)  -----------------MAFVTPDAVNARQQRPADPALRRLMHPHRPNYTASKASAHSVK
HHV-8 ORF69  (1)  -------------------------MPKSVSSHISLATSTGRSGPRDIRRCLSSRLPSVPPG
PrV UL31     (1)  ------------------------------------MFERRRLLRPK-------
MCMV pM53    (1)  ------------MFRSPEGEERDAALPEEEEGGEAPRPSRMMMSPRPVFRAPHRPAGSGLPTFLRS HCMV pUL53  (40)  A----------------------------------TSANNHGEPPSPADARPPLTLHD
HSV-1 UL31  (40)  S----------------------------------PKSLPPHARKQELCLHEPQRYRG
HSV-2 UL31  (39)  S----------------------------------PKSLPSHARPLELCLHEPRRYRG
VZV orf27   (60)  VR---------------------------------SPTPCRRQTIRGKLMSREPSVYRH
HHV-6A U37  (22)  -----------------------------------KRPDHPEKTKLYLQLK HD
HHV-6B U37  (22)  -----------------------------------KRPDHREKTKLYLQLK HD
HHV-7 U37   (19)  -----------------------------------SKPYNKEKTNLSLSLS KE
EBV BFLF2   (44)  SVSRCGKS-----RSE-----------LGRMERVGSVARSICSRHTRHGVDRSHFS RD
HHV-8 ORF69 (38)  -----------------------------------ARSASVSSKHRNGLRKFISDKV
PrV UL31    (12)  -----------------------------------SSAARPKTLTPAAPDRYAF
MCMV pM53   (55)  PSACRCSSPSPEPQWQQRRRAEKPSTTPTDPPPPPKRSAASAAAGAAAPESEYLNVK SE HCMV pUL53  (64)  LHDIFREHPELRLRYDNMMMMAITQKRSICLPKNFHSRQHTCDISKYGNEQVSRIA T
HSV-1 UL31  (64)  FAALAQT SE IAIVRSLSVPLVKTTPVSLP CLDQTVADK TLS MGYYLGIGGC P
HSV-2 UL31  (63)  FFAALAQT SE IAIVRSLSVPLVKTTPVSLP SLDQTVADK TLS MGYYLGIGGC P
VZV orf27   (86)  YFNYIAPS PE LATVRGLIVP IKTTPVTL NLGQTVADK SLS MGYHLGLGGY P
HHV-6A U37  (41)   TV NLF EY QSF AII LP KP DV SLSN HQ T EES AN EQISKS CL
HHV-6B U37  (41)   AV NLF EY QSF AII LP KP DV SLSN HQ T EES AN EQISKS CL
HHV-7 U37   (38)   SV KLF EY RF NMM LP KP KIP DLSL HQ T DL AN EQVSKS CV
EBV BFLF2   (87)  FFRGISARFELGKDF REMNTP HVS AVFL LSLCTLSPGR RL FGHSLTLCSH E
HHV-8 ORF69 (60)  FFSILSHRHELGVDF REMETP CTSKTVML DLSTVAPGR VSL FGHSSNMGFQ A
PrV UL31    (31)  YFAYAAAQ SD VTTVRGLSNPLIKTAPVEL DLGQAVADK SLS MGYYLGLGGC P
MCMV pM53  (115)   DV QRH DL Q Y KIM LP KS PL DFF S FQ T DL GN EQVSRS T HCMV pUL53 (124)  S EDNRI-L ASDAN-----------------YAFIN QTSN IMKN NFYY C----
HSV-1 UL31 (124)  A NAGDG-RFAAISREA---------------LIL FVQ INTIFEH AFLASLVVLAD
HSV-2 UL31 (123)  A SAGDG-RLATVSREA---------------LIL FVQ INTIFEH TPLASLVVLAD
VZV orf27  (146)  T TASGEPRLCRI RAA---------------LIL YVQ LN IYEY VFLASILALSD
HHV-6A U37 (101)  H ESVS--V S AA------------------ HL QVN IN QR LYFG R----
HHV-6B U37 (101)  H ESVS--V S AA------------------ HL QVT IN QR FYFG R----
HHV-7 U37   (98)  N GTTN--I S AA------------------ YM QIS V QR LYYG Q----
EBV BFLF2  (147)  I TNRSQ-VHVPQEFS---------------STQLSFF NVHK IPKKTFYVSLLS---
HHV-8 ORF69 (120) L PSTEN-PTVAQGSPPQTMVGDALKKNNELCSVAL FYH ADKVIQHKTFYLSLLS---
PrV UL31    (91)  T AAAEP-RLGR RAA----------------LVL YVQ LNS IYEY VFLASVAAR-
MCMV pM53  (175)  T KETTR-L A A------------------- FI T SN KH FYF R----
```

FIG. 4A (continued)

```
HCMV pUL53   (160)  -------KSSELKLSTNQPPIFQIYTLLHAANHDIVEFMHAE----DGRLRMHVIFENP
HSV-1 UL31   (167)  RH---NAPLQDELAGILGQPELFFVHTILRGGGACDPRLLFYPD-PTYGGHMLYVIFPGT
HSV-2 UL31   (166)  RH---STPLQDELADTLGQPELFFVHTILRGGGACDPRFLFYPD-PTYGGHMLYVIFPGT
VZV orf27    (190)  RANMQAASAEPELSSVLAQPELFPMYHIMREGGMRDIRVLFYPDG-DAGGFMYYVIFPGK
HHV-6A U37   (136)  -------KDMEIRMSARQPTIEEFFIVHNTINRIFRIMFER----KQKLGREIVFQSR
HHV-6B U37   (136)  -------KDMEIRMSARQPTIEEFFIVHNTINRIFRIMFER----KQKLGREIVFQSR
HHV-7 U37    (133)  -------KVEIRMSARQPTLEEFFILSSIASNFLRIMFEN----NEKLNEYVVFQTR
EBV BFLF2    (187)  -------SSPSAVKAGLSQPSLLYAYLVTGHFCGTICFIFSTNG---KGRLIEHLLLQGT
HHV-8 ORF69  (176)  -------HSMDVVRQSFIQPGLLYANLVLKTFGHDPLFIFTTN----NGMLTECILEKTR
PrV UL31     (132)  -------DPSERALEEVLAHPELFFAYEVLRDGGLRDVRVLFFEDPDAQCALMYYVIFPER
MCMV pM53    (211)  -------KNMELRMAANPQLEEFYEIVQSCVQETVELIYYD----REMAHEQLIFEKE HCMV pUL53   (209)  DVHEPCDEITQMLTAAREDYSVTINIVRDHVVISVLQHAVSA---SSVEIDVTILQRRID
HSV-1 UL31   (223)  SAMLHYRLEDRMLTAC-PGMRFVAHVWQSTFVLVVRRNAEKPTDAEIPTVSAADIYCRMP
HSV-2 UL31   (222)  SAMLHYRLEDRMLTAC-PGMRFAAHVWQSTFVLVVRRNAEKPADAEIPTVSAADIYCRMP
VZV orf27    (249)  SVMLHYPLEDHIQAAC-PGMRIVAHVWQTFFLLSVCRNPEQQTETVVPSEGTSDVYCRMC
HHV-6A U37   (185)  TLMECERFRIVAVS-SGMNEYEDELQESVILTVLRETLDTN--TNIHEIGMEQRKLE
HHV-6B U37   (185)  TLMECERFRIIAVS-SGMNEYEDELQDSVILTVLRETLDTN--TNIHEIGMEQRKLE
HHV-7 U37    (182)  TLMECERLEIMTVS-SGMTVLEDELHDSIVLHVLEKTIET----SNIQEINVEPKIE
EBV BFLF2    (237)  SLMEETELKLLCENIGPTMELAVDLVGDAFCIKVSPRDTVYE--EAVNVEEDAIYEAIK
HHV-8 ORF69  (225)  ALMLGETALRLLMDNL-PNMKISADCCRQSYVVKFVPTHPDT----ASIAVQVHTICEAVA
PrV UL31     (186)  SVMEVHHRVLDRLLGAC-AGHRIVAHVWQTMFVLVVRKEGDGRPADDVPAVSASDIYCRMP
MCMV pM53    (260)  TVMERSQEERILTVAKDAMGESEEAHQRITLTARELRLES---SSLPEIVLMERKVD HCMV pUL53   (268)  EMDIPNQVSESFERYKELIQELCQSSGNNLYEEATSSYAIPSPLTASPLHVVSTNGCGPS
HSV-1 UL31   (282)  DISFDGGLMLEYQRLYATFDEFPPP------------------------
HSV-2 UL31   (281)  DISFDGGLMLEYQRLYATFDEFPPP------------------------
VZV orf27    (308)  DLNFDGELLLEYKRLYALFDDFVPPR------------------------
HHV-6A U37   (242)  EMDIENEISDRLEKYKGHLIGFH------------------------
HHV-6B U37   (242)  EMDIENEISDRLEKYKGHLIGFH------------------------
HHV-7 U37    (238)  EMDVEDEIGDKFEKLKHILPFI------------------------
EBV BFLF2    (295)  DLECGDELRLQIINYTQLILENKQ------------------------
HHV-8 ORF69  (281)  ALDCTDEMRDDIQKGTALVNAL------------------------
PrV UL31     (245)  DISFDGELLLEYKRLYAAFEDFRPPRP------------------------
MCMV pM53    (317)  ELEIENETMEKFESYSL------------------------

HCMV pUL53   (326)  SSSQSTPPHLHPPSQATQPHHYSHHQSQSQQHHHRPQSPPPLFLNSIRAP
HSV-1 UL31   (307)  ------------------------
HSV-2 UL31   (306)  ------------------------
VZV orf27    (334)  ------------------------
HHV-6A U37   (265)  ------------------------
HHV-6B U37   (265)  ------------------------
HHV-7 U37    (260)  ------------------------
EBV BFLF2    (319)  ------------------------
HHV-8 ORF69  (303)  ------------------------
PrV UL31     (272)  ------------------------
MCMV pM53    (334)  ------------------------
```

FIG. 4 B

Homologues of HCMV pUL50

```
HCMV pUL50  (1)   --------MEMNKVLHQDLVQATRRILKLG----PSELRVTD-AG-LICRNPNYSVCAML
HSV-1 UL34  (1)   MAGLGKPYTGHPGDAFEGLVQRIRLIVPST------LGGDGEAGPYSPSSLPSRCAFQF
HSV-2 UL34  (1)   MAGMGKPYGGRPGDAFEGLVQRIRLIVPAT------LGGGGESGPYSPSNFPSRCAFQF
VZV orf24   (1)   MSPRTYVRSEPRRGCGDNLLQRIRLVVPSA------LQCCDGDLPIFDPQRFPARCVFQF
HHV-6A U34  (1)   ------MANVLKEKMYDELLSACSIKMG----SHDYRITE-RN-ILSRKFPLCIIR
HHV-6B U34  (1)   ------MANVLKEKMYDELLSACSIKMG----SHDYRMTE-RN-ILSRKFPLCIIR
HHV-7 U34   (1)   ---------MLKEKMYDEIILSCSVKMG----PADFRVTD-RN-IFSRKFPLCITL
EBV BFRF1   (1)   -------MASPEEPLLDELRNVIVSPFCDSG-SLEVERCSG-AR-VFSRGSSQPLCTVK
HHV-8 ORF67 (1)   -------MSVVGKRVVDELCRVVSSYYGQSGQSLDLERCIDGAP-VYARGGATAICTVPM
PrV UL34    (1)   --------MSGTLVQRLKLISGG-----NLRCSDGET-ACDFERFPTRCVFQV
MCMV pM50   (1)   --------MEIDKNVGADIISNMRKTFRD-ENELRITD-TA-RICKNYSLCAML
```

```
HCMV pUL50  (48)  K----TDTVYCVEFLLSYNESRTD-----HVPCRIRMNGGCAVSLCCFVRAFVKLVSPAR
HSV-1 UL34  (55)  HGRDGSLESFPIEKVFRLMNDWAEVP---CNPYLRIQTGVSLFQGFFHPRNAPG-GA
HSV-2 UL34  (55)  HGQDGSLEAFPIEKVFRLMNDWADVP---CNPYLRVQTGVSLFQGFFNPRHGAPG-GA
VZV orf24   (55)  NGEDNVSEAFPVEKIMRLMANWAQVD---CDPYIRIQTGVSLFQGFFPFTNAPV-AE
HHV-6A U34  (50)  K----LDYANLRKIILSLEHVTK-----QEPRKVSTGGASMSYLHAEVYVEG-HR
HHV-6B U34  (50)  K----LDYANLRKIILSLEHVTK-----QEPRKVSTGGAKMSYLHAEVYAEG-HR
HHV-7 U34   (47)  K----LDFASLKKIILSLEDLTK-----QEARIITGCAKMSYLHAEIKQES-QN
EBV BFRF1   (51)  R----HGQIYHLEFVYKFLAFKLKNCNYPSSPVVVISNMGLATTLPFLHERSGLRSGQS
HHV-8 ORF67 (53)  Q----RGCVHLEFVYKFHARHLEEMHYPFSPCKVISNMGLSTTLKFLCPRSDAVSQFG
PrV UL34    (41)  HGQDSSNDTFPLEKVFRLMRSWAHVP---CDPYVRVQTGVSLFQGFFPRRADAPL-AA
MCMV pM50   (48)  T----TDIVRPVEKILSYVMCRSG-----RTACKVSMGCRSLSYIGFPEPLKD-LR
```

```
HCMV pUL50  (99)  HVGSE-FNV-LKYNESLIYTLKDIEEIK---------PSAYGVLTKCVVRKSNSASVFNIRL
HSV-1 UL34  (111) ITPERTNVIHSTETTGLSLGLLDTIKSPLGLDARMMASMNISFVRMPRVQLAFPFMG
HSV-2 UL34  (111) ITAEQTNVIHSTETTGLSLGLLDDVKGRLGLDARMMASMNISFVRMPRVQLAFPFMG
VZV orf24   (111) VSIDSMNVISSTLSTGINLSALESIKRGGGIDRPLQALMWNKFVRMPYVQLSFPFMG
HHV-6A U34  (100) AVRE-CN-ILRKKECLTTRMSKVAMK---------STFAFFKIIPR-RDDTYVVRF
HHV-6B U34  (100) AVRE-CN-ILRKKECLTTRMSKVAMK---------STFAFFKIIPR-RDETYVVRF
HHV-7 U34   (97)  IVKE-CN-ILNKECLSKCLNKEAIK---------SSSGILKKIIPR-RDAAFIVRF
EBV BFRF1   (107) GPCLGLSTDVDLPKNSIIMLGQDDFIKFKSPLVFPAELDLLKSMVQKAYITEHRTTMQF
HHV-8 ORF67 (109) --HVLPVESDVYLAKNTSKVLGQDDFTKFKASLVFSKNLGVYNSMVICRTYFTDYRQVLQF
PrV UL34    (97)  ITAEHMNVIASTHSTGMSLSALDDIKRAGGVDTPLRAMMSVSFVRMPRVQLSFPFMG
MCMV pM50   (96)  RVCD-FNF-LSKMEAIVRTLARERIK---------RCDKGKLRNKVVRKSSGMSYDIRV
```

```
HCMV pUL50  (149) IAFGPENGGEYENLLRELYAKKAASTSLAVRNHVTVSSHSGSGPSLWRARMSAALTRTAG
HSV-1 UL34  (171) PEDAGRTKPILCRAAEQAITRRR----------------------R-TPRSR
HSV-2 UL34  (171) PEDAVRTKRILCRAAEQALARRRR----------------------SRRSQ
VZV orf24   (171) PEDPSPTIFLMARATDAYMYKET----------------------GRNL
HHV-6A U34  (149) VRFGPENSERISLKAIFLKKCSMGKQHLE----------------SNRFCQGLR
HHV-6B U34  (149) VRFGPENSERISLKAIFLKKCSMGKQHLE----------------SNRFCQGLR
HHV-7 U34   (146) VRFGESESEKIALRKAIILKKKFLER----------------QDLE
EBV BFRF1   (167) LVRQAANAQKASRVMDMISDMSQQLSR----------------SGVE
HHV-8 ORF67 (168) LVVTFSHFRLKSRETVYCLAAPVAD----------------
PrV UL34    (157) PDDASQTQPLLDRAEMRQRSVSR----------------PGG---
MCMV pM50   (148) VRFGDNRAKQARRDIYARRMTS----------------VPTDCGSLI
```

FIG.4B(continued)

```
HCMV pUL50  (209) KRSSRTASPPFPPRHPSCSPTMVAAGGAAAGPRPPPPPMAAGSWRLCRCEACMGRCGCAS
HSV-1 UL34  (200) EAYGAEAGLGVAGTG---------------------------------------------
HSV-2 UL34  (200) DDYGAVVVAAAHHS----------------------------------------------
VZV orf24   (198) DEYIRWRPSFRSPP----------------------------------------------
HHV-6A U34  (189) RRSSHVLEKGRFES----------------------------------------------
HHV-6B U34  (189) RRSSHVLEKGQLGS----------------------------------------------
HHV-7 U34   (177) KHKAARHIKKPLPL----------------------------------------------
EBV BFRF1   (199) DTGAPVIGGGGPRP-------------------------GVIHSGCLGDSHVR-----G
HHV-8 ORF67 (195) --SAAQGGAGFPTN----------------------------------------------
PrV UL34    (183) GAGGGDDGEGPSPR----------------------------------------------
MCMV pM50   (182) CRKAPCLAAAPPRR------------------PPPPPPPGQRWGSLRKHGPVLTRRYAG HCMV pUL50  (269) EGDADEEEEELLALAGEGKAAAAAAGQDVGGSARRPLEEHVSRRRGVSTHHRHPPSPPCA
HSV-1 UL34  (215) ------------------FRARGDSFGPLPLLTQGPSR----------------------
HSV-2 UL34  (214) ------------------SGAPGPGVAASGPPAPPGRG----------------------
VZV orf24   (212) ------------------ENGSPNTSVQMQSDIKPA------------------------
HHV-6A U34  (203) -------SGK------VVNKASAVVTSQESIKQFYEK-----------------EK---
HHV-6B U34  (203) -------SGE------IAMKASAVVTSQESINQFYEK-----------------EK---
HHV-7 U34   (191) ----------------QLKSVGEMTSFRSINYMGNT------------------KD---
EBV BFRF1   (228) RGG---WDLDNFSEAETEDEASYAPWPDKDSWSESE------------------AAPWK
HHV-8 ORF67 (207) ----------------GRDAPACTSDVTAVYWAGQG------------------------
PrV UL34    (197) --------------APIRPTVISPVPGHAAAAFVGQAAYP--------------------
MCMV pM50   (223) GGGAAKNQPAAASPTSTSTSSPAAPSRDQDQTQRPP--------------PAGDTN HCMV pUL50  (329) PSLEPTGYRWAPSSWWRAPSGPSRPQSGPWLPAREATLGPLVLALLLVLALLWRGHGQSS
HSV-1 UL34  (235) ---------PWHQALRGLEHLPIG-----------PPALVLAAGLVLGAAIWWVVGAGARL-
HSV-2 UL34  (234) ---PARPWHQAVQLFPAPRPG-----------PPALLLLAAGLFLGAAIWWAVGARL---
VZV orf24   (230) ------LPDTQTTRVWKLALPVAN--------VTYALFIVIVLVVVLGAVLFWK------
HHV-6A U34  (229) ---------SLLSGVKFWRLSER---------HCRFALVGICFLLALYFCYVLKKTPTPA
HHV-6B U34  (229) ---------SFLSGVKFSRLSER---------HCRVAIVSICFLLALYFCYVLKKTPTPA
HHV-7 U34   (213) ---------AAVFPVTVPIFARPKN---------ILCGFLVAALLIVCYVIFKEFALSA
EBV BFRF1   (266) KELVPHPIRRHKTRETRKMRGSHSPVERVPPETRETVVGGAWRYSWPATPYLARVLAVTA
HHV-8 ORF67 (227) -----------GRTVRILG-----------AFQWSLGRAVALVRPSWPWISAGIAFLC
PrV UL34    (223) ----------PPARFPASLLHTLLG---------LR-PLAGYAVACVTGALAIVIILNMR---
MCMV pM50   (265) VTAAETTTSERTISFLTRHAN-----------AIHCALILAAAIALVLLWLLYWHAARSAG HCMV pUL50  (369) SPTRSAHRD--
HSV-1 UL34  (276) ---------
HSV-2 UL34  (277) ---------
VZV orf24   (270) ---------
HHV-6A U34  (272) SGSVV----
HHV-6B U34  (272) SGPVV----
HHV-7 U34   (254) DFSAV----
EBV BFRF1   (326) VALLLMFLRWT
HHV-8 ORF67 (263) LGLVWNRPS--
PrV UL34    (263) ---------
MCMV pM50   (315) HP-------
```

FIG. 14

```
HCMV      59 .LTLHDL HDIFREHPEL ELKYLNMKM AITG  88
EBV       78 DRSHFSLRDF RGISANFELG KDFLREMNT PIH. 110
Sharehook 59 ..FYLWSM FIAIMRYFEL GMKYLNMMK PMIG  88
```

FIG. 16A
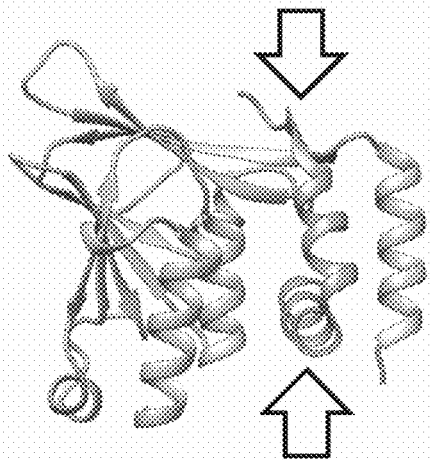 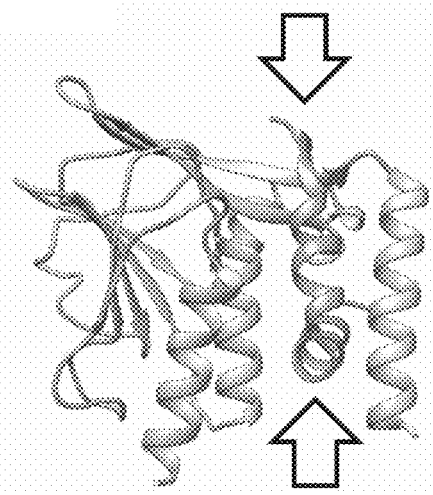
FIG. 16B
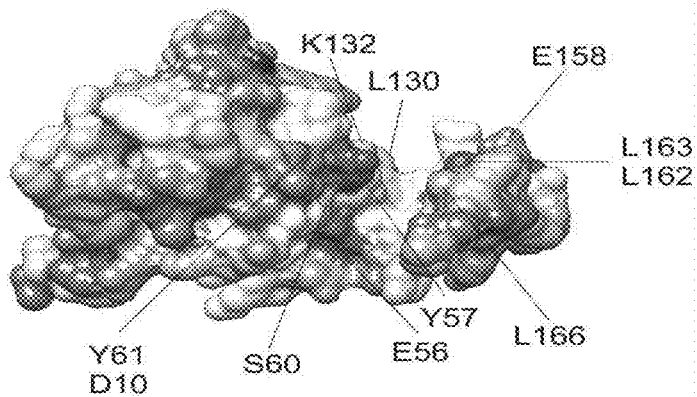
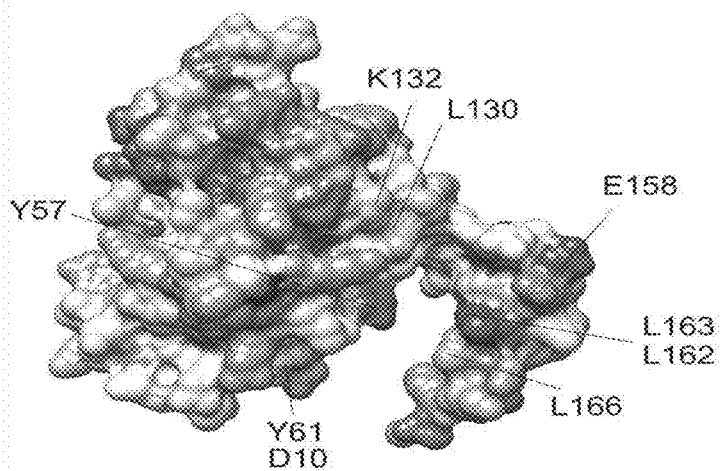

SEQUENCE LISTING

<160> NUMBER OF SEQ ID NOS: 69

<210> SEQ ID NO 1
<211> LENGTH: 413
<212> TYPE: PRT
<213> ORGANISM: Artificial Sequence
<220> FEATURE:
<223> OTHER INFORMATION: Fusion protein of HCMV-NEC proteins pUL50
    protein consisting of pUL50 (1-171) is fused via a GGSGSGGS linker
    to pUL53 (59-292).

<400> SEQUENCE: 1

```
Met Glu Met Asn Lys Val Leu His Gln Asp Leu Val Gln Ala Thr Arg
1               5                   10                  15

Arg Ile Leu Lys Leu Gly Pro Ser Glu Leu Arg Val Thr Asp Ala Gly
            20                  25                  30

Leu Ile Cys Lys Asn Pro Asn Tyr Ser Val Cys Asp Ala Met Leu Lys
        35                  40                  45

Thr Asp Thr Val Tyr Cys Val Glu Tyr Leu Leu Ser Tyr Trp Glu Ser
    50                  55                  60

Arg Thr Asp His Val Pro Cys Phe Ile Phe Lys Asn Thr Gly Cys Ala
65                  70                  75                  80

Val Ser Leu Cys Cys Phe Val Arg Ala Pro Val Lys Leu Val Ser Pro
                85                  90                  95

Ala Arg His Val Gly Glu Phe Asn Val Leu Lys Val Asn Glu Ser Leu
            100                 105                 110

Ile Val Thr Leu Lys Asp Ile Glu Ile Lys Pro Ser Ala Tyr Gly
        115                 120                 125

Val Leu Thr Lys Cys Val Val Arg Lys Ser Asn Ser Ala Ser Val Phe
    130                 135                 140

Asn Ile Glu Leu Ile Ala Phe Gly Pro Glu Asn Glu Gly Tyr Glu
145                 150                 155                 160

Asn Leu Leu Arg Glu Leu Tyr Ala Lys Lys Ala Gly Gly Ser Gly Ser
                165                 170                 175

Gly Gly Ser Leu Thr Leu His Asp Leu His Asp Ile Phe Arg Glu His
            180                 185                 190

Pro Glu Leu Glu Leu Lys Tyr Leu Asn Met Met Lys Met Ala Ile Thr
        195                 200                 205

Gly Lys Glu Ser Ile Cys Leu Pro Phe Asn Phe His Ser His Arg Gln
    210                 215                 220

His Thr Cys Leu Asp Ile Ser Pro Tyr Gly Asn Glu Gln Val Ser Arg
225                 230                 235                 240

Ile Ala Cys Thr Ser Cys Glu Asp Asn Arg Ile Leu Pro Thr Ala Ser
                245                 250                 255

Asp Ala Met Val Ala Phe Ile Asn Gln Thr Ser Asn Ile Met Lys Asn
            260                 265                 270

Arg Asn Phe Tyr Tyr Gly Phe Cys Lys Ser Ser Glu Leu Leu Lys Leu
        275                 280                 285

Ser Thr Asn Gln Pro Pro Ile Phe Gln Ile Tyr Tyr Leu Leu His Ala
    290                 295                 300

Ala Asn His Asp Ile Val Pro Phe Met His Ala Glu Asp Gly Arg Leu
305                 310                 315                 320

His Met His Val Ile Phe Glu Asn Pro Asp Val His Ile Pro Cys Asp
                325                 330                 335

Cys Ile Thr Gln Met Leu Thr Ala Ala Arg Glu Asp Tyr Ser Val Thr
            340                 345                 350
```

```
Leu Asn Ile Val Arg Asp His Val Val Ile Ser Val Leu Cys His Ala
        355                 360                 365

Val Ser Ala Ser Ser Val Lys Ile Asp Val Thr Ile Leu Gln Arg Lys
        370                 375                 380

Ile Asp Glu Met Asp Ile Pro Asn Asp Val Ser Glu Ser Phe Glu Arg
385                 390                 395                 400

Tyr Lys Glu Leu Ile Gln Glu Leu Cys Gln Ser Ser Gly
                405                 410

<210> SEQ ID NO 2
<211> LENGTH: 208
<212> TYPE: PRT
<213> ORGANISM: Artificial Sequence
<220> FEATURE:
<223> OTHER INFORMATION: pUL50 protein consisting of pUL50 (1-171) is
      fused via a GGSGSGGS linker to pUL53 (59-87).

<400> SEQUENCE: 2

Met Glu Met Asn Lys Val Leu His Gln Asp Leu Val Gln Ala Thr Arg
1               5                   10                  15

Arg Ile Leu Lys Leu Gly Pro Ser Glu Leu Arg Val Thr Asp Ala Gly
            20                  25                  30

Leu Ile Cys Lys Asn Pro Asn Tyr Ser Val Cys Asp Ala Met Leu Lys
        35                  40                  45

Thr Asp Thr Val Tyr Cys Val Glu Tyr Leu Leu Ser Tyr Trp Glu Ser
    50                  55                  60

Arg Thr Asp His Val Pro Cys Phe Ile Phe Lys Asn Thr Gly Cys Ala
65                  70                  75                  80

Val Ser Leu Cys Cys Phe Val Arg Ala Pro Val Lys Leu Val Ser Pro
                85                  90                  95

Ala Arg His Val Gly Glu Phe Asn Val Leu Lys Val Asn Glu Ser Leu
            100                 105                 110

Ile Val Thr Leu Lys Asp Ile Glu Glu Ile Lys Pro Ser Ala Tyr Gly
        115                 120                 125

Val Leu Thr Lys Cys Val Val Arg Lys Ser Asn Ser Ala Ser Val Phe
    130                 135                 140

Asn Ile Glu Leu Ile Ala Phe Gly Pro Glu Asn Glu Gly Glu Tyr Glu
145                 150                 155                 160

Asn Leu Leu Arg Glu Leu Tyr Ala Lys Lys Ala Gly Gly Ser Gly Ser
                165                 170                 175

Gly Gly Ser Leu Thr Leu His Asp Leu His Asp Ile Phe Arg Glu His
            180                 185                 190

Pro Glu Leu Glu Leu Lys Tyr Leu Asn Met Met Lys Met Ala Ile Thr
        195                 200                 205

<210> SEQ ID NO 3
<211> LENGTH: 438
<212> TYPE: PRT
<213> ORGANISM: Human herpesvirus 8

<400> SEQUENCE: 3

Met Ala Ser Pro Glu Glu Arg Leu Leu Asp Glu Leu Asn Asn Val Ile
1               5                   10                  15

Val Ser Phe Leu Cys Asp Ser Gly Ser Leu Glu Val Glu Arg Cys Ser
            20                  25                  30

Gly Ala His Val Phe Ser Arg Gly Ser Ser Gln Pro Leu Cys Thr Val
        35                  40                  45
```

Lys Leu Arg His Gly Gln Ile Tyr His Leu Glu Phe Val Tyr Lys Phe
 50                  55                  60

Leu Ala Phe Lys Leu Lys Asn Cys Asn Tyr Pro Ser Ser Pro Val Phe
 65                  70                  75                  80

Val Ile Ser Asn Asn Gly Leu Ala Thr Thr Leu Arg Cys Phe Leu His
                 85                  90                  95

Glu Pro Ser Gly Leu Arg Ser Gly Ser Gly Pro Cys Leu Gly Leu
            100                 105                 110

Ser Thr Asp Val Asp Leu Pro Lys Asn Ser Ile Ile Met Leu Gly Gln
            115                 120                 125

Asp Asp Phe Ile Lys Phe Lys Ser Pro Leu Val Phe Pro Ala Glu Leu
        130                 135                 140

Asp Leu Leu Lys Ser Met Val Val Cys Arg Ala Tyr Ile Thr Glu His
145                 150                 155                 160

Arg Thr Thr Met Gln Phe Leu Val Phe Gln Ala Ala Asn Ala Gln Lys
                165                 170                 175

Ala Ser Arg Val Met Asp Met Ile Ser Asp Met Ser Gln Gln Leu Ser
            180                 185                 190

Gly Gly Ser Gly Ser Asp Arg Ser His Phe Ser Leu Arg Asp Phe Phe
        195                 200                 205

Arg Gly Ile Ser Ala Asn Phe Glu Leu Gly Lys Asp Phe Leu Arg Glu
210                 215                 220

Met Asn Thr Pro Ile His Val Ser Glu Ala Val Phe Leu Pro Leu Ser
225                 230                 235                 240

Leu Cys Thr Leu Ser Pro Gly Arg Cys Leu Arg Leu Ser Pro Phe Gly
                245                 250                 255

His Ser Leu Thr Leu Gly Ser His Cys Glu Ile Cys Ile Asn Arg Ser
            260                 265                 270

Gln Val His Val Pro Gln Glu Phe Ser Ser Thr Gln Leu Ser Phe Phe
        275                 280                 285

Asn Asn Val His Lys Ile Ile Pro Asn Lys Thr Phe Tyr Val Ser Leu
290                 295                 300

Leu Ser Ser Ser Pro Ser Ala Val Lys Ala Gly Leu Ser Gln Pro Ser
305                 310                 315                 320

Leu Leu Tyr Ala Tyr Leu Val Thr Gly His Phe Cys Gly Thr Ile Cys
                325                 330                 335

Pro Ile Phe Ser Thr Asn Gly Lys Gly Arg Leu Ile Met His Leu Leu
            340                 345                 350

Leu Gln Gly Thr Ser Leu His Ile Pro Glu Thr Cys Leu Lys Leu Leu
        355                 360                 365

Cys Glu Asn Ile Gly Pro Thr Tyr Glu Leu Ala Val Asp Leu Val Gly
370                 375                 380

Asp Ala Phe Cys Ile Lys Val Ser Pro Arg Asp Thr Val Tyr Glu Lys
385                 390                 395                 400

Ala Val Asn Val Asp Glu Asp Ala Ile Tyr Glu Ala Ile Lys Asp Leu
                405                 410                 415

Glu Cys Gly Asp Glu Leu Arg Leu Gln Ile Ile Asn Tyr Thr Gln Leu
            420                 425                 430

Ile Leu Glu Asn Lys Gln
        435

<210> SEQ ID NO 4
<211> LENGTH: 230

-continued

<212> TYPE: PRT
<213> ORGANISM: Artificial Sequence
<220> FEATURE:
<223> OTHER INFORMATION: EBV BFRF1 consisting of EBV BFRF1 (Uniprot entry: V5KTU9, 1-MASPEERLLD.. SDMSQQLS-192) is fused via a GGSGS linker to EBV BFLF2 (Uniprot entry: K9UT32, 78-DRSHFSLRD...... -110)

<400> SEQUENCE: 4

```
Met Ala Ser Pro Glu Glu Arg Leu Leu Asp Glu Leu Asn Asn Val Ile
1               5                   10                  15

Val Ser Phe Leu Cys Asp Ser Gly Ser Leu Glu Val Glu Arg Cys Ser
            20                  25                  30

Gly Ala His Val Phe Ser Arg Gly Ser Ser Gln Pro Leu Cys Thr Val
        35                  40                  45

Lys Leu Arg His Gly Gln Ile Tyr His Leu Glu Phe Val Tyr Lys Phe
    50                  55                  60

Leu Ala Phe Lys Leu Lys Asn Cys Asn Tyr Pro Ser Ser Pro Val Phe
65                  70                  75                  80

Val Ile Ser Asn Asn Gly Leu Ala Thr Thr Leu Arg Cys Phe Leu His
                85                  90                  95

Glu Pro Ser Gly Leu Arg Ser Gly Gln Ser Gly Pro Cys Leu Gly Leu
            100                 105                 110

Ser Thr Asp Val Asp Leu Pro Lys Asn Ser Ile Ile Met Leu Gly Gln
        115                 120                 125

Asp Asp Phe Ile Lys Phe Lys Ser Pro Leu Val Phe Pro Ala Glu Leu
    130                 135                 140

Asp Leu Leu Lys Ser Met Val Val Cys Arg Ala Tyr Ile Thr Glu His
145                 150                 155                 160

Arg Thr Thr Met Gln Phe Leu Val Phe Gln Ala Ala Asn Ala Gln Lys
                165                 170                 175

Ala Ser Arg Val Met Asp Met Ile Ser Asp Met Ser Gln Gln Leu Ser
            180                 185                 190

Gly Gly Ser Gly Ser Asp Arg Ser His Phe Ser Leu Arg Asp Phe Phe
        195                 200                 205

Arg Gly Ile Ser Ala Asn Phe Glu Leu Gly Lys Asp Phe Leu Arg Glu
    210                 215                 220

Met Asn Thr Pro Ile His
225                 230
```

<210> SEQ ID NO 5
<211> LENGTH: 439
<212> TYPE: PRT
<213> ORGANISM: Artificial Sequence
<220> FEATURE:
<223> OTHER INFORMATION: VZV orf24 consisting of VZV orf24 (Uniprot entry: Q6QCN1, 16-GDNLLQRI .. TDAYM-189) is fused via a GGSGSGGS linker to VZV orf27 (Uniprot entry: Q6QCM8, 77-SKERSV.... FDDFVPPR-333)

<400> SEQUENCE: 5

```
Gly Asp Asn Leu Leu Gln Arg Ile Arg Leu Val Val Pro Ser Ala Leu
1               5                   10                  15

Gln Cys Cys Asp Gly Asp Leu Pro Ile Phe Asp Pro Gln Arg Pro Pro
            20                  25                  30

Ala Arg Cys Val Phe Gln Phe Asn Gly Glu Asp Asn Val Ser Glu Ala
        35                  40                  45

Phe Pro Val Glu Tyr Ile Met Arg Leu Met Ala Asn Trp Ala Gln Val
    50                  55                  60
```

Asp Cys Asp Pro Tyr Ile Lys Ile Gln Asn Thr Gly Val Ser Val Leu
65                  70                  75                  80

Phe Gln Gly Phe Phe Phe Arg Pro Thr Asn Ala Pro Val Ala Glu Val
                85                  90                  95

Ser Ile Asp Ser Asn Asn Val Ile Leu Ser Ser Thr Leu Ser Thr Gly
            100                 105                 110

Ile Asn Leu Ser Ala Leu Glu Ser Ile Lys Arg Gly Gly Gly Ile Asp
            115                 120                 125

Arg Arg Pro Leu Gln Ala Leu Met Trp Val Asn Cys Phe Val Arg Met
130                 135                 140

Pro Tyr Val Gln Leu Ser Phe Arg Phe Met Gly Pro Glu Asp Pro Ser
145                 150                 155                 160

Arg Thr Ile Lys Leu Met Ala Arg Ala Thr Asp Ala Tyr Met Gly Gly
                165                 170                 175

Ser Gly Ser Gly Gly Ser Ser Lys Glu Arg Ser Val Tyr Arg His Tyr
            180                 185                 190

Phe Asn Tyr Ile Ala Arg Ser Pro Pro Glu Glu Leu Ala Thr Val Arg
            195                 200                 205

Gly Leu Ile Val Pro Ile Ile Lys Thr Thr Pro Val Thr Leu Pro Phe
210                 215                 220

Asn Leu Gly Gln Thr Val Ala Asp Asn Cys Leu Ser Leu Ser Gly Met
225                 230                 235                 240

Gly Tyr His Leu Gly Leu Gly Gly Tyr Cys Pro Thr Cys Thr Ala Ser
                245                 250                 255

Gly Glu Pro Arg Leu Cys Arg Thr Asp Arg Ala Ala Leu Ile Leu Ala
            260                 265                 270

Tyr Val Gln Gln Leu Asn Asn Ile Tyr Glu Tyr Arg Val Phe Leu Ala
            275                 280                 285

Ser Ile Leu Ala Leu Ser Asp Arg Ala Asn Met Gln Ala Ala Ser Ala
290                 295                 300

Glu Pro Leu Leu Ser Ser Val Leu Ala Gln Pro Glu Leu Phe Phe Met
305                 310                 315                 320

Tyr His Ile Met Arg Glu Gly Gly Met Arg Asp Ile Arg Val Leu Phe
                325                 330                 335

Tyr Arg Asp Gly Asp Ala Gly Gly Phe Met Met Tyr Val Ile Phe Pro
            340                 345                 350

Gly Lys Ser Val His Leu His Tyr Arg Leu Ile Asp His Ile Gln Ala
            355                 360                 365

Ala Cys Arg Gly Tyr Lys Ile Val Ala His Val Trp Gln Thr Thr Phe
370                 375                 380

Leu Leu Ser Val Cys Arg Asn Pro Glu Gln Gln Thr Glu Thr Val Val
385                 390                 395                 400

Pro Ser Ile Gly Thr Ser Asp Val Tyr Cys Lys Met Cys Asp Leu Asn
                405                 410                 415

Phe Asp Gly Glu Leu Leu Leu Glu Tyr Lys Arg Leu Tyr Ala Leu Phe
            420                 425                 430

Asp Asp Phe Val Pro Pro Arg
            435

<210> SEQ ID NO 6
<211> LENGTH: 215
<212> TYPE: PRT
<213> ORGANISM: Artificial Sequence
<220> FEATURE:

<223> OTHER INFORMATION: VZV orf24 consisting of VZV orf24 (Uniprot
      entry: Q6QCN1, 16-GDNLLQRI .. TDAYM-189) is fused via a GGSGSGGS linker to VZV orf27 (Uniprot entry: Q6QCM8, 77-SKERSV.....RGLIVPII 99)

<400> SEQUENCE: 6

```
Gly Asp Asn Leu Leu Gln Arg Ile Arg Leu Val Val Pro Ser Ala Leu
1               5                   10                  15

Gln Cys Cys Asp Gly Asp Leu Pro Ile Phe Asp Pro Gln Arg Pro Pro
            20                  25                  30

Ala Arg Cys Val Phe Gln Phe Asn Gly Glu Asp Asn Val Ser Glu Ala
        35                  40                  45

Phe Pro Val Glu Tyr Ile Met Arg Leu Met Ala Asn Trp Ala Gln Val
    50                  55                  60

Asp Cys Asp Pro Tyr Ile Lys Ile Gln Asn Thr Gly Val Ser Val Leu
65                  70                  75                  80

Phe Gln Gly Phe Phe Phe Arg Pro Thr Asn Ala Pro Val Ala Glu Val
                85                  90                  95

Ser Ile Asp Ser Asn Asn Val Ile Leu Ser Ser Thr Leu Ser Thr Gly
            100                 105                 110

Ile Asn Leu Ser Ala Leu Glu Ser Ile Lys Arg Gly Gly Gly Ile Asp
        115                 120                 125

Arg Arg Pro Leu Gln Ala Leu Met Trp Val Asn Cys Phe Val Arg Met
    130                 135                 140

Pro Tyr Val Gln Leu Ser Phe Arg Phe Met Gly Pro Glu Asp Pro Ser
145                 150                 155                 160

Arg Thr Ile Lys Leu Met Ala Arg Ala Thr Asp Ala Tyr Met Gly Gly
                165                 170                 175

Ser Gly Ser Gly Gly Ser Ser Lys Glu Arg Ser Val Tyr Arg His Tyr
            180                 185                 190

Phe Asn Tyr Ile Ala Arg Ser Pro Pro Glu Glu Leu Ala Thr Val Arg
        195                 200                 205

Gly Leu Ile Val Pro Ile Ile
    210                 215
```

<210> SEQ ID NO 7
<211> LENGTH: 29
<212> TYPE: PRT
<213> ORGANISM: Human cytomegalovirus

<400> SEQUENCE: 7

```
Leu Thr Leu His Asp Leu His Asp Ile Phe Arg Glu His Pro Glu Leu
1               5                   10                  15

Glu Leu Lys Tyr Leu Asn Met Met Lys Met Ala Ile Thr
            20                  25
```

<210> SEQ ID NO 8
<211> LENGTH: 376
<212> TYPE: PRT
<213> ORGANISM: Human cytomegalovirus

<400> SEQUENCE: 8

```
Met Ser Ser Val Ser Gly Val Arg Thr Pro Arg Glu Arg Arg Ser Ala
1               5                   10                  15

Leu Arg Ser Leu Leu Arg Lys Arg Arg Gln Arg Glu Leu Ala Ser Lys
            20                  25                  30

Val Ala Ser Thr Val Asn Gly Ala Thr Ser Ala Asn Asn His Gly Glu
        35                  40                  45
```

Pro Pro Ser Pro Ala Asp Ala Arg Pro Arg Leu Thr Leu His Asp Leu
            50                  55                  60

His Asp Ile Phe Arg Glu His Pro Glu Leu Glu Leu Lys Tyr Leu Asn
 65                  70                  75                  80

Met Met Lys Met Ala Ile Thr Gly Lys Glu Ser Ile Cys Leu Pro Phe
                 85                  90                  95

Asn Phe His Ser His Arg Gln His Thr Cys Leu Asp Ile Ser Pro Tyr
            100                 105                 110

Gly Asn Glu Gln Val Ser Arg Ile Ala Cys Thr Ser Cys Glu Asp Asn
            115                 120                 125

Arg Ile Leu Pro Thr Ala Ser Asp Ala Met Val Ala Phe Ile Asn Gln
            130                 135                 140

Thr Ser Asn Ile Met Lys Asn Arg Asn Phe Tyr Tyr Gly Phe Cys Lys
145                 150                 155                 160

Ser Ser Glu Leu Leu Lys Leu Ser Thr Asn Gln Pro Pro Ile Phe Gln
                165                 170                 175

Ile Tyr Tyr Leu Leu His Ala Ala Asn His Asp Ile Val Pro Phe Met
                180                 185                 190

His Ala Glu Asp Gly Arg Leu His Met His Val Ile Phe Glu Asn Pro
            195                 200                 205

Asp Val His Ile Pro Cys Asp Cys Ile Thr Gln Met Leu Thr Ala Ala
            210                 215                 220

Arg Glu Asp Tyr Ser Val Thr Leu Asn Ile Val Arg Asp His Val Val
225                 230                 235                 240

Ile Ser Val Leu Cys His Ala Val Ser Ala Ser Ser Val Lys Ile Asp
                245                 250                 255

Val Thr Ile Leu Gln Arg Lys Ile Asp Glu Met Asp Ile Pro Asn Asp
            260                 265                 270

Val Ser Glu Ser Phe Glu Arg Tyr Lys Glu Leu Ile Gln Glu Leu Cys
            275                 280                 285

Gln Ser Ser Gly Asn Asn Leu Tyr Glu Glu Ala Thr Ser Ser Tyr Ala
            290                 295                 300

Ile Arg Ser Pro Leu Thr Ala Ser Pro Leu His Val Ser Thr Asn
305                 310                 315                 320

Gly Cys Gly Pro Ser Ser Ser Gln Ser Thr Pro Pro His Leu His
                325                 330                 335

Pro Pro Ser Gln Ala Thr Gln Pro His His Tyr Ser His His Gln Ser
            340                 345                 350

Gln Ser Gln Gln His His His Arg Pro Gln Ser Pro Pro Pro Leu
            355                 360                 365

Phe Leu Asn Ser Ile Arg Ala Pro
            370                 375

<210> SEQ ID NO 9
<211> LENGTH: 397
<212> TYPE: PRT
<213> ORGANISM: Human cytomegalovirus

<400> SEQUENCE: 9

Met Glu Met Asn Lys Val Leu His Gln Asp Leu Val Gln Ala Thr Arg
 1               5                  10                  15

Arg Ile Leu Lys Leu Gly Pro Ser Glu Leu Arg Val Thr Asp Ala Gly
            20                  25                  30

Leu Ile Cys Lys Asn Pro Asn Tyr Ser Val Cys Asp Ala Met Leu Lys 35                  40                  45
Thr Asp Thr Val Tyr Cys Val Glu Tyr Leu Leu Ser Tyr Trp Glu Ser
 50                  55                  60

Arg Thr Asp His Val Pro Cys Phe Ile Phe Lys Asn Thr Gly Cys Ala
 65                  70                  75                  80

Val Ser Leu Cys Cys Phe Val Arg Ala Pro Val Lys Leu Val Ser Pro
                     85                  90                  95

Ala Arg His Val Gly Glu Phe Asn Val Leu Lys Val Asn Glu Ser Leu
                    100                 105                 110

Ile Val Thr Leu Lys Asp Ile Glu Glu Ile Lys Pro Ser Ala Tyr Gly
                115                 120                 125

Val Leu Thr Lys Cys Val Val Arg Lys Ser Asn Ser Ala Ser Val Phe
                130                 135                 140

Asn Ile Glu Leu Ile Ala Phe Gly Pro Glu Asn Glu Gly Glu Tyr Glu
145                 150                 155                 160

Asn Leu Leu Arg Glu Leu Tyr Ala Lys Lys Ala Ala Ser Thr Ser Leu
                    165                 170                 175

Ala Val Arg Asn His Val Thr Val Ser Ser His Ser Gly Ser Gly Pro
                    180                 185                 190

Ser Leu Trp Arg Ala Arg Met Ser Ala Ala Leu Thr Arg Thr Ala Gly
                195                 200                 205

Lys Arg Ser Ser Arg Thr Ala Ser Pro Pro Pro Pro Arg His Pro
210                 215                 220

Ser Cys Ser Pro Thr Met Val Ala Ala Gly Ala Ala Ala Gly Pro
225                 230                 235                 240

Arg Pro Pro Pro Pro Met Ala Ala Gly Ser Trp Arg Leu Cys Arg
                    245                 250                 255

Cys Glu Ala Cys Met Gly Arg Cys Gly Cys Ala Ser Glu Gly Asp Ala
                    260                 265                 270

Asp Glu Glu Glu Glu Leu Leu Ala Leu Ala Gly Glu Gly Lys Ala
                    275                 280                 285

Ala Ala Ala Ala Ala Gly Gln Asp Val Gly Gly Ser Ala Arg Arg Pro
                290                 295                 300

Leu Glu Glu His Val Ser Arg Arg Gly Val Ser Thr His His Arg
305                 310                 315                 320

His Pro Pro Ser Pro Cys Ala Pro Ser Leu Glu Arg Thr Gly Tyr
                    325                 330                 335

Arg Trp Ala Pro Ser Ser Trp Trp Arg Ala Arg Ser Gly Pro Ser Arg
                340                 345                 350

Pro Gln Ser Gly Pro Trp Leu Pro Ala Arg Phe Ala Thr Leu Gly Pro
                355                 360                 365

Leu Val Leu Ala Leu Leu Val Leu Ala Leu Trp Arg Gly His
                370                 375                 380

Gly Gln Ser Ser Ser Pro Thr Arg Ser Ala His Arg Asp
385                 390                 395

<210> SEQ ID NO 10
<211> LENGTH: 306
<212> TYPE: PRT
<213> ORGANISM: human herpesvirus 1

<400> SEQUENCE: 10

Met Tyr Asp Thr Asp Pro His Arg Arg Gly Ser Arg Pro Gly Pro Tyr
 1               5                  10                  15

```
His Gly Lys Glu Arg Arg Arg Ser Arg Ser Ser Ala Ala Gly Gly Thr
            20                  25                  30

Leu Gly Val Val Arg Arg Ala Ser Arg Lys Ser Leu Pro Pro His Ala
        35                  40                  45

Arg Lys Gln Glu Leu Cys Leu His Glu Arg Gln Arg Tyr Arg Gly Leu
    50                  55                  60

Phe Ala Ala Leu Ala Gln Thr Pro Ser Glu Glu Ile Ala Ile Val Arg
65                  70                  75                  80

Ser Leu Ser Val Pro Leu Val Lys Thr Thr Pro Val Ser Leu Pro Phe
                85                  90                  95

Cys Leu Asp Gln Thr Val Ala Asp Asn Cys Leu Thr Leu Ser Gly Met
            100                 105                 110

Gly Tyr Tyr Leu Gly Ile Gly Gly Cys Cys Pro Ala Cys Asn Ala Gly
        115                 120                 125

Asp Gly Arg Phe Ala Ala Thr Ser Arg Glu Ala Leu Ile Leu Ala Phe
    130                 135                 140

Val Gln Gln Ile Asn Thr Ile Phe Glu His Arg Ala Phe Leu Ala Ser
145                 150                 155                 160

Leu Val Val Leu Ala Asp Arg His Asn Ala Pro Leu Gln Asp Leu Leu
                165                 170                 175

Ala Gly Ile Leu Gly Gln Pro Glu Leu Phe Phe Val His Thr Ile Leu
            180                 185                 190

Arg Gly Gly Gly Ala Cys Asp Pro Arg Leu Leu Phe Tyr Pro Asp Pro
        195                 200                 205

Thr Tyr Gly Gly His Met Leu Tyr Val Ile Phe Pro Gly Thr Ser Ala
    210                 215                 220

His Leu His Tyr Arg Leu Ile Asp Arg Met Leu Thr Ala Cys Pro Gly
225                 230                 235                 240

Tyr Arg Phe Val Ala His Val Trp Gln Ser Thr Phe Val Leu Val Val
                245                 250                 255

Arg Arg Asn Ala Glu Lys Pro Thr Asp Ala Glu Ile Pro Thr Val Ser
            260                 265                 270

Ala Ala Asp Ile Tyr Cys Lys Met Arg Asp Ile Ser Phe Asp Gly Gly
        275                 280                 285

Leu Met Leu Glu Tyr Gln Arg Leu Tyr Ala Thr Phe Asp Glu Phe Pro
    290                 295                 300

Pro Pro
305

<210> SEQ ID NO 11
<211> LENGTH: 305
<212> TYPE: PRT
<213> ORGANISM: human herpesvirus 2

<400> SEQUENCE: 11

Met Tyr Asp Ile Ala Pro Arg Arg Ser Gly Ser Arg Pro Gly Pro Gly
1               5                   10                  15

Arg Asp Lys Thr Arg Arg Ser Arg Phe Ser Ala Ala Gly Asn Pro
            20                  25                  30

Gly Val Glu Arg Arg Ala Ser Arg Lys Ser Leu Pro Ser His Ala Arg
        35                  40                  45

Arg Leu Glu Leu Cys Leu His Glu Arg Arg Tyr Arg Gly Phe Phe
    50                  55                  60

Ala Ala Leu Ala Gln Thr Pro Ser Glu Glu Ile Ala Ile Val Arg Ser
65                  70                  75                  80
```

```
Leu Ser Val Pro Leu Val Lys Thr Thr Pro Val Ser Leu Pro Phe Ser
                85                  90                  95

Leu Asp Gln Thr Val Ala Asp Asn Cys Leu Thr Leu Ser Gly Met Gly
            100                 105                 110

Tyr Tyr Leu Gly Ile Gly Gly Cys Cys Pro Ala Cys Ser Ala Gly Asp
        115                 120                 125

Gly Arg Leu Ala Thr Val Ser Arg Glu Ala Leu Ile Leu Ala Phe Val
    130                 135                 140

Gln Gln Ile Asn Thr Ile Phe Glu His Arg Thr Phe Leu Ala Ser Leu
145                 150                 155                 160

Val Val Leu Ala Asp Arg His Ser Thr Pro Leu Gln Asp Leu Leu Ala
                165                 170                 175

Asp Thr Leu Gly Gln Pro Glu Leu Phe Phe Val His Thr Ile Leu Arg
            180                 185                 190

Gly Gly Gly Ala Cys Asp Pro Arg Phe Leu Phe Tyr Pro Asp Pro Thr
        195                 200                 205

Tyr Gly Gly His Met Leu Tyr Val Ile Phe Pro Gly Thr Ser Ala His
    210                 215                 220

Leu His Tyr Arg Leu Ile Asp Arg Met Leu Thr Ala Cys Pro Gly Tyr
225                 230                 235                 240

Arg Phe Ala Ala His Val Trp Gln Ser Thr Phe Val Leu Val Val Arg
                245                 250                 255

Arg Asn Ala Glu Lys Pro Ala Asp Ala Glu Ile Pro Thr Val Ser Ala
            260                 265                 270

Ala Asp Ile Tyr Cys Lys Met Arg Asp Ile Ser Phe Asp Gly Gly Leu
        275                 280                 285

Met Leu Glu Tyr Gln Arg Leu Tyr Ala Thr Phe Asp Glu Phe Pro Pro
    290                 295                 300

Pro
305

<210> SEQ ID NO 12
<211> LENGTH: 333
<212> TYPE: PRT
<213> ORGANISM: Human herpesvirus 3

<400> SEQUENCE: 12

Met His Leu Lys Pro Thr Arg Phe Phe His Ala Asn Gln Pro Pro Met
1               5                   10                  15

Pro His Ser Tyr Glu Met Glu Asp Leu Cys Phe Asp Asp Met Gln Tyr
                20                  25                  30

Arg Trp Ser Pro Ser Asn Thr Pro Tyr Arg Ser Met Ser Arg Arg Tyr
            35                  40                  45

Lys Ser Val Ser Arg Ser Gly Pro Ser Met Arg Val Arg Ser Arg Thr
        50                  55                  60

Pro Cys Arg Arg Gln Thr Ile Arg Gly Lys Leu Met Ser Lys Glu Arg
65                  70                  75                  80

Ser Val Tyr Arg His Tyr Phe Asn Tyr Ile Ala Arg Ser Pro Pro Glu
                85                  90                  95

Glu Leu Ala Thr Val Arg Gly Leu Ile Val Pro Ile Ile Lys Thr Thr
            100                 105                 110

Pro Val Thr Leu Pro Phe Asn Leu Gly Gln Thr Val Ala Asp Asn Cys
        115                 120                 125

Leu Ser Leu Ser Gly Met Gly Tyr His Leu Gly Leu Gly Gly Tyr Cys
```

```
                130                 135                 140
Pro Thr Cys Thr Ala Ser Gly Glu Pro Arg Leu Cys Arg Thr Asp Arg
145                 150                 155                 160

Ala Ala Leu Ile Leu Ala Tyr Val Gln Gln Leu Asn Asn Ile Tyr Glu
                165                 170                 175

Tyr Arg Val Phe Leu Ala Ser Ile Leu Ala Leu Ser Asp Arg Ala Asn
                180                 185                 190

Met Gln Ala Ala Ser Ala Glu Pro Leu Leu Ser Ser Val Leu Ala Gln
                195                 200                 205

Pro Glu Leu Phe Phe Met Tyr His Ile Met Arg Glu Gly Gly Met Arg
                210                 215                 220

Asp Ile Arg Val Leu Phe Tyr Arg Asp Gly Asp Ala Gly Gly Phe Met
225                 230                 235                 240

Met Tyr Val Ile Phe Pro Gly Lys Ser Val His Leu His Tyr Arg Leu
                245                 250                 255

Ile Asp His Ile Gln Ala Ala Cys Arg Gly Tyr Lys Ile Val Ala His
                260                 265                 270

Val Trp Gln Thr Thr Phe Leu Leu Ser Val Cys Arg Asn Pro Glu Gln
                275                 280                 285

Gln Thr Glu Thr Val Val Pro Ser Ile Gly Thr Ser Asp Val Tyr Cys
                290                 295                 300

Lys Met Cys Asp Leu Asn Phe Asp Gly Glu Leu Leu Leu Glu Tyr Lys
305                 310                 315                 320

Arg Leu Tyr Ala Leu Phe Asp Asp Phe Val Pro Pro Arg
                325                 330

<210> SEQ ID NO 13
<211> LENGTH: 264
<212> TYPE: PRT
<213> ORGANISM: Human herpesvirus 6

<400> SEQUENCE: 13

Met Thr Val His Lys Ser Arg Ile Arg Arg Ser Arg Ser Leu Ser Val
1               5                   10                  15

Thr His Arg Ile Gln Lys Arg Pro Asp His Arg Glu Lys Thr Lys Leu
                20                  25                  30

Tyr Leu Gln Leu Lys Leu His Asp Leu His Thr Val Phe Asn Leu Phe
                35                  40                  45

Pro Glu Tyr Glu Gln Lys Phe Leu Ala Ile Ile Lys Leu Pro Ile Thr
            50                  55                  60

Gly Lys Glu Pro Ile Asp Val Pro Phe Ser Leu Ser Asn His His Gln
65                  70                  75                  80

His Thr Cys Leu Glu Phe Ser Pro Tyr Ala Asn Glu Gln Ile Ser Lys
                85                  90                  95

Ser Ala Cys Leu His Cys Glu Ser Val Ser Val Pro Thr Ser Ser Asp
                100                 105                 110

Ala Met Val Ala His Leu Asn Gln Val Asn Asn Val Met Gln Asn Arg
                115                 120                 125

Leu Tyr Phe Tyr Gly Phe Arg Lys Asp Met Glu Leu Ile Arg Met Ser
                130                 135                 140

Ala Lys Gln Pro Thr Ile Phe Gln Ile Phe Tyr Ile Val His Asn Thr
145                 150                 155                 160

Ile Asn Asn Ile Phe Pro Ile Met Phe Glu Arg Lys Gln Lys Leu Gly
                165                 170                 175
```

-continued

```
Met His Ile Val Phe Gln Ser Arg Thr Leu His Ile Pro Cys Glu Cys
            180                 185                 190

Ile Lys Gln Ile Val Ala Val Ser Ser Gly Tyr Asn Val Tyr Leu Asp
        195                 200                 205

Ile Leu Gln Glu Ser Val Ile Leu Thr Val Leu Cys Glu Thr Leu Asp
    210                 215                 220

Thr Asn Thr Asn Ile His Ile Asp Ile Gly Met Leu Gln Lys Lys Leu
225                 230                 235                 240

Glu Glu Met Asp Ile Pro Asn Glu Ile Ser Asp Arg Leu Glu Lys Tyr
                245                 250                 255

Lys Gly His Leu Ile Gly Phe His
            260

<210> SEQ ID NO 14
<211> LENGTH: 264
<212> TYPE: PRT
<213> ORGANISM: Human herpesvirus 6B

<400> SEQUENCE: 14

Met Thr Val His Lys Asn Arg Phe Arg Arg Ser Arg Ser Leu Ser Val
1               5                   10                  15

Thr His Arg Ile Gln Lys Arg Pro Asp His Arg Glu Lys Thr Lys Leu
            20                  25                  30

Tyr Leu Gln Leu Lys Leu His Asp Leu His Ala Val Phe Asn Leu Phe
        35                  40                  45

Pro Glu Tyr Glu Gln Lys Phe Leu Ala Ile Ile Lys Leu Pro Ile Thr
    50                  55                  60

Gly Lys Glu Pro Ile Asp Val Pro Phe Ser Leu Ser Asn His His Gln
65                  70                  75                  80

His Thr Cys Leu Glu Phe Ser Pro Tyr Ala Asn Glu Gln Ile Ser Lys
                85                  90                  95

Ser Ala Cys Leu His Cys Glu Ser Val Ser Val Pro Thr Ser Ser Asp
            100                 105                 110

Ala Met Val Ala His Leu Asn Gln Val Thr Asn Val Met Gln Asn Arg
        115                 120                 125

Phe Tyr Phe Tyr Gly Phe Arg Lys Asp Met Glu Leu Ile Arg Met Ser
    130                 135                 140

Ala Lys Gln Pro Thr Ile Phe Gln Ile Phe Tyr Ile Val His Asn Thr
145                 150                 155                 160

Ile Asn Asn Ile Phe Pro Ile Met Phe Glu Lys Lys Gln Lys Leu Gly
                165                 170                 175

Met His Ile Val Phe Gln Ser Arg Thr Leu His Ile Pro Cys Glu Cys
            180                 185                 190

Ile Lys Gln Ile Ile Ala Val Ser Ser Gly Tyr Asn Val Tyr Leu Asp
        195                 200                 205

Ile Leu Gln Asp Ser Val Ile Leu Thr Val Leu Cys Glu Thr Leu Asp
    210                 215                 220

Thr Asn Thr Asn Ile His Ile Asp Ile Gly Met Leu Gln Lys Lys Leu
225                 230                 235                 240

Glu Glu Met Asp Ile Pro Asn Glu Ile Ser Asp Arg Leu Glu Lys Tyr
                245                 250                 255

Lys Gly His Leu Ile Gly Phe His
            260

<210> SEQ ID NO 15
```

```
-continued

<211> LENGTH: 259
<212> TYPE: PRT
<213> ORGANISM: Human herpesvirus 7

<400> SEQUENCE: 15

Met Ala Ile Gln Ser Thr Arg Arg Leu Arg Ala Ser Ser Leu Leu
1               5                   10                  15

Lys Lys Ser Lys Pro Tyr Asn Lys Glu Lys Thr Asn Leu Ser Leu Ser
            20                  25                  30

Leu Ser Leu Lys Glu Leu His Ser Val Phe Lys Leu Phe Pro Glu Tyr
        35                  40                  45

Glu Leu Lys Phe Leu Asn Met Met Lys Leu Pro Ile Thr Gly Lys Glu
50                  55                  60

Pro Ile Lys Ile Pro Phe Asp Leu Ser Leu His His Gln His Thr Cys
65                  70                  75                  80

Leu Asp Leu Ser Pro Tyr Ala Asn Glu Gln Val Ser Lys Ser Ala Cys
                85                  90                  95

Val Asn Cys Gly Thr Thr Asn Ile Pro Thr Ala Ser Asp Ala Met Val
            100                 105                 110

Ala Tyr Met Asn Gln Ile Ser Asn Val Met Gln Asn Arg Leu Tyr Tyr
        115                 120                 125

Tyr Gly Phe Gln Lys Lys Val Glu Leu Ile Arg Met Ser Ala Lys Gln
    130                 135                 140

Pro Thr Leu Phe Gln Ile Phe Tyr Ile Leu Ser Ser Ile Ala Ser Asn
145                 150                 155                 160

Phe Leu Pro Ile Met Phe Glu Asn Asn Glu Lys Leu Asn Met Tyr Val
                165                 170                 175

Val Phe Gln Thr Arg Thr Leu His Ile Pro Cys Glu Cys Ile Asn Gln
            180                 185                 190

Ile Met Thr Val Ser Ser Gly Tyr Thr Val Leu Leu Asp Ile Leu His
        195                 200                 205

Asp Ser Ile Val Leu His Val Leu Cys Lys Thr Ile Glu Thr Ser Asn
    210                 215                 220

Ile Gln Ile Asp Ile Asn Val Leu Gln Arg Lys Ile Glu Glu Met Asp
225                 230                 235                 240

Val Pro Asp Glu Ile Gly Asp Lys Phe Glu Lys Leu Lys His Ile Leu
                245                 250                 255

Pro Phe Ile

<210> SEQ ID NO 16
<211> LENGTH: 318
<212> TYPE: PRT
<213> ORGANISM: Human herpesvirus 4

<400> SEQUENCE: 16

Met Ala Pro Val Thr Pro Asp Ala Val Asn Ala Arg Gln Gln Arg Pro
1               5                   10                  15

Ala Asp Pro Ala Leu Arg Arg Leu Met His Pro His His Arg Asn Tyr
            20                  25                  30

Thr Ala Ser Lys Ala Ser Ala His Ser Val Lys Ser Val Ser Arg Cys
        35                  40                  45

Gly Lys Ser Arg Ser Glu Leu Gly Arg Met Glu Arg Val Gly Ser Val
    50                  55                  60

Ala Arg Ser Ile Cys Ser Arg His Thr Arg His Gly Val Asp Arg Ser
65                  70                  75                  80
```

```
His Phe Ser Leu Arg Asp Phe Phe Arg Gly Ile Ser Ala Asn Phe Glu
                85                  90                  95

Leu Gly Lys Asp Phe Leu Arg Glu Met Asn Thr Pro Ile His Val Ser
            100                 105                 110

Glu Ala Val Phe Leu Pro Leu Ser Leu Cys Thr Leu Ser Pro Gly Arg
            115                 120                 125

Cys Leu Arg Leu Ser Pro Phe Gly His Ser Leu Thr Leu Gly Ser His
    130                 135                 140

Cys Glu Ile Cys Ile Asn Arg Ser Gln Val His Val Pro Gln Glu Phe
145                 150                 155                 160

Ser Ser Thr Gln Leu Ser Phe Phe Asn Asn Val His Lys Ile Ile Pro
                165                 170                 175

Asn Lys Thr Phe Tyr Val Ser Leu Leu Ser Ser Pro Ser Ala Val
            180                 185                 190

Lys Ala Gly Leu Ser Gln Pro Ser Leu Leu Tyr Ala Tyr Leu Val Thr
            195                 200                 205

Gly His Phe Cys Gly Thr Ile Cys Pro Ile Phe Ser Thr Asn Gly Lys
    210                 215                 220

Gly Arg Leu Ile Met His Leu Leu Gln Gly Thr Ser Leu His Ile
225                 230                 235                 240

Pro Glu Thr Cys Leu Lys Leu Cys Glu Asn Ile Gly Pro Thr Tyr
                245                 250                 255

Glu Leu Ala Val Asp Leu Val Gly Asp Ala Phe Cys Ile Lys Val Ser
            260                 265                 270

Pro Arg Asp Thr Val Tyr Glu Lys Ala Val Asn Val Asp Glu Asp Ala
            275                 280                 285

Ile Tyr Glu Ala Ile Lys Asp Leu Glu Cys Gly Asp Glu Leu Arg Leu
            290                 295                 300

Gln Ile Ile Asn Tyr Thr Gln Leu Ile Leu Glu Asn Lys Gln
305                 310                 315

<210> SEQ ID NO 17
<211> LENGTH: 302
<212> TYPE: PRT
<213> ORGANISM: Human herpesvirus 8

<400> SEQUENCE: 17

Met Pro Lys Ser Val Ser Ser His Ile Ser Leu Ala Thr Ser Thr Gly
1               5                   10                  15

Arg Ser Gly Pro Arg Asp Ile Arg Arg Cys Leu Ser Ser Arg Leu Arg
            20                  25                  30

Ser Val Pro Pro Gly Ala Arg Ser Ala Ser Val Ser Ser Lys His Arg
        35                  40                  45

Asn Gly Leu Arg Lys Phe Ile Ser Asp Lys Val Phe Phe Ser Ile Leu
    50                  55                  60

Ser His Arg His Glu Leu Gly Val Asp Phe Leu Arg Glu Met Glu Thr
65                  70                  75                  80

Pro Ile Cys Thr Ser Lys Thr Val Met Leu Pro Leu Asp Leu Ser Thr
                85                  90                  95

Val Ala Pro Gly Arg Cys Val Ser Leu Ser Pro Phe Gly His Ser Ser
            100                 105                 110

Asn Met Gly Phe Gln Cys Ala Leu Cys Pro Ser Thr Glu Asn Pro Thr
            115                 120                 125

Val Ala Gln Gly Ser Arg Pro Gln Thr Met Val Gly Asp Ala Leu Lys
        130                 135                 140
```

```
Lys Asn Asn Glu Leu Cys Ser Val Ala Leu Ala Phe Tyr His His Ala
145                 150                 155                 160

Asp Lys Val Ile Gln His Lys Thr Phe Tyr Leu Ser Leu Leu Ser His
            165                 170                 175

Ser Met Asp Val Val Arg Gln Ser Phe Leu Gln Pro Gly Leu Leu Tyr
            180                 185                 190

Ala Asn Leu Val Leu Lys Thr Phe Gly His Asp Pro Leu Pro Ile Phe
            195                 200                 205

Thr Thr Asn Asn Gly Met Leu Thr Met Cys Ile Leu Phe Lys Thr Arg
        210                 215                 220

Ala Leu His Leu Gly Glu Thr Ala Leu Arg Leu Leu Met Asp Asn Leu
225                 230                 235                 240

Pro Asn Tyr Lys Ile Ser Ala Asp Cys Cys Arg Gln Ser Tyr Val Val
                245                 250                 255

Lys Phe Val Pro Thr His Pro Asp Thr Ala Ser Ile Ala Val Gln Val
            260                 265                 270

His Thr Ile Cys Glu Ala Val Ala Ala Leu Asp Cys Thr Asp Glu Met
            275                 280                 285

Arg Asp Asp Ile Gln Lys Gly Thr Ala Leu Val Asn Ala Leu
            290                 295                 300

<210> SEQ ID NO 18
<211> LENGTH: 271
<212> TYPE: PRT
<213> ORGANISM: PrV

<400> SEQUENCE: 18

Met Phe Glu Arg Arg Arg Leu Leu Arg Arg Lys Ser Ser Ala Ala Arg
1               5                   10                  15

Arg Lys Thr Leu Thr Arg Ala Ala Arg Asp Arg Tyr Ala Pro Tyr Phe
            20                  25                  30

Ala Tyr Ala Ala Ala Gln Pro Ser Asp Glu Val Thr Thr Val Arg Gly
        35                  40                  45

Leu Ser Asn Pro Leu Ile Lys Thr Ala Pro Val Thr Leu Pro Phe Asp
50                  55                  60

Leu Gly Gln Ala Val Ala Asp Asn Cys Leu Ser Leu Ser Gly Met Gly
65                  70                  75                  80

Tyr Tyr Leu Gly Leu Gly Gly Cys Cys Pro Thr Cys Ala Ala Ala Glu
                85                  90                  95

Pro Arg Leu Gly Arg Ser Asp Arg Ala Ala Leu Val Leu Ala Tyr Val
            100                 105                 110

Gln Gln Leu Asn Ser Ile Tyr Glu Tyr Arg Val Phe Leu Ala Ser Val
        115                 120                 125

Ala Ala Arg Asp Pro Ser Glu Arg Ala Leu Glu Glu Val Leu Ala His
130                 135                 140

Pro Glu Leu Phe Phe Ala Tyr Tyr Val Leu Arg Asp Gly Gly Leu Arg
145                 150                 155                 160

Asp Val Arg Val Leu Phe Phe Glu Asp Pro Asp Ala Gln Gly Ala Leu
            165                 170                 175

Met Met Tyr Val Val Phe Pro Glu Lys Ser Val His Val His His Arg
            180                 185                 190

Val Leu Asp Arg Leu Leu Gly Ala Cys Ala Gly His Arg Ile Val Ala
        195                 200                 205

His Val Trp Gln Thr Met Phe Val Leu Val Val Arg Lys Lys Gly Asp
```

Gly Arg Pro Ala Asp Asp Val Pro Ala Val Ser Ala Ser Asp Ile Tyr
225                 230                 235                 240

Cys Lys Met Arg Asp Ile Ser Phe Asp Gly Glu Leu Leu Leu Glu Tyr
            245                 250                 255

Lys Arg Leu Tyr Ala Ala Phe Glu Asp Phe Arg Pro Pro Arg Pro
        260                 265                 270

<210> SEQ ID NO 19
<211> LENGTH: 333
<212> TYPE: PRT
<213> ORGANISM: Mouse cytomegalovirus 1

<400> SEQUENCE: 19

Met Phe Arg Ser Pro Glu Gly Glu Arg Asp Ala Ala Asp Arg Glu
1               5                   10                  15

Glu Glu Glu Gly Gly Glu Ala Arg Arg Ser Arg Met Met Met Ser
            20                  25                  30

Pro Arg Arg Val Lys Arg Ala Arg His Arg Pro Ala Gly Ser Gly Leu
                35                  40                  45

Arg Thr Pro Leu Arg Ser Pro Ser Ala Cys Arg Cys Ser Ser Pro Ser
50                  55                  60

Pro Glu Arg Gln Trp Gln Arg Arg Ala Glu Lys Arg Ser Thr
65                  70                  75                  80

Thr Pro Thr Asp Pro Pro Pro Pro Lys Arg Ser Ala Ala Ser Ala
                85                  90                  95

Ala Ala Gly Ala Ala Ala Pro Glu Ser Glu Tyr Leu Asn Val Lys Leu
            100                 105                 110

Ser Glu Leu His Asp Val Phe Gln Arg His Pro Asp Leu Glu Gln Lys
        115                 120                 125

Tyr Leu Lys Ile Met Lys Leu Pro Ile Thr Gly Lys Glu Ser Ile Arg
    130                 135                 140

Leu Pro Phe Asp Phe Lys Ser His Arg Gln His Thr Cys Leu Asp Leu
145                 150                 155                 160

Ser Pro Tyr Gly Asn Asp Gln Val Ser Arg Ser Ala Cys Thr Thr Cys
                165                 170                 175

Lys Glu Thr Thr Arg Leu Pro Thr Ala Ser Asp Ser Met Val Ala Phe
            180                 185                 190

Ile Asn Gln Thr Ser Asn Val Met Lys His Arg Lys Phe Tyr Phe Gly
        195                 200                 205

Phe Arg Lys Asn Met Glu Leu Leu Lys Met Ala Ala Asn Gln Pro Gln
    210                 215                 220

Leu Phe Gln Ile Tyr Tyr Ile Val Gln Ser Cys Val Gln Glu Ile Val
225                 230                 235                 240

Pro Leu Ile Tyr Tyr Asp Arg Glu Met Ala His Met Gln Leu Ile Phe
                245                 250                 255

Glu Lys Glu Thr Val His Ile Pro Ser Gln Cys Ile Glu Gln Ile Leu
            260                 265                 270

Thr Val Ala Lys Asp Ala Tyr Gly Val Ser Leu Asp Ile Ala His Gln
        275                 280                 285

Arg Ile Thr Leu Thr Ala Arg Cys Leu Arg Leu Glu Ser Ser Ser Leu
    290                 295                 300

Arg Ile Asp Val Leu Met Leu Gln Arg Lys Val Asp Glu Leu Glu Ile
305                 310                 315                 320

```
Pro Asn Glu Thr Asn Glu Lys Phe Glu Ser Tyr Ser Leu
            325                 330
```

<210> SEQ ID NO 20
<211> LENGTH: 275
<212> TYPE: PRT
<213> ORGANISM: human herpesvirus 1

<400> SEQUENCE: 20

```
Met Ala Gly Leu Gly Lys Pro Tyr Thr Gly His Pro Gly Asp Ala Phe
1               5                   10                  15

Glu Gly Leu Val Gln Arg Ile Arg Leu Ile Val Pro Ser Thr Leu Arg
                20                  25                  30

Gly Gly Asp Gly Glu Ala Gly Pro Tyr Ser Pro Ser Ser Leu Pro Ser
            35                  40                  45

Arg Cys Ala Phe Gln Phe His Gly His Asp Gly Ser Asp Glu Ser Phe
        50                  55                  60

Pro Ile Glu Tyr Val Leu Arg Leu Met Asn Asp Trp Ala Glu Val Pro
65                  70                  75                  80

Cys Asn Pro Tyr Leu Arg Ile Gln Asn Thr Gly Val Ser Val Leu Phe
                85                  90                  95

Gln Gly Phe Phe His Arg Pro His Asn Ala Pro Gly Gly Ala Ile Thr
                100                 105                 110

Pro Glu Arg Thr Asn Val Ile Leu Gly Ser Thr Glu Thr Thr Gly Leu
            115                 120                 125

Ser Leu Gly Asp Leu Asp Thr Ile Lys Gly Arg Leu Gly Leu Asp Ala
        130                 135                 140

Arg Pro Met Met Ala Ser Met Trp Ile Ser Cys Phe Val Arg Met Pro
145                 150                 155                 160

Arg Val Gln Leu Ala Phe Arg Phe Met Gly Pro Glu Asp Ala Gly Arg
                165                 170                 175

Thr Arg Arg Ile Leu Cys Arg Ala Ala Glu Gln Ala Ile Thr Arg Arg
            180                 185                 190

Arg Arg Thr Arg Arg Ser Arg Glu Ala Tyr Gly Ala Glu Ala Gly Leu
        195                 200                 205

Gly Val Ala Gly Thr Gly Phe Arg Ala Arg Gly Asp Gly Phe Gly Pro
    210                 215                 220

Leu Pro Leu Leu Thr Gln Gly Pro Ser Arg Pro Trp His Gln Ala Leu
225                 230                 235                 240

Arg Gly Leu Lys His Leu Arg Ile Gly Pro Pro Ala Leu Val Leu Ala
                245                 250                 255

Ala Gly Leu Val Leu Gly Ala Ala Ile Trp Trp Val Val Gly Ala Gly
                260                 265                 270

Ala Arg Leu
        275
```

<210> SEQ ID NO 21
<211> LENGTH: 276
<212> TYPE: PRT
<213> ORGANISM: human herpesvirus 2

<400> SEQUENCE: 21

```
Met Ala Gly Met Gly Lys Pro Tyr Gly Gly Arg Pro Gly Asp Ala Phe
1               5                   10                  15

Glu Gly Leu Val Gln Arg Ile Arg Leu Ile Val Pro Ala Thr Leu Arg
                20                  25                  30
```

```
Gly Gly Gly Gly Glu Ser Gly Pro Tyr Ser Pro Ser Asn Pro Pro Ser
            35                  40                  45

Arg Cys Ala Phe Gln Phe His Gly Gln Asp Gly Ser Asp Glu Ala Phe
 50                      55                  60

Pro Ile Glu Tyr Val Leu Arg Leu Met Asn Asp Trp Ala Asp Val Pro
 65                  70                  75                  80

Cys Asn Pro Tyr Leu Arg Val Gln Asn Thr Gly Val Ser Val Leu Phe
                 85                  90                  95

Gln Gly Phe Phe Asn Arg Pro His Gly Ala Pro Gly Gly Ala Ile Thr
             100                 105                 110

Ala Glu Gln Thr Asn Val Ile Leu His Ser Thr Glu Thr Thr Gly Leu
         115                 120                 125

Ser Leu Gly Asp Leu Asp Asp Val Lys Gly Arg Leu Gly Leu Asp Ala
 130                 135                 140

Arg Pro Met Met Ala Ser Met Trp Ile Ser Cys Phe Val Arg Met Pro
 145                 150                 155                 160

Arg Val Gln Leu Ala Phe Arg Phe Met Gly Pro Glu Asp Ala Val Arg
                 165                 170                 175

Thr Arg Arg Ile Leu Cys Arg Ala Ala Glu Gln Ala Leu Ala Arg Arg
             180                 185                 190

Arg Ser Arg Ser Gln Asp Asp Tyr Gly Ala Val Val Val Ala
         195                 200                 205

Ala Ala His His Ser Ser Gly Ala Pro Gly Pro Gly Val Ala Ala Ser
 210                 215                 220

Gly Pro Pro Ala Pro Pro Gly Arg Gly Pro Ala Arg Pro Trp His Gln
 225                 230                 235                 240

Ala Val Gln Leu Phe Arg Ala Pro Arg Pro Gly Pro Ala Leu Leu
                 245                 250                 255

Leu Leu Ala Ala Gly Leu Phe Leu Gly Ala Ala Ile Trp Trp Ala Val
             260                 265                 270

Gly Ala Arg Leu
         275

<210> SEQ ID NO 22
<211> LENGTH: 269
<212> TYPE: PRT
<213> ORGANISM: Human herpesvirus 3

<400> SEQUENCE: 22

Met Ser Arg Arg Thr Tyr Val Arg Ser Glu Arg Arg Gly Cys Gly
 1               5                  10                  15

Asp Asn Leu Leu Gln Arg Ile Arg Leu Val Val Pro Ser Ala Leu Gln
             20                  25                  30

Cys Cys Asp Gly Asp Leu Pro Ile Phe Asp Pro Gln Arg Pro Pro Ala
         35                  40                  45

Arg Cys Val Phe Gln Phe Asn Gly Glu Asp Asn Val Ser Glu Ala Phe
 50                      55                  60

Pro Val Glu Tyr Ile Met Arg Leu Met Ala Asn Trp Ala Gln Val Asp
 65                  70                  75                  80

Cys Asp Pro Tyr Ile Lys Ile Gln Asn Thr Gly Val Ser Val Leu Phe
                 85                  90                  95

Gln Gly Phe Phe Phe Arg Pro Thr Asn Ala Pro Val Ala Glu Val Ser
             100                 105                 110

Ile Asp Ser Asn Asn Val Ile Leu Ser Ser Thr Leu Ser Thr Gly Ile
         115                 120                 125
```

```
Asn Leu Ser Ala Leu Glu Ser Ile Lys Arg Gly Gly Ile Asp Arg
    130                 135                 140

Arg Pro Leu Gln Ala Leu Met Trp Val Asn Cys Phe Val Arg Met Pro
145                 150                 155                 160

Tyr Val Gln Leu Ser Phe Arg Phe Met Gly Pro Glu Asp Pro Ser Arg
                165                 170                 175

Thr Ile Lys Leu Met Ala Arg Ala Thr Asp Ala Tyr Met Tyr Lys Glu
                180                 185                 190

Thr Gly Asn Asn Leu Asp Glu Tyr Ile Arg Trp Arg Pro Ser Phe Arg
                195                 200                 205

Ser Pro Pro Glu Asn Gly Ser Pro Asn Thr Ser Val Gln Met Gln Ser
    210                 215                 220

Asp Ile Lys Pro Ala Leu Pro Asp Thr Gln Thr Thr Arg Val Trp Lys
225                 230                 235                 240

Leu Ala Leu Pro Val Ala Asn Val Thr Tyr Ala Leu Phe Ile Val Ile
                245                 250                 255

Val Leu Val Val Val Leu Gly Ala Val Leu Phe Trp Lys
                260                 265

<210> SEQ ID NO 23
<211> LENGTH: 276
<212> TYPE: PRT
<213> ORGANISM: Human herpesvirus 6A

<400> SEQUENCE: 23

Met Ala Asn Val Leu Lys Glu Lys Met Tyr Asp Glu Leu Leu Ser Ala
1               5                   10                  15

Thr Cys Arg Ile Leu Lys Leu Gly Ser His Asp Tyr Arg Ile Thr Glu
                20                  25                  30

Arg Asn Leu Leu Ser Lys Asn Pro Lys Phe Pro Leu Cys Asp Ile Ile
                35                  40                  45

Leu Lys Leu Asp Tyr Ala Tyr Asn Leu Glu Tyr Leu Leu Ser Leu Trp
    50                  55                  60

Glu His Val Thr Lys Gln Glu Pro Arg Phe Val Phe Lys Asn Thr Gly
65                  70                  75                  80

Gly Ala Val Ser Met Ser Cys Tyr Leu His Ala Pro Val Lys Val Glu
                85                  90                  95

Gly His His Ala Val Arg Glu Cys Asn Ile Leu Arg Val Asn Glu Cys
                100                 105                 110

Leu Thr Val Arg Met Ser Asp Ile Val Ala Met Lys Pro Ser Thr Phe
            115                 120                 125

Ala Val Phe Thr Lys Cys Ile Ile Arg Arg Asn Arg Asp Asp Thr Tyr
            130                 135                 140

Val Val Glu Phe Val Ala Phe Gly Pro Glu Asn Glu Ser Glu Tyr Ile
145                 150                 155                 160

Ser Leu Leu Lys Ala Ile Phe Leu Lys Lys Cys Ser Met Gly Lys Gln
                165                 170                 175

His Leu Glu Ser Asn Arg Phe Cys Gln Gly Leu Arg Arg Ser Ser
                180                 185                 190

His Val Leu Glu Lys Gly Arg Phe Glu Ser Ser Gly Lys Val Val Asn
            195                 200                 205

Lys Ala Ser Ala Val Val Thr Ser Gln Glu Ser Ile Lys Gln Phe Tyr
    210                 215                 220

Glu Lys Glu Lys Ser Leu Leu Ser Gly Val Lys Phe Trp Arg Leu Ser
```

```
                225                 230                 235                 240
Glu Arg His Cys Arg Phe Ala Leu Val Gly Ile Cys Phe Leu Leu Ala
                    245                 250                 255

Leu Tyr Phe Cys Tyr Val Leu Leu Lys Lys Thr Pro Thr Pro Ala Ser
                    260                 265                 270

Gly Ser Val Val
            275

<210> SEQ ID NO 24
<211> LENGTH: 276
<212> TYPE: PRT
<213> ORGANISM: Human herpesvirus 6B

<400> SEQUENCE: 24

Met Ala Asn Val Leu Lys Glu Lys Met Tyr Asp Glu Leu Leu Ser Ala
1               5                   10                  15

Thr Cys Arg Ile Leu Lys Leu Gly Ser His Asp Tyr Arg Met Thr Glu
                20                  25                  30

Arg Asn Leu Leu Ser Lys Asn Pro Lys Phe Pro Leu Cys Asp Ile Ile
            35                  40                  45

Leu Lys Leu Asp Tyr Ala Tyr Asn Leu Glu Tyr Leu Leu Ser Leu Trp
    50                  55                  60

Glu His Val Thr Lys Gln Glu Pro Arg Phe Val Phe Lys Asn Thr Gly
65                  70                  75                  80

Gly Ala Val Ser Met Ser Cys Tyr Leu His Ala Pro Val Lys Ala Glu
                85                  90                  95

Gly His His Ala Val Arg Glu Cys Asn Ile Leu Arg Val Asn Glu Cys
            100                 105                 110

Leu Thr Val Arg Met Ser Asp Ile Val Ala Met Lys Pro Ser Thr Phe
        115                 120                 125

Ala Val Phe Thr Lys Cys Ile Ile Arg Arg Asn Arg Asp Glu Thr Tyr
    130                 135                 140

Val Val Glu Phe Val Ala Phe Gly Pro Glu Asn Glu Ser Glu Tyr Ile
145                 150                 155                 160

Ser Leu Leu Lys Ala Ile Phe Leu Lys Lys Cys Ser Met Gly Lys Gln
                165                 170                 175

His Leu Glu Ser Asn Arg Phe Cys Gln Gly Leu Arg Arg Arg Ser Ser
            180                 185                 190

His Val Leu Glu Lys Gly Gln Leu Gly Ser Ser Gly Glu Ile Ala Asn
        195                 200                 205

Lys Ala Ser Ala Val Val Thr Ser Gln Glu Ser Ile Asn Gln Phe Tyr
    210                 215                 220

Glu Lys Glu Lys Ser Phe Leu Ser Gly Val Lys Phe Ser Arg Leu Ser
225                 230                 235                 240

Glu Arg His Cys Arg Val Ala Ile Val Ser Ile Cys Phe Leu Leu Ala
                    245                 250                 255

Leu Tyr Phe Cys Tyr Val Leu Leu Lys Lys Thr Pro Thr Pro Ala Ser
                    260                 265                 270

Gly Pro Val Val
            275

<210> SEQ ID NO 25
<211> LENGTH: 258
<212> TYPE: PRT
<213> ORGANISM: Human herpesvirus 7
```

```
<400> SEQUENCE: 25

Met Leu Lys Glu Lys Met Tyr Asp Glu Leu Ile Leu Ser Thr Cys Arg
1               5                   10                  15

Val Leu Lys Leu Gly Pro Ala Asp Phe Arg Val Thr Asp Lys Asn Leu
            20                  25                  30

Phe Ser Lys Asn Pro Lys Phe Pro Leu Cys Asp Ile Leu Leu Lys Leu
        35                  40                  45

Asp Phe Ala Tyr Ser Leu Glu Tyr Leu Leu Ser Leu Trp Glu Asp Leu
    50                  55                  60

Thr Lys Gln Glu Ala Arg Phe Ile Phe Lys Asn Thr Gly Gly Ala Val
65                  70                  75                  80

Ser Met Ser Cys Tyr Leu His Ala Pro Ile Lys Gln Glu Ser Gln Asn
                85                  90                  95

Ile Val Lys Glu Cys Asn Ile Leu Asn Val Asn Glu Cys Leu Ser Val
            100                 105                 110

Cys Leu Asn Asp Ile Glu Ala Ile Lys Pro Ser Ser Ser Gly Val Leu
        115                 120                 125

Thr Lys Cys Ile Ile Arg Arg Asn Arg Asp Ala Ala Phe Ile Val Glu
130                 135                 140

Phe Val Ala Phe Gly Pro Glu Ser Glu Ser Glu Tyr Ile Ala Leu Leu
145                 150                 155                 160

Lys Ala Ile Ile Leu Lys Lys Lys Phe Leu Arg Gln Asp Leu Glu
                165                 170                 175

Lys His Arg Ala Ala Arg His Ile Lys Lys Pro Leu Arg Leu Gln Leu
            180                 185                 190

Lys Ser Val Gly Glu Met Thr Ser Phe Arg Ser Ile Asn Tyr Met Gly
        195                 200                 205

Asn Thr Lys Asp Ala Ala Val Phe Pro Val Thr Val Pro Ile Phe Ala
    210                 215                 220

Arg Arg Asn Asn Ile Leu Cys Gly Phe Leu Val Ala Ala Leu Leu Ile
225                 230                 235                 240

Val Cys Tyr Val Ile Phe Lys Glu Phe Ala Leu Ser Ala Asp Phe Ser
                245                 250                 255

Ala Val

<210> SEQ ID NO 26
<211> LENGTH: 336
<212> TYPE: PRT
<213> ORGANISM: Human herpesvirus 4

<400> SEQUENCE: 26

Met Ala Ser Pro Glu Glu Arg Leu Leu Asp Glu Leu Asn Asn Val Ile
1               5                   10                  15

Val Ser Phe Leu Cys Asp Ser Gly Ser Leu Glu Val Glu Arg Cys Ser
            20                  25                  30

Gly Ala His Val Phe Ser Arg Gly Ser Ser Gln Pro Leu Cys Thr Val
        35                  40                  45

Lys Leu Arg His Gly Gln Ile Tyr His Leu Glu Phe Val Tyr Lys Phe
    50                  55                  60

Leu Ala Phe Lys Leu Lys Asn Cys Asn Tyr Pro Ser Ser Pro Val Phe
65                  70                  75                  80

Val Ile Ser Asn Asn Gly Leu Ala Thr Thr Leu Arg Cys Phe Leu His
                85                  90                  95

Glu Pro Ser Gly Leu Arg Ser Gly Gln Ser Gly Pro Cys Leu Gly Leu
```

```
            100                 105                 110
Ser Thr Asp Val Asp Leu Pro Lys Asn Ser Ile Ile Met Leu Gly Gln
            115                 120                 125

Asp Asp Phe Ile Lys Phe Lys Ser Pro Leu Val Phe Pro Ala Glu Leu
            130                 135                 140

Asp Leu Leu Lys Ser Met Val Val Cys Arg Ala Tyr Ile Thr Glu His
145                 150                 155                 160

Arg Thr Thr Met Gln Phe Leu Val Phe Gln Ala Ala Asn Ala Gln Lys
                165                 170                 175

Ala Ser Arg Val Met Asp Met Ile Ser Asp Met Ser Gln Gln Leu Ser
                180                 185                 190

Arg Ser Gly Gln Val Glu Asp Thr Gly Ala Arg Val Thr Gly Gly Gly
                195                 200                 205

Gly Pro Arg Pro Gly Val Thr His Ser Gly Cys Leu Gly Asp Ser His
        210                 215                 220

Val Arg Gly Arg Gly Gly Trp Asp Leu Asp Asn Phe Ser Glu Ala Glu
225                 230                 235                 240

Thr Glu Asp Glu Ala Ser Tyr Ala Pro Trp Arg Asp Lys Asp Ser Trp
                245                 250                 255

Ser Glu Ser Glu Ala Ala Pro Trp Lys Lys Glu Leu Val Arg His Pro
                260                 265                 270

Ile Arg Arg His Arg Thr Arg Glu Thr Arg Arg Met Arg Gly Ser His
                275                 280                 285

Ser Arg Val Glu His Val Pro Pro Glu Thr Arg Glu Thr Val Val Gly
        290                 295                 300

Gly Ala Trp Arg Tyr Ser Trp Arg Ala Thr Pro Tyr Leu Ala Arg Val
305                 310                 315                 320

Leu Ala Val Thr Ala Val Ala Leu Leu Leu Met Phe Leu Arg Trp Thr
                325                 330                 335

<210> SEQ ID NO 27
<211> LENGTH: 271
<212> TYPE: PRT
<213> ORGANISM: Human herpesvirus 8

<400> SEQUENCE: 27

Met Ser Val Val Gly Lys Arg Val Val Asp Glu Leu Cys Arg Val Val
1               5                   10                  15

Ser Ser Tyr Leu Gly Gln Ser Gly Gln Ser Leu Asp Leu Glu Arg Cys
                20                  25                  30

Ile Asp Gly Ala Pro Val Tyr Ala Lys Gly Gly Ala Thr Ala Ile Cys
            35                  40                  45

Thr Val Arg Met Gln His Gly Cys Val Tyr His Leu Glu Phe Val Tyr
        50                  55                  60

Lys Phe Trp Ala His Leu Leu Glu Glu Met His Tyr Pro Phe Ser Pro
65                  70                  75                  80

Cys Phe Val Ile Ser Asn Asn Gly Leu Ser Thr Thr Leu Lys Cys Phe
                85                  90                  95

Leu Cys Arg Pro Ser Asp Ala Val Ser Gln Phe Gly His Val Leu Pro
            100                 105                 110

Val Glu Ser Asp Val Tyr Leu Ala Lys Asn Thr Ser Val Val Leu Gly
            115                 120                 125

Gln Asp Asp Phe Thr Lys Phe Lys Ala Ser Leu Val Phe Ser Lys Asn
        130                 135                 140
```

```
Leu Gly Val Tyr Asn Ser Met Val Ile Cys Arg Thr Tyr Phe Thr Asp
145                 150                 155                 160

Tyr Arg Gln Val Leu Gln Phe Leu Val Val Thr Pro Lys Ser His Lys
            165                 170                 175

Arg Leu Lys Ser Leu Leu Glu Thr Val Tyr Cys Leu Ala Ala Pro Val
        180                 185                 190

Ala Asp Ser Ala Ala Gln Gly Ala Gly Phe Pro Thr Asn Gly Arg
    195                 200                 205

Asp Ala Arg Ala Cys Thr Ser Asp Val Thr Ala Val Tyr Trp Ala Gly
    210                 215                 220

Gln Gly Gly Arg Thr Val Arg Ile Leu Gly Ala Phe Gln Trp Ser Leu
225                 230                 235                 240

Gly Arg Ala Val Ala Leu Val Arg Arg Ser Trp Pro Trp Ile Ser Ala
            245                 250                 255

Gly Ile Ala Phe Leu Cys Leu Gly Leu Val Trp Met Arg Pro Ser
            260                 265                 270

<210> SEQ ID NO 28
<211> LENGTH: 262
<212> TYPE: PRT
<213> ORGANISM: PrV

<400> SEQUENCE: 28

Met Ser Gly Thr Leu Val Gln Arg Leu Lys Leu Ile Leu Ser Gly Gly
1               5                   10                  15

Asn Leu Arg Cys Ser Asp Gly Glu Thr Ala Cys Asp Pro Glu Arg Pro
            20                  25                  30

Pro Thr Arg Cys Val Phe Gln Val His Gly Gln Asp Gly Ser Asn Asp
        35                  40                  45

Thr Phe Pro Leu Glu Tyr Val Leu Arg Leu Met Arg Ser Trp Ala His
    50                  55                  60

Val Pro Cys Asp Pro Tyr Val Arg Val Gln Asn Thr Gly Val Ser Val
65                  70                  75                  80

Leu Phe Gln Gly Phe Phe Arg Pro Ala Asp Ala Pro Leu Ala Ala
            85                  90                  95

Ile Thr Ala Glu His Asn Asn Val Ile Leu Ala Ser Thr His Ser Thr
            100                 105                 110

Gly Met Ser Leu Ser Ala Leu Asp Asp Ile Lys Arg Ala Gly Gly Val
            115                 120                 125

Asp Thr Arg Pro Leu Arg Ala Met Met Ser Val Ser Cys Phe Val Arg
    130                 135                 140

Met Pro Arg Val Gln Leu Ser Phe Arg Phe Met Gly Pro Asp Asp Ala
145                 150                 155                 160

Ser Gln Thr Gln Arg Leu Leu Asp Arg Ala Glu Met Arg Gln Arg Ser
                165                 170                 175

Val Ser Arg Pro Gly Gly Gly Ala Gly Gly Asp Asp Gly Glu Gly
            180                 185                 190

Pro Ser Pro Arg Ala Pro Ile Arg Pro Thr Val Ile Ser Pro Val Pro
    195                 200                 205

Gly His Ala Ala Ala Phe Val Gly Gln Ala Ala Tyr Pro Pro Pro
    210                 215                 220

Ala Arg Phe Pro Ala Ser Leu Leu His Thr Leu Leu Gly Leu Arg Arg
225                 230                 235                 240

Leu Ala Gly Tyr Ala Val Ala Cys Val Thr Gly Ala Leu Ala Ile Val
            245                 250                 255
```

-continued

Ile Ile Leu Asn Met Arg
            260

<210> SEQ ID NO 29
<211> LENGTH: 316
<212> TYPE: PRT
<213> ORGANISM: Mouse cytomegalovirus 1

<400> SEQUENCE: 29

Met Glu Ile Asp Lys Asn Val Gly Ala Asp Leu Ile Ser Asn Thr Arg
1               5                   10                  15

Arg Ile Leu Arg Leu Asp Glu Asn Glu Leu Arg Ile Thr Asp Thr Ala
            20                  25                  30

Leu Ile Cys Lys Asn Pro Asn Tyr Ser Leu Cys Asp Ala Met Leu Thr
        35                  40                  45

Thr Asp Ile Val Tyr Pro Val Glu Tyr Leu Leu Ser Tyr Trp Glu Cys
    50                  55                  60

Arg Ser Gly Arg Thr Ala Cys Phe Val Phe Lys Asn Thr Gly Cys Arg
65                  70                  75                  80

Val Ser Leu Ser Cys Tyr Ile Gly Phe Pro Glu Arg Leu Lys Asp Leu
                85                  90                  95

Lys Arg Val Cys Asp Phe Asn Phe Leu Ser Val Asn Glu Ala Leu Val
            100                 105                 110

Val Thr Leu Ala Asp Ile Glu Arg Ile Lys Pro Cys Asp Lys Gly Val
        115                 120                 125

Leu Thr Asn Cys Val Val Arg Lys Ser Asn Ser Gly Met Ser Tyr Asn
130                 135                 140

Ile Glu Val Val Ala Phe Gly Pro Asp Asn Glu Ala Glu Tyr Gln Ala
145                 150                 155                 160

Leu Leu Arg Asp Ile Tyr Ala Arg Arg Met Thr Ser Val Pro Thr Asp
                165                 170                 175

Cys Gly Ser Leu Ile Cys Arg Arg Ala Arg Cys Leu Ala Ala Ala Pro
            180                 185                 190

Pro Arg Arg Pro Pro Pro Pro Pro Gly Gln Arg Trp Gly Ser
        195                 200                 205

Leu Arg Lys His Gly Pro Val Leu Thr Arg Arg Tyr Ala Gly Gly Gly
    210                 215                 220

Gly Ala Ala Lys Asn Gln Pro Ala Ala Ser Pro Thr Ser Thr Ser
225                 230                 235                 240

Thr Ser Ser Pro Ala Ala Pro Ser Arg Asp Gln Asp Gln Thr Gln Arg
                245                 250                 255

Pro Pro Pro Ala Gly Asp Thr Asn Val Thr Ala Ala Glu Thr Thr Tyr
            260                 265                 270

Ser Glu Arg Thr Ile Ser Phe Leu Thr Arg His Ala Asn Ala Ile His
        275                 280                 285

Cys Ala Leu Ile Leu Ala Ala Ile Ala Leu Val Leu Leu Trp Leu
    290                 295                 300

Leu Tyr Trp His Ala Ala Arg Ser Ala Gly His Pro
305                 310                 315

<210> SEQ ID NO 30
<211> LENGTH: 28
<212> TYPE: PRT
<213> ORGANISM: human herpesvirus 1

<400> SEQUENCE: 30

Arg Tyr Arg Gly Leu Phe Ala Ala Leu Ala Gln Thr Pro Ser Glu Glu
1               5                   10                  15

Ile Ala Ile Val Arg Ser Leu Ser Val Pro Leu Val
            20                  25

<210> SEQ ID NO 31
<211> LENGTH: 28
<212> TYPE: PRT
<213> ORGANISM: human herpesvirus 2

<400> SEQUENCE: 31

Arg Tyr Arg Gly Phe Phe Ala Ala Leu Ala Gln Thr Pro Ser Glu Glu
1               5                   10                  15

Ile Ala Ile Val Arg Ser Leu Ser Val Pro Leu Val
            20                  25

<210> SEQ ID NO 32
<211> LENGTH: 28
<212> TYPE: PRT
<213> ORGANISM: Human herpesvirus 3

<400> SEQUENCE: 32

Val Tyr Arg His Tyr Phe Asn Tyr Ile Ala Arg Ser Pro Pro Glu Glu
1               5                   10                  15

Leu Ala Thr Val Arg Gly Leu Ile Val Pro Ile Ile
            20                  25

<210> SEQ ID NO 33
<211> LENGTH: 28
<212> TYPE: PRT
<213> ORGANISM: Human herpesvirus 6A

<400> SEQUENCE: 33

Lys Leu His Asp Leu His Thr Val Phe Asn Leu Phe Pro Glu Tyr Glu
1               5                   10                  15

Gln Lys Phe Leu Ala Ile Ile Lys Leu Pro Ile Thr
            20                  25

<210> SEQ ID NO 34
<211> LENGTH: 28
<212> TYPE: PRT
<213> ORGANISM: Human herpesvirus 6B

<400> SEQUENCE: 34

Ser Leu Lys Glu Leu His Ser Val Phe Lys Leu Phe Pro Glu Tyr Glu
1               5                   10                  15

Leu Lys Phe Leu Asn Met Met Lys Leu Pro Ile Thr
            20                  25

<210> SEQ ID NO 35
<211> LENGTH: 28
<212> TYPE: PRT
<213> ORGANISM: Human herpesvirus 7

<400> SEQUENCE: 35

Ser Leu Lys Glu Leu His Ser Val Phe Lys Leu Phe Pro Glu Tyr Glu
1               5                   10                  15

Leu Lys Phe Leu Asn Met Met Lys Leu Pro Ile Thr
            20                  25

<210> SEQ ID NO 36

```
<211> LENGTH: 28
<212> TYPE: PRT
<213> ORGANISM: Human herpesvirus 4

<400> SEQUENCE: 36

Ser Leu Arg Asp Phe Phe Arg Gly Ile Ser Ala Asn Phe Glu Leu Gly
1               5                   10                  15

Lys Asp Phe Leu Arg Glu Met Asn Thr Pro Ile His
            20                  25

<210> SEQ ID NO 37
<211> LENGTH: 28
<212> TYPE: PRT
<213> ORGANISM: Human herpesvirus 8

<400> SEQUENCE: 37

Ser Asp Lys Val Phe Phe Ser Ile Leu Ser Arg His Glu Leu Gly
1               5                   10                  15

Val Asp Phe Leu Arg Glu Met Glu Thr Pro Ile Cys
            20                  25

<210> SEQ ID NO 38
<211> LENGTH: 28
<212> TYPE: PRT
<213> ORGANISM: PrV

<400> SEQUENCE: 38

Arg Tyr Ala Pro Tyr Phe Ala Tyr Ala Ala Ala Gln Pro Ser Asp Glu
1               5                   10                  15

Val Thr Thr Val Arg Gly Leu Ser Asn Pro Leu Ile
            20                  25

<210> SEQ ID NO 39
<211> LENGTH: 28
<212> TYPE: PRT
<213> ORGANISM: Mouse cytomegalovirus 1

<400> SEQUENCE: 39

Lys Leu Ser Glu Leu His Asp Val Phe Gln Arg His Pro Asp Leu Glu
1               5                   10                  15

Gln Lys Tyr Leu Lys Ile Met Lys Leu Pro Ile Thr
            20                  25

<210> SEQ ID NO 40
<211> LENGTH: 20
<212> TYPE: PRT
<213> ORGANISM: Artificial Sequence
<220> FEATURE:
<223> OTHER INFORMATION: Sequence for cloning purposes

<400> SEQUENCE: 40

Met Gly Ser Ser His His His His His His Ser Ser Gly Leu Val Pro
1               5                   10                  15

Arg Gly Ser His
            20

<210> SEQ ID NO 41
<211> LENGTH: 8
<212> TYPE: PRT
<213> ORGANISM: Artificial Sequence
<220> FEATURE:
<223> OTHER INFORMATION: Flag peptide

<400> SEQUENCE: 41
```

Asp Tyr Lys Asp Asp Asp Asp Lys
1               5

<210> SEQ ID NO 42
<211> LENGTH: 93
<212> TYPE: DNA
<213> ORGANISM: Artificial Sequence
<220> FEATURE:
<223> OTHER INFORMATION: Cloning sequence

<400> SEQUENCE: 42
taggaattca tgccgtcgcc ggccgacgcg cgcccgcgcc tcacgctgca cgacctgcac    60
gacatcttcc gcgagcaccc cgaactggag ctc                                93

<210> SEQ ID NO 43
<211> LENGTH: 57
<212> TYPE: DNA
<213> ORGANISM: Artificial Sequence
<220> FEATURE:
<223> OTHER INFORMATION: Restriction site for cloning

<400> SEQUENCE: 43
tagctcgagt cacttgtcgt catcgtcttt gtagtcgccg ctggactgac acagctc       57

<210> SEQ ID NO 44
<211> LENGTH: 94
<212> TYPE: DNA
<213> ORGANISM: Artificial Sequence
<220> FEATURE:
<223> OTHER INFORMATION: 5-BFLF2 (aa73) EcoRI

<400> SEQUENCE: 44
taggaattca tgaccagaca tggtgtagac agatcccatt tttcactacg ggacttcttc    60
aggggaatct ctgccaactt tgagctgggc aaag                                94

<210> SEQ ID NO 45
<211> LENGTH: 58
<212> TYPE: DNA
<213> ORGANISM: Artificial Sequence
<220> FEATURE:
<223> OTHER INFORMATION: 3-BFLF2 (aa318)-Flag XhoI

<400> SEQUENCE: 45
tagctcgagt cacttgtcgt catcgtcttt gtagtcctgt ttattttcca aaatgagc      58

<210> SEQ ID NO 46
<211> LENGTH: 63
<212> TYPE: DNA
<213> ORGANISM: Artificial Sequence
<220> FEATURE:
<223> OTHER INFORMATION: 5-UL53 globular(aa88) + BFLF2 Hook(aa95)

<400> SEQUENCE: 46
tttgagctgg gcaaagattt tctgcgtgag atgaacaccc ccatacatgg caaagagtcc    60
atc                                                                  63

<210> SEQ ID NO 47
<211> LENGTH: 94
<212> TYPE: DNA
<213> ORGANISM: Artificial Sequence
<220> FEATURE:
<223> OTHER INFORMATION: 5-BFLF2 Hook(aa95) mit with UL53 Hook(aa50)
      EcoRI

<400> SEQUENCE: 47
taggaattca tgccgtcgcc ggccgacgcg cgcccgcgcc tcacgctgca cgacctgcac    60
gacatcttcc gcgagcactt tgagctgggc aaag    94

<210> SEQ ID NO 48
<211> LENGTH: 93
<212> TYPE: DNA
<213> ORGANISM: Artificial Sequence
<220> FEATURE:
<223> OTHER INFORMATION: 5-UL53 Hook(aa72) with BFLF2 Hook(aa73) EcoRI

<400> SEQUENCE: 48
taggaattca tgaccagaca tggtgtagac agatcccatt tttcactacg ggacttcttc    60
aggggaatct ctgccaaccc cgaactggag ctc    93

<210> SEQ ID NO 49
<211> LENGTH: 67
<212> TYPE: DNA
<213> ORGANISM: Artificial Sequence
<220> FEATURE:
<223> OTHER INFORMATION: 5-BFLF2 globular(aa111) mit with UL53
      Hook(aa72)

<400> SEQUENCE: 49
cccgaactgg agctcaagta ccttaacatg atgaagatgg ccatcacggt ctcagaggcc    60
gtgtttc    67

<210> SEQ ID NO 50
<211> LENGTH: 59
<212> TYPE: DNA
<213> ORGANISM: Artificial Sequence
<220> FEATURE:
<223> OTHER INFORMATION: 5-BFRF1 EcoRI attB1

<400> SEQUENCE: 50
taggaattcg gggacaagtt tgtacaaaaa agcaggctac catggcgagc ccggaagag    59

<210> SEQ ID NO 51
<211> LENGTH: 31
<212> TYPE: DNA
<213> ORGANISM: Artificial Sequence
<220> FEATURE:
<223> OTHER INFORMATION: 3-BFRF1-Linker BamHI

<400> SEQUENCE: 51
tagggatccc ccggtccacc tcagaaacat c    31

<210> SEQ ID NO 52
<211> LENGTH: 37
<212> TYPE: DNA
<213> ORGANISM: Artificial Sequence
<220> FEATURE:
<223> OTHER INFORMATION: 5-BFLF2-Linker BamHI

<400> SEQUENCE: 52
tagggatccg ggagcatggc cccggtcacc ccagatg    37

<210> SEQ ID NO 53
<211> LENGTH: 86
<212> TYPE: DNA
<213> ORGANISM: Artificial Sequence
<220> FEATURE:
<223> OTHER INFORMATION: 3-BFLF2 XbaI attB2-Flag

```
<400> SEQUENCE: 53
tagtctagag gggaccactt tgtacaagaa agctgggttc acttgtcgtc atcgtctttg    60
tagtcctgtt tattttccaa aatgag                                         86

<210> SEQ ID NO 54
<211> LENGTH: 49
<212> TYPE: DNA
<213> ORGANISM: Artificial Sequence
<220> FEATURE:
<223> OTHER INFORMATION: BGLF4 attB1

<400> SEQUENCE: 54
ggggacaagt ttgtacaaaa aagcaggcta ccatggatgt gaatatggc               49

<210> SEQ ID NO 55
<211> LENGTH: 74
<212> TYPE: DNA
<213> ORGANISM: Artificial Sequence
<220> FEATURE:
<223> OTHER INFORMATION: 3-BGLF4 attB2-Flag

<400> SEQUENCE: 55
ggggaccact ttgtacaaga aagctgggtt cacttgtcgt catcgtcttt gtagtctcca   60
cgtcggccat ctgg                                                     74

<210> SEQ ID NO 56
<211> LENGTH: 21
<212> TYPE: DNA
<213> ORGANISM: Artificial Sequence
<220> FEATURE:
<223> OTHER INFORMATION: T7

<400> SEQUENCE: 56
ttaatacgac tcactatagg g                                             21

<210> SEQ ID NO 57
<211> LENGTH: 19
<212> TYPE: DNA
<213> ORGANISM: Artificial Sequence
<220> FEATURE:
<223> OTHER INFORMATION: SP6

<400> SEQUENCE: 57
catttaggtg acactatag                                                19

<210> SEQ ID NO 58
<211> LENGTH: 20
<212> TYPE: DNA
<213> ORGANISM: Artificial Sequence
<220> FEATURE:
<223> OTHER INFORMATION: 5-pInd20seq_pCMV

<400> SEQUENCE: 58
ccatccacgc tgttttgacc                                               20

<210> SEQ ID NO 59
<211> LENGTH: 18
<212> TYPE: DNA
<213> ORGANISM: Artificial Sequence
<220> FEATURE:
<223> OTHER INFORMATION: 5-BFRF1-BFLF2 Seq.

<400> SEQUENCE: 59
actcgtggtc ggaatccg                                                 18
```

<210> SEQ ID NO 60
<211> LENGTH: 17
<212> TYPE: DNA
<213> ORGANISM: Artificial Sequence
<220> FEATURE:
<223> OTHER INFORMATION: 3-pInducer20 Sequencing

<400> SEQUENCE: 60
ttactaagcg tagtctg                                                 17

<210> SEQ ID NO 61
<211> LENGTH: 14
<212> TYPE: PRT
<213> ORGANISM: Human cytomegalovirus
<220> FEATURE:
<221> NAME/KEY: NLS
<222> LOCATION: (1)..(14)
<223> OTHER INFORMATION: Residues 13 to 26 of HCMV pUL53
<220> FEATURE:
<221> NAME/KEY: HCMV-NLS
<222> LOCATION: (1)..(14)
<223> OTHER INFORMATION: Residues 13 to 26 of HCMV pUL53

<400> SEQUENCE: 61

Arg Arg Ser Ala Leu Arg Ser Leu Leu Arg Lys Arg Arg Gln
1               5                   10

<210> SEQ ID NO 62
<211> LENGTH: 21
<212> TYPE: PRT
<213> ORGANISM: Human cytomegalovirus

<400> SEQUENCE: 62

Leu His Asp Leu His Asp Phe Arg Glu His Pro Glu Leu Glu Leu Lys
1               5                   10                  15

Tyr Leu Asn Met Met
            20

<210> SEQ ID NO 63
<211> LENGTH: 31
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: SITE
<222> LOCATION: (30)..(30)
<223> OTHER INFORMATION: 8-amino-3,6-dioxaoctanoic acid
<220> FEATURE:
<221> NAME/KEY: MOD_RES
<222> LOCATION: (31)..(31)
<223> OTHER INFORMATION: AMIDATION
<220> FEATURE:
<221> NAME/KEY: SITE
<222> LOCATION: (31)..(31)
<223> OTHER INFORMATION: biotinylation

<400> SEQUENCE: 63

Leu Thr Leu His Asp Leu His Asp Ile Phe Arg Glu His Pro Glu Leu
1               5                   10                  15

Glu Leu Lys Tyr Leu Asn Met Met Lys Met Ala Ile Thr Xaa Lys
            20                  25                  30

-continued

```
<210> SEQ ID NO 64
<211> LENGTH: 31
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: SITE
<222> LOCATION: (30)..(30)
<223> OTHER INFORMATION: 8-amino-3,6-dioxaoctanoic acid
<220> FEATURE:
<221> NAME/KEY: MOD_RES
<222> LOCATION: (31)..(31)
<223> OTHER INFORMATION: AMIDATION
<220> FEATURE:
<221> NAME/KEY: SITE
<222> LOCATION: (31)..(31)
<223> OTHER INFORMATION: biotinylation

<400> SEQUENCE: 64

Ser His Phe Ser Leu Arg Asp Phe Phe Arg Gly Ile Ser Ala Asn Phe
1               5                  10                  15

Glu Leu Gly Lys Asp Phe Leu Arg Glu Met Asn Thr Pro Xaa Lys
            20                  25                  30

<210> SEQ ID NO 65
<211> LENGTH: 14
<212> TYPE: PRT
<213> ORGANISM: Human cytomegalovirus

<400> SEQUENCE: 65

Arg Arg Ser Ala Leu Arg Ser Leu Leu Arg Lys Arg Arg Gln
1               5                  10

<210> SEQ ID NO 66
<211> LENGTH: 22
<212> TYPE: PRT
<213> ORGANISM: Human cytomegalovirus

<400> SEQUENCE: 66

Leu His Asp Leu His Asp Ile Phe Arg Glu His Pro Glu Leu Glu Leu
1               5                  10                  15

Lys Tyr Leu Asn Met Met
            20

<210> SEQ ID NO 67
<211> LENGTH: 30
<212> TYPE: PRT
<213> ORGANISM: Human cytomegalovirus

<400> SEQUENCE: 67

Leu Thr Leu His Asp Leu His Asp Ile Phe Arg Glu His Pro Glu Leu
1               5                  10                  15

Glu Leu Lys Tyr Leu Asn Met Met Lys Met Ala Ile Thr Gly
            20                  25                  30

<210> SEQ ID NO 68
<211> LENGTH: 33
<212> TYPE: PRT
<213> ORGANISM: Human herpesvirus 4

<400> SEQUENCE: 68

Asp Arg Ser His Phe Ser Leu Arg Asp Phe Phe Arg Gly Ile Ser Ala
```

```
1               5                   10                  15
Asn Phe Glu Leu Gly Lys Asp Phe Leu Arg Glu Met Asn Thr Pro Ile
            20                  25                  30
His

<210> SEQ ID NO 69
<211> LENGTH: 30
<212> TYPE: PRT
<213> ORGANISM: Artificial Sequence
<220> FEATURE:
<223> OTHER INFORMATION: Shared Hook Sequence

<400> SEQUENCE: 69

Phe Tyr Leu Trp Ser Met Phe Ile Ala Ile Met Arg Tyr Phe Glu Leu
1               5                   10                  15

Gly Met Lys Tyr Leu Asn Met Met Met Lys Pro Met Ile Gly
            20                  25                  30
```

METHODS FOR SCREENING AND IDENTIFYING AGENTS THAT INHIBIT OR MODULATE THE NUCLEAR EGRESS COMPLEX OF HERPESVIRUSES

SEQUENCE LISTING

The instant application contains a Sequence Listing which has been submitted electronically in ASCII format and is hereby incorporated by reference in its entirety. Said ASCII copy, created on Aug. 20, 2024, is named A7534WOUS Updated Sequence Listing and is 87.490 bytes in size.

FIELD OF THE INVENTION

This invention relates generally to a field of rational drug design for affecting/inhibiting the formation of the nuclear egress complex (NEC) in viruses of the family of Herpesviridae, particularly human cytomegalovirus (HCMV), Epstein-Barr virus (EBV), and/or varicella zoster virus (VZV).

Specifically, the present invention relates to methods for screening inhibitors of general protein-target or peptide-target interactions including, but not limited thereto, protein-protein, protein fragment-protein fragment, peptide-peptide, peptide fragment-peptide fragment, protein-nucleic acid, protein-peptide, and protein-small-molecule interactions as well as peptide-small-molecule interactions, but not limited thereto, with particular application to the inhibition of the interaction of the core NEC proteins pUL50 and pUL53 or homologues thereof of the NEC of viruses of the group of Herpesviridae, and particularly in cytomegalovirus, more particularly in human cytomegalovirus (HCMV), and/or BFRF1 and/or BFLF2 or homologues thereof of EBV, and/or open reading frame 24 (ORF24) and or open reading frame 27 (ORF27) or homologues thereof of VZV.

Previously, it was challenging to gather sufficient information about the structure of the NEC complex. Attempts to elucidate the crystal structure of these complexes did not provide sufficiently clear results so that these could be used in bioinformatics methods for the design and identification of molecules interacting, and particularly affecting or inhibiting the formation of the NEC in herpesviruses, with the exception of HCMV, where information was available, albeit not sufficient for use for the above purposes.

Fusion proteins are provided herein that comprise the respective subunits of the NEC, advantageously permitting to provide improved structural data of the NECs of respective viruses will help identifying drugs that interact with at least one of these NECs, but preferably with more of the NECs of different herpesviruses.

Hage, S. B., "Analysis of the functional conservation of herpesviral core NEC proteins", master thesis, April 2018, shows that the protein subunits of the NEC derived from different members of the herpesvirus family do not tend to co-precipitate, i.e. they do not form functional heterodimers, with the exception of protein subunits derived from human and mouse CMVs. For example, heterodimers between protein subunits derived from HCMV and EBV could not be co-immunoprecipitated. This led to the assumption that the respective subunits of different herpesviruses are structurally quite dissimilar. However, due to the use of the herein described new fusion proteins, it was surprisingly possible to determine that crystal structures of unrelated herpesviruses are quite similar. This suggests also similar functions, which may be modulated and/or inhibited by compounds that are also quite similar for more than one virus type.

Accordingly, the herein described structures provide the basis for the establishment of methods using the fusion proteins as tools to identify those compounds, which interact with at least one herpesvirus of the Herpesviridae, i.e. HHV-1 to HHV-8, MCMV and/or PrV, particularly with different herpesviruses, e.g., those belonging to different herpesvirus subgroups, for example with the betaherpesviruses.

Accordingly, the present invention relates particularly to methods for screening agents capable of modulating/inhibiting the activity of the protein-protein and/or peptide-protein interactions of BFRF1 and/or BFLF2 or homologues thereof of EBV, and/or open reading frame 24 (ORF24) and or open reading frame 27 (ORF27) or homologues thereof of VZV, and/or HCMV pUL50 and pUL53 or homologues thereof, based on a novel N-terminal hook mechanism of pUL53 or a homologue thereof that is extendable to homologue NEC mechanisms of viruses of the group of Herpesviridae, such as in the species HHV-1 to HHV-8 and/or PrV, but not limited thereto, and particularly in human cytomegalovirus (HCMV), EBV and/or VZV, or with betaherpesviruses.

In this connection, FIG. 4 shows highly conserved respective regions of the CR1-CR of among specific strains of the group of Herpesviridae species HCMV, MCMV, HSV, HHV-6, VZV, EBV, and PrV. It is reasonable to assume that a high degree of homology of highly conserved protein regions provides for functional protein or peptide motives that may be exploited in screening technologies to find novel antiviral drugs based on the functional protein or peptide motives as unique target, e.g., a (pan-) anti-herpesvirus drug.

Previously an N-terminal 29aa hook structure of pUL53 was described (Walzer et al, J. Biol. Chem. Vol 290, No. 46, pp. 27452-27458) as target structure. Another key finding was the determination of specific amino acid based phosphosites of pUL50 that are positioned outside the pUL50-pUL53 interacting region, and are decisive for phosphorylation during NEC-based mechanisms, i.e. the NEC multimerization.

The present invention provides tools and methods to identify molecules/agents/compounds that mask, block or shield said specific aa-based phospho-sites to affect/modulate/inhibit the phospho-sites either alone or in combination to influence structure and/or function of the viral NEC multimerization within the group of Herpesviridae, such as in species selected from a group HHV-1 to HHV-8, MCMV and/or PrV. This may be also exploited in novel antiviral strategies thereof.

BACKGROUND OF THE INVENTION

Protein-protein or peptide-protein or peptide-peptide interactions have a key role in most biological processes including the nuclear egress of packaged capsids to promote further virion maturation, and thus offer attractive opportunities for therapeutic intervention.

Different kinds of protein-protein or peptide-protein or peptide-peptide interactions may be inhibited using drug-like small molecules/in silico designed small molecules/proteins/protein fragments/peptides/peptide fragments/antibodies/non-IgG scaffolds etc.

Within the family of Herpesviridae, and specifically for HCMV, the human prototype member of said family, the viral NEC represents a regulatory key position of viral replication and a putative target for novel antiviral strategies (4-9). According to the present invention, the viral NEC is not only a target for HCMV, but also for EBV and VZV, and highly likely also for other herpesviruses.

As a characteristic feature of most DNA viruses, HCMV starts genomic replication in the host cell nucleus, where preformed capsids are packaged and exported to the cytoplasm for further virion maturation. The transition of capsids through the nuclear envelope (i.e. nuclear egress) is a multistep regulatory process that involves a phosphorylation-triggered distortion of the nuclear lamina (10-17). The HCMV-encoded protein kinase pUL97 was identified as the first herpesviral kinase with lamin-phosphorylating activity (11, 16, 17; see FIG. 6).

Importantly, the recruitment of lamina-phosphorylating viral and cellular kinases as well as further lamina-modifying host factors (such as prolyl cis/trans isomerase Pin1; (13)) is accomplished by two conserved viral nuclear egress proteins, pUL50 and pUL53. As an essential step in HCMV replication, pUL50 and pUL53 hetero-dimerize and form the core of the NEC that serves as a scaffold for the recruitment of a group of viral and cellular NEC-associated proteins (see FIGS. 3 and 6). The composition of the multimeric NEC of human and murine cytomegaloviruses (CMVs) has recently been defined by proteomic analyses (15, 18).

Furthermore, both nuclear egress proteins pUL50 and pUL53 are post-translationally modified in a complex manner, in particular by phosphorylation. The viral kinase pUL97 is one of the responsible kinases, but cellular kinases are suggested being involved in viral core NEC phosphorylation, as well. The correctly phosphorylated state of pUL50 and pUL53 is important for its protein activity, intracellular transport, and interaction with each other and with other viral and cellular NEC proteins, as well as for protein stability.

Human cytomegalovirus (HCMV, family Herpesviridae) is a major human pathogen showing a worldwide distribution. Its clinical importance has occasionally been underestimated, as infection of the immunocompetent host may be limited to mild forms of symptoms (1). The main pathogenesis of HCMV is manifested by severe systemic or even life-threatening disease in immunosuppressed hosts and upon congenital infection of neonates (2, 3). HCMV pathogenesis is determined by various parameters of immune control, viral productivity, viremia, tissue tropism and organ damage, as well as manifold regulatory events of virus-host interaction (1).

Hence, the viral productive replication cycle is largely co-regulated by the interaction between viral and cellular proteins and by the formation of virus-host multiprotein complexes. Thereby, the NEC represents a regulatory key position of viral replication and a putative target for novel antiviral strategies (4-9).

There is, therefore, a continuing need for an effective and simple method to identify compounds (preferably drug-like small molecules) that can interfere in such protein-protein/peptide, protein-nucleic acid, and protein-small signaling molecule interactions etc. that play critical roles in macromolecular recognition.

In particular, there is a continuing need for an effective and simple method to identify compounds that can interact with such essential proteins, such as BFRF1 and BFLF2 of EBV, and/or ORF24 and ORF27 of VZV, and/or pUL50 and pUL53 of HCMV, and its homologues, and thereby can be used in development of tailored therapeutics to suppress virion maturation more efficiently and more specifically. However, the development of drugs that inhibit the NEC scaffolding has so far progressed slowly.

Thus, there is a need for a deeper understanding of the decisive components of the formulation of NEC and its resultant pathways. Accordingly, newly discovered components of the NEC, which appear to be highly conserved in viruses comprising a nuclear egress complex-based mechanism for transfer of the packaged viral capsids from nucleus to cytoplasm, can then serve as novel targets for tailored drug-designs.

It is known that particularly among the viral group of Herpesviridae, such as HHV-1 to HHV-8, MCMV and/or PrV, for example, the betaherpesviruses, but not limited thereto, the nuclear egress complex-based mechanism for transfer of the DNA-packaged viral capsids from nucleus to cytoplasm plays a pivotal role in virion maturation, and thus appears as promising drug-target for broad-spectrum pharmaceutical agents.

In view of the above-described problems, needs, and goals the inventors have devised embodiments of the present invention in which modulators/inhibitors of protein interactions (protein-protein, peptide-peptide, protein-nucleic acid, protein-small molecule etc.) can be effectively identified based on novel screening methods that relies on the herein disclosed structures of the NEC, (see the FIGS. 1 and 2 for an illustration of the hook-like structure of HCMV and for steric details) between the pUL50 and pUL53 interaction during nuclear egress.

SUMMARY OF THE INVENTION

Nuclear replication of herpesvirus in general, and specifically of EBV and/or VZV and/or cytomegalovirus, relies on elaborate mechanisms of nucleocytoplasmic egress of viral particles; i.e. viral DNA packaged in capsids that are transferred from the nucleus of a host cell into the cytoplasm. Hereby, two types of proteins are highly conserved and essential for building the core of a nuclear egress complex among viruses of the group of Herpesviridae (see e.g. the FIG. 4 and the SEQ ID NOS: 7-39). Specifically, the role of two essential and conserved viral nuclear egress proteins pUL50 and pUL53 is pivotal for cytomegalovirus, particularly for HCMV. Said pUL50 and pUL53 hetero-dimerize and form the core nuclear egress complex (NEC), which is anchored to the inner nuclear membrane and provides a scaffold for the assembly of a multimeric viral-cellular NEC (see FIG. 3 for illustration thereof). Corresponding proteins are, for example, BFRF1 and BFLF2 of EBV, and ORF24 and ORF27 of VZV, respectively.

In the present invention, the inventors disclose the detailed crystal structure of the EBV and HCMV core NEC as well as the BFRF1 and BFLF2 and pUL50 and pUL53 protein-protein interaction mechanism, respectively, based on new and truncated fusion proteins as depicted in SEQ ID NOs: 1-6.

The conserved proteins pUL50 and pUL53 of cytomegalovirus, BFRF1 and BFLF2 of EBV, and ORF24 and ORF27 of VZV hetero-dimerize and form a core nuclear egress complex. Functionally relevant fragments thereof, i.e. pUL50 and pUL53, BFRF1 and BFLF2 of EBV, and ORF24 and ORF27 of VZV were coproduced in *E. coli*, co-purified and co-crystallized to determine the three-dimensional structure at high resolution.

Implications for the detailed assembly of the multimeric NEC are disclosed as well in view of the observed hook interaction between pUL53 and pUL50 (see FIGS. 1 and 2) and the disclosed larger assembly of pUL50-pUL53 heterodimers into hexameric ring-like structures within the crystals (see FIG. 2 C for illustration thereof and for steric details).

The inventors previously found that the hook interaction of the essential proteins pUL50 and pUL53 is a promising target for the development of novel antiviral strategies e.g. against CMV in general and HCMV specifically, and due to the high degree in analogy and homology against other viruses of the of the group of Herpesviridae, in general (see the alignment information in FIG. 4 and the sequences SEQ ID NOs: 7-39 for sequence details in respect to homology).

New therapeutic strategies could aim at a direct steric inhibition of protein-protein, peptide-peptide interactions via e.g. in silico designed small molecule inhibitors, and/or at an interference with regulatory mechanisms that control NEC assembly, as the inhibition of NEC protein phosphorylation through kinase inhibitors on specifically herein disclosed amino acid phosphorylation sites (6, 43; see further below).

The inventors found that the crystalline structural information disclosed herein, for example for the HCMV pUL50-pUL53 complex or for the EBV BFRF1-BFLF2 complex, may be used as the basis of new approaches in screening methods for agents that inhibit NEC as a unique (Pan-) anti-herpesviral target, for example for EBV and/or VZV and/or HCMV replication inhibition. In one particular aspect of the invention, the herein described compounds are for use in the inhibition of the NEC in betaherpesviruses. Accordingly, the screening methods disclosed within the context of the invention allow for the development of novel types of NEC-targeted drugs for viruses selected from the group of Herpesviridae, specifically for Pan-Herpes drugs.

Such screening methods may generally comprise the steps of:
  (a) providing at least one infected cell with at least one virus of the Herpesviridae, characterized in that said cell(s) expresses BFRF1 and/or BFLF2 of EBV or a functional homologue thereof, and ORF24 and/or ORF27 of VZV or a functional homologue thereof, or a pUL50 and/or pUL53 or a functional homologue thereof,
  (b) contacting said cell(s) with a candidate agent to be tested,
  (c) and determining whether the candidate agent prevents/inhibits the nuclear egress of said virus(es) into the cytoplasm.

Another method of screening for agents that modulate/inhibit the activity of the BFRF1 and BFLF2, and/or ORF24 and ORF27 and/or pUL50 and pUL53 interaction comprises the steps of:
  (a) providing an in vitro sample, characterized in that said sample comprises at least one BFRF1 and/or BFLF2 and/or ORF24 and/or ORF27 and/or pUL50 and/or pUL53 protein(s) or functional homologue(s) thereof,
  (b) contacting said in vitro sample with a candidate agent to be tested, and
  (c) determining whether the candidate agent prevents/inhibits the respective protein interaction.

The conserved cytomegalovirus proteins BFRF1 and BFLF2, or ORF24 and ORF27, or pUL50 and pUL53 hetero-dimerize and form a core of the nuclear egress complex (NEC). The inventors solved the crystal structure of the protein complexes of the herein provided new fusion proteins at 1.48 Å resolution for HCMV pUL50 and pUL53 and at 1.75 Å resolution for EBV BFRF1 and BFLF2.

The inventors previously found an N-terminal hook extension of pUL53, i.e. based on the primary structure of the peptide according to SEQ ID NO: 7 of the pUL53 sequence as being the core NEC architecture, which provides for a scaffold for viral-cellular NEC protein interactions and for building the multimeric NEC.

The resultant secondary, tertiary, and quaternary structures of the viruses proteins may serve as targets for development of novel antiviral strategies, which may hinder the nuclear egress of DNA-packaged capsids from nucleus to cytoplasm, and thus may be useful against viruses of the group of Herpesviridae in general, and particularly among the species HHV-1 to HHV-8, MCMV and PrV, for example for the betaherpesviruses, but not limited thereto, wherein the nuclear egress complex-based mechanism for transfer of the DNA-packaged viral capsids from nucleus to cytoplasm plays a pivotal role in virion maturation.

With this approach, on the basis of new data on the crystal structures of the EBV, VZV and human cytomegalovirus nuclear egress complexes the inventors provide new approaches for tailored screening methods for agents which specifically exploit this mechanism.

BRIEF DESCRIPTION OF THE FIGURES/DRAWINGS

FIG. 1: Crystal structure of the pUL50-pUL53 complex.

FIG. 1A: Ribbon representation of the pUL50-pUL53 complex. pUL50 is shown in the section below; pUL53 is shown in the section above. The secondary structure elements of the hook-like N-terminal extension of pUL53 (based on the SEQ ID NO: 7) are marked $\alpha_{53}1$, $\alpha_{53}2$ and $\beta_{53}1$.

FIG. 1B: Display of a portion of the phased anomalous difference electron density map that validates the location of the methionine residues in the final model. The map is displayed at a 5 sigma cut-off and is calculated with the anomalous differences observed in the SeMet peak dataset.

FIG. 1C: Close-up view of the zinc-binding site of pUL53 protein.

FIG. 1D: Detailed representation of the interaction of the hook-like N-terminal extension of pUL53 with pUL50; shown in two different orientations. Residues displayed in a stick representation contribute in excess of 50 Å$^2$ of their surface area to the interaction.

FIG. 2: Implications of the pUL50-pUL53 crystal structure.

FIG. 2A: HCMV pUL53 shows a structural resemblance to the GHKL domain, as depicted by an overlay of pUL53 (the large surrounding ribbons) and the GHKL domain from *Staphylococcus aureus* VraS (the central ribbons in the upper portion of FIG. 2A; PDB code 4GT8). The ADP molecule bound to the VraS protein is shown in sticks in the center of FIG. 2A. The zinc ion bound to pUL53 is depicted as sphere in the center of FIG. 2A. The search for structural homologues and the overlay was performed with PDBeFold (36).

FIG. 2B: Superposition of the crystal structure of pUL50 and the NMR structure of pM50 (pdb 5A3G) (9). pUL50, pUL53 and pM50 are shown, respectively. In comparison to the structure of pM50, the C-terminal helix of pUL50 is displaced by helices $\alpha_{53}1$ and $\alpha_{53}2$ from pUL53 that form a hook-like extension.

FIG. 2C: Hexameric ring-like structure formed by the pUL50-pUL53 complex in the crystals. Ribbon and surface representations of pUL50 and pUL53 are shown, respectively. While the pUL50 molecules form a contiguous ring, the pUL53 molecules are displayed individually form the rim of the ring. The locations of the protein termini are marked with black dots.

Figure 3:
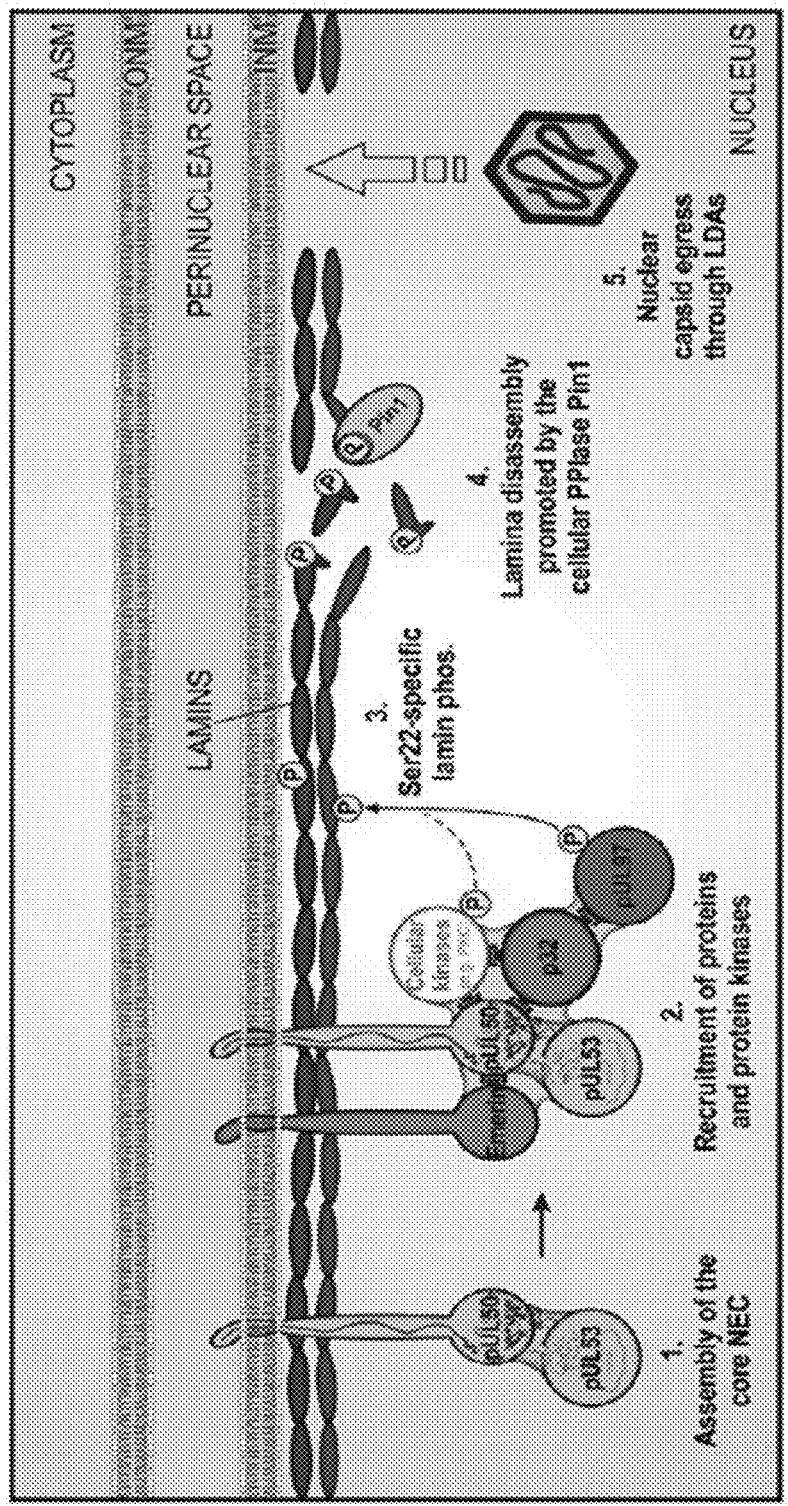

FIG. 3: Schematic illustration of the nuclear egress of HCMV-sequential steps of NEC protein recruitment and nuclear lamina-reorganizing enzymatic activities. HCMV genomic replication leads to the nuclear accumulation of packaged viral capsids which are subject to sequential steps of nucleocytoplasmic export by traversing the nuclear envelope (nuclear lamina, inner and outer nuclear membranes INM/ONM and perinuclear space). A rearrangement of the nuclear lamina leads to the formation of lamina-depleted areas (LDAs) serving as preformed sites of nuclear egress. The nuclear egress complex (NEC) is assembled by the association of a recently defined group of viral and cellular NEC components (including pUL50-pUL53, p32/gC1qR, emerin, pUL97, PKCα/cellular kinases, Pin1 and further putative NEC candidates (12, 13, 14, 15). Importantly, the core NEC is formed by the heterodimer pUL50-pUL53 (step 1) that subsequently recruits other constituents of the multimeric NEC through direct or indirect interactions (step 2). The recruitment function may primarily fulfilled by pUL50 that proved to possess multi-protein binding activity (direct binding of pUL53, p32/gC1qR, emerin and PKCα). Lamina disassembly is triggered by the site-specific lamin A/C-phosphorylating properties of pUL97 and cellular protein kinases (step 3) (6, 10, 11, 16, 17). The cellular peptidyl-prolyl cis/trans isomerase (PPIase) Pin1 is a downstream effector that specifically binds and possibly isomerizes phosphorylated nuclear lamins (step 4). As a consequence, a locally restricted distortion of the nuclear lamina in the form of LDAs is detectable by imaging techniques (13). These LDAs are finally used by viral capsids for nuclear egress (step 5). Thus, efficient nuclear egress is dependent on a functional core NEC, recruitment of lamin-phosporylating kinase activities and the formation of LDAs.

Protein sequence alignment of pUL50 and pUL53 homologues within the context of the invention. Using the ClustalW algorithm (Thompson et al., 1994) by AlignX (component of Vector NTI Advance 9.1.0; Invitrogen), multiple alignments of the full amino acid sequences of pUL53 (FIG. 4A) and pUL50 (FIG. 4B) homologues of human herpesviruses (herpes simplex virus type 1 and 2, HSV-1/-2; varicella zoster virus, VZV; human cytomegalovirus, HCMV; human herpesvirus 6 variant A and B, HHV-6A/B; human herpesvirus 7, HHV-7; Epstein-Barr virus, EBV; and human herpesvirus 8, HHV-8) and animal herpesviruses (Pseudorabies virus, PrV, and mouse cytomegalovirus, MCMV) were performed. The sequences were selected from the UniProt Knowledgbase.

Alignment labelling scheme of FIG. 4—boxed and marked with subscript letter X, identical residues throughout all analyzed sequences; boxed and marked with subscript letter Z, identical residues in all sequences of human herpesviruses; grey marking, identical residues in all sequences of betaherpesviruses (HCMV, HHV-6A/B, HHV-7, and MCMV). Sequences of the hook structure in homologues of pUL53 and the previously identified conserved regions within homologues of pUL53 (CR1 to CR4) and pUL50 (CR1 and CR2) (Lotzerich et al., 2006; Milbradt et al., 2012) are depicted above the sequence alignment as gray and black bars, respectively. Residues of pUL50 and pUL53 which interact with the other protein are marked by #; residues of pUL53 which constitute a zinc finger are marked by *. It is noted that almost all residues of the interaction surface are located within the conserved regions (pUL53, only CR1; pUL50, CR1 and CR2); the residues of the zinc finger (Cys106, Cys122, Cys125, His211) are strictly conserved among pUL53 sequences.

FIG. 4A: pUL53 homologues-UL31 of HSV-1 strain 17 (accession number P10215), UL31 of HSV-2 strain HG52 (P89454), ORF27 of VZV strain Dumas (P09283), pUL53 of HCMV strain AD169 (P16794), U37 of HHV-6A strain Uganda (P28865), U37 of HHV-6B strain HST (Q9WT27), U37 of HHV-7 strain JI (P52361), BFLF2 of EBV strain B95-8 (PoCK47), ORF67 of HHV-8 strain GK18 (F5H982), UL34 of PrV strain Kaplan (Q911V7), and pM53 of MCMV (H2A291).

HCMV pUL53 (SEQ ID NO. 8)
HSV-1 UL31 (SEQ ID NO. 10)
HSV-2 UL31 (SEQ ID NO. 11)
VZV orf27 (SEQ ID NO. 12)
HHV-6A UL37 (SEQ ID NO. 13)
HHV-6B U37 (SEQ ID NO. 14) *
HHV-7 UL37 (SEQ ID NO. 15) *
EBV BFLF2 (SEQ ID NO. 16)
HHV-8 ORF69 (SEQ ID NO. 17)
PrV UL31 (SEQ ID NO. 18) *
MCMV pM53 (SEQ ID NO. 19)

FIG. 4B: pUL50 homologues-UL34 of HSV-1 strain 17 (P10218), UL34 of HSV-2 strain HG52 (P89457), ORF24 of VZV strain Dumas (P09280), pUL50 of HCMV strain AD169 (P16791), U34 of HHV-6A strain Uganda (P52465), U34 of HHV-6B strain Z29 (Q9QJ35), U34 of HHV-7 strain JI (P52466), BFRF1 of EBV strain B95-8 (PO3185), ORF67 of HHV-8 strain GK18 (Q76RF3), UL34 of PrV strain Kaplan (Q9ICS7), and pM50 of MCMV (H2A365).

HCMV pUL50 (SEQ ID NO. 9)
HSV-1 UL34 (SEQ ID NO. 20)
HSV-2 UL34 (SEQ ID NO. 21)
VZV ORF24 (SEQ ID NO. 22)
HHV-6A U34 (SEQ ID NO. 23)
HHV-6B U34 (SEQ ID NO. 24)
HHV-7 U34 (SEQ ID NO. 25)
EBV BFRF1 (SEQ ID NO. 26)
HHV-8 ORF67 (SEQ ID NO. 27)
PrV UL34 (SEQ ID NO. 28)
MCMV pM50 (SEQ ID NO. 29)

Figure 5:
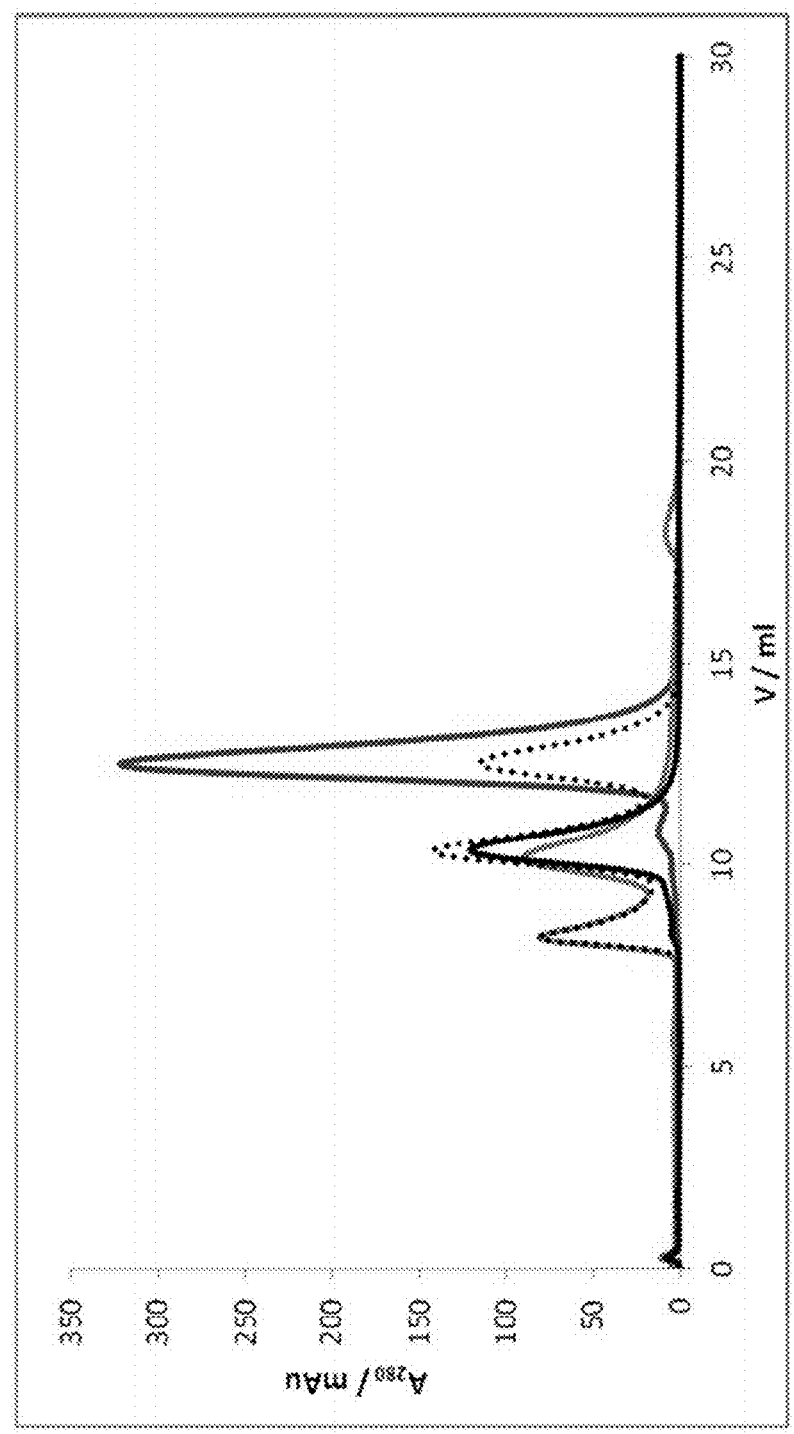

FIG. 5: Analytical size exclusion chromatography illustrating the oligomerization of pUL50 (1-181) and pUL53 (50-292). The constructs were analyzed using a Superdex 75 10/300 column (GE Healthcare). pUL50 (1-181) produced singularly (see highest peak in the center of FIG. 5)-pUL50 was determined to be monomeric in solution, with molecular weight (MW) of 20.3 kDa, in agreement with its calculated MW of 20.3 kDA. pUL53 (50-292) produced singularly (see the two smallest peaks in FIG. 5)-pUL53 showed two distinct peaks in the chromatogram: a later peak at a MW of 55.6 kDA, consistent with the MW of pUL53 (50-292) homodimer (calculated MW 56.8 kDa), and an earlier peak eluting in the column's void volume representing higher oligomeric states. pUL50 (1-181) and pUL53 (50-292) coproduced (see black solid line with one peak of intermediate height in the center of FIG. 5)-when coproduced and co-purified from E. coli, both proteins eluted as a heterodimer at a MW of 48.1 kDa (calculated MW 48.7 kDa). pUL50 (1-181) and pUL53 (50-292) mixed (see black broken line with three peaks in FIG. 5)-when produced and purified separately, then mixed in vitro, the elution profile showed three distinct peaks: the earliest peak is consistent with the higher oligomeric state of pUL53 (50-292) eluting in the void volume, the middle peak is identical with the heterodimeric pUL50-pUL53 when coproduced and co-purified, the late peak is consistent with monomeric pUL50 (1-181). The behavior of pUL50 and pUL53 described here closely mirrors the behavior observed by Sam et al. (38).

Figure 6:
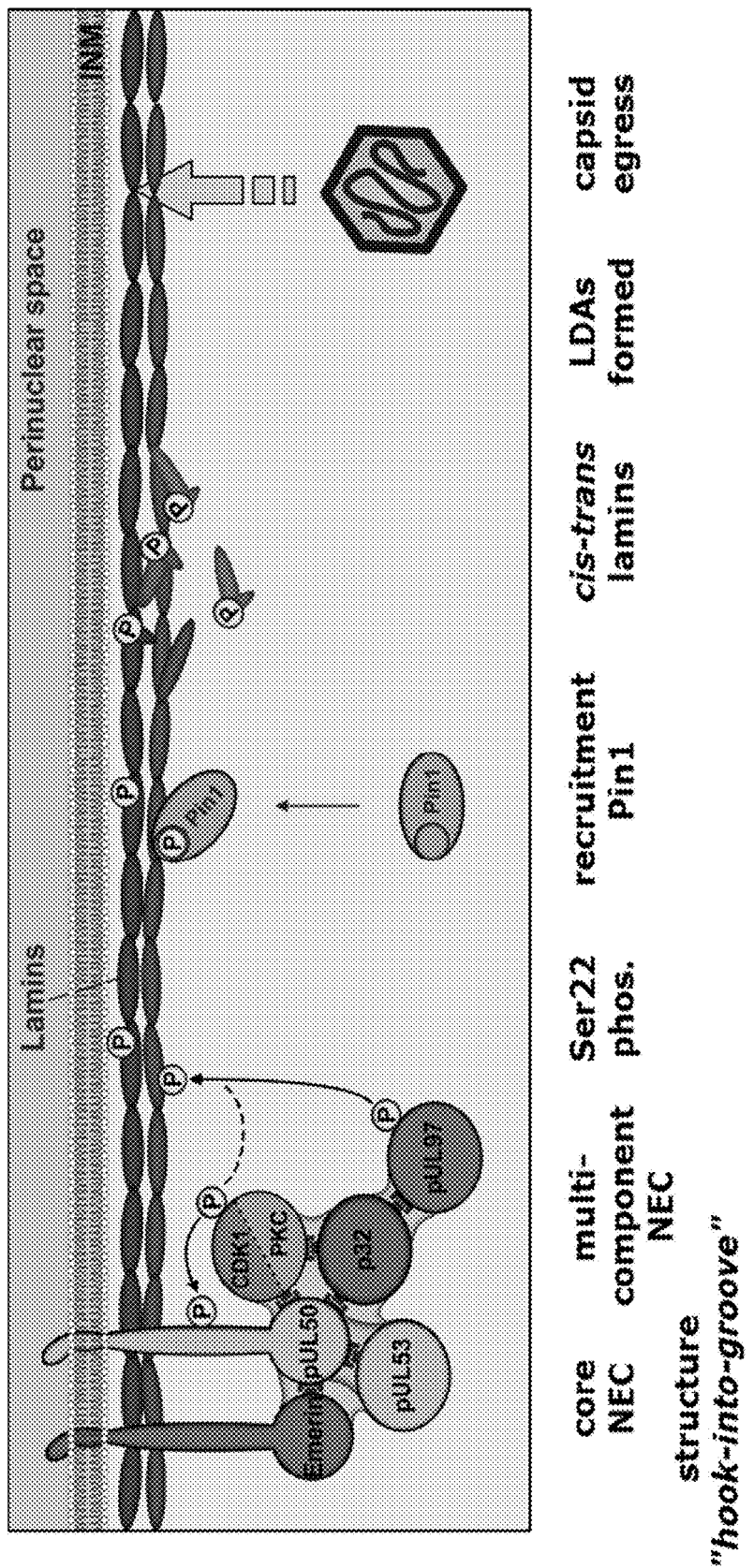

FIG. 6: Schematic illustration of the multimeric NEC of HCMV.

Figure 7:
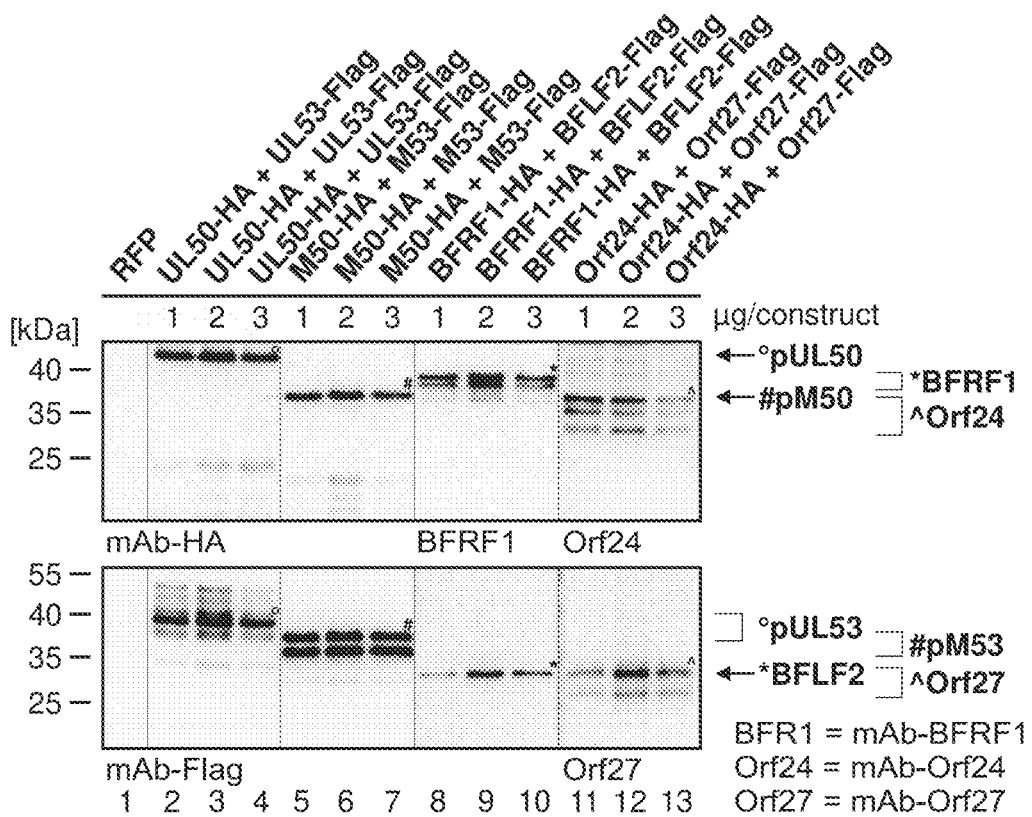

FIG. 7: Expression analysis of the core NEC proteins of HCMV, MCMV, EBV and VZV. 293T cells were transiently co-transfected with constructs coding for HA-tagged pUL50, pM50, BFRF1, Orf24 or Flag-tagged pUL53, pM53, BFLF2 and Orf27 with indicated concentrations (1, 2 or 3 μg per construct) in the respective combination, or with pDsRed1-N1 (RFP) as a control. At three dpt, cells were harvested and lysed. Samples were subjected to standard Wb analysis using tag-specific or protein-specific monoclonal antibodies as indicated.

Figure 8:
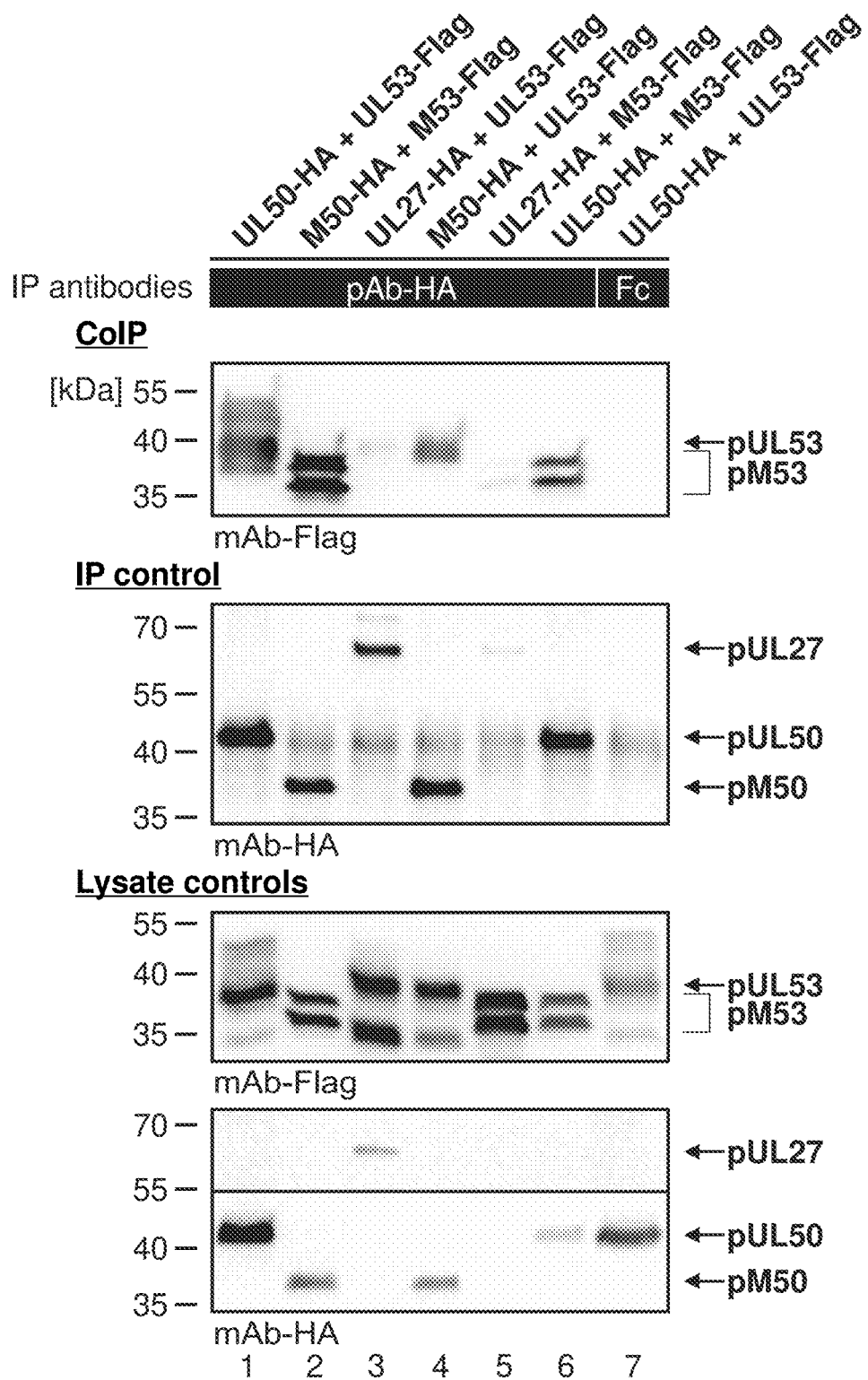

FIG. 8: Interaction analysis of β-herpesviral core NEC proteins. 293T cells were transiently transfected with constructs coding for HA-tagged pUL50, pM50 or pUL27 (negative control) in combination with pUL53 or pM53. At three dpt, cells were lysed and HA-tagged proteins were precipitated using pAb-HA or a rabbit antibody Fc fragment as specificity control. Lysate controls taken prior to the IP and CoIP samples were subjected to standard Wb analysis using tag-specific antibodies as indicated.

FIG. 9A: Structural elements of pUL53, crystal structure of the HCMV core NEC and schematic composition of domain swap constructs. Illustration of the HCMV pUL53 with structural elements, the conserved regions and functional domains. The amino acids 50-84 (dashed box) of pUL53 are required for interaction with pUL50 and form the hook structure (Sam et al., 2009). The main portion of globular domain (black box) is located in the central part of pUL53 and contains four conserved regions (CR1-4) (modified from Milbradt et al., 2012).

SEQ ID No: 65-RRSALRSLLRKRRQ
SEQ ID No: 66-LHDLHDIFREHPELELKYLNMM

FIG. 9B Crystal structure of the pUL50-pUL53 heterodimer. The hook-like N-terminal extension of pUL53 is additionally depicted in a 90° rotated view (modified from Walzer et al., 2015).

FIG. 9C Schematic representation of the domain swap constructs generated between pUL53 (black) and BFLF2 (grey). The numbers represent the amino acid positions.

Figure 10:
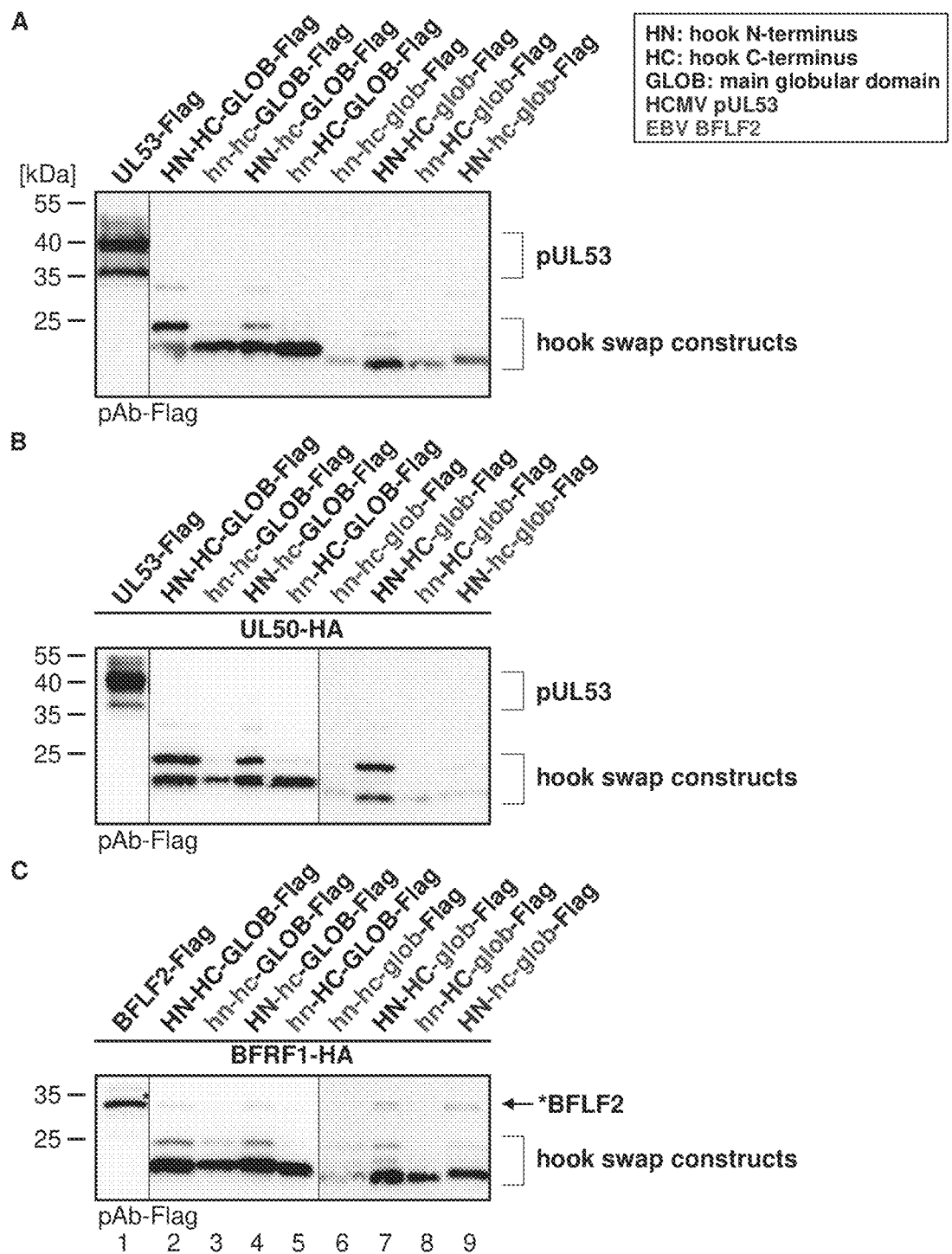

FIG. 10: Expression pattern of the generated domain swap constructs. (A-C) 293T cells were transiently transfected with domain swap constructs. Core NEC proteins (B) pUL50-HA or (C) BFRF1-HA were cotransfected. Specificity of transfections were assured by (A and B) pUL53-Flag or (C) BFLF2-Flag. At two dpt, cells were harvested and lysed. The samples were subjected to standard Wb analysis using pAb-Flag.

Figure 11:
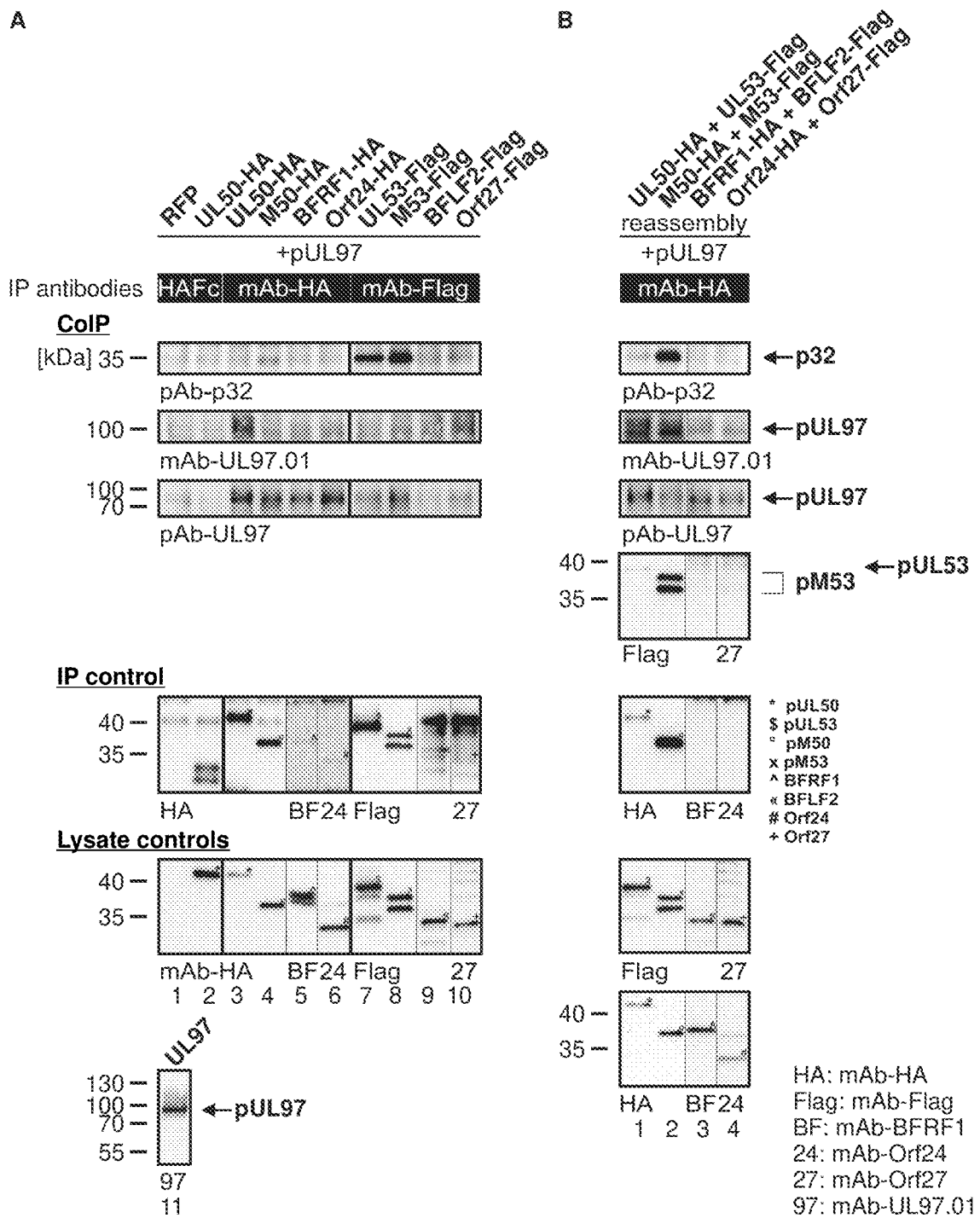

FIG. 11: Recruitment of pUL97 by herpesviral core NEC proteins. 293T cells were transiently transfected with HA-tagged pUL50, pM50, BFRF1, Orf24; Flag-tagged pUL53, pM53, BFLF2, Orf27; pUL97 or RFP (negative control). At three dpt, cells were lysed and for reassembly lysates were mixed and incubated at 4° overnight (B). HA- or Flag-tagged proteins were immunoprecipitated using mAb-HA or mAb-Flag and incubated with the pUL97-lysate for 3 h. Lysate controls taken prior to the IP and CoIP samples were subjected to standard Wb analysis using tag- and protein-specific antibodies as indicated.

Figure 12:
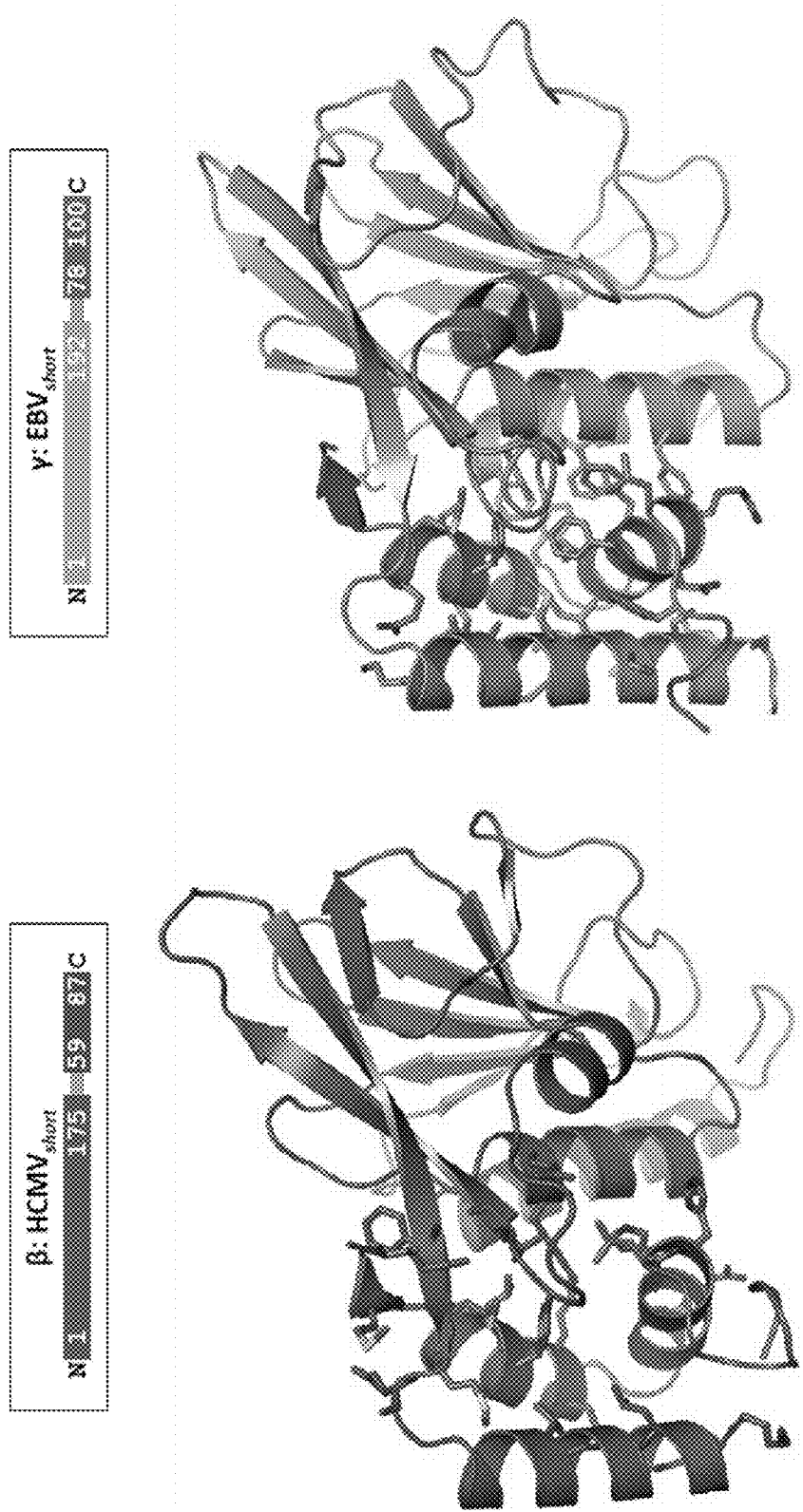

FIG. 12: Comparison of the hook-into-groove interface. The two structures of HCMV and EBV NEC proteins were obtained using versions of fusion polypeptides of shortened HCMV NEC proteins and of EBV NEC proteins, respectively.

Figure 13:
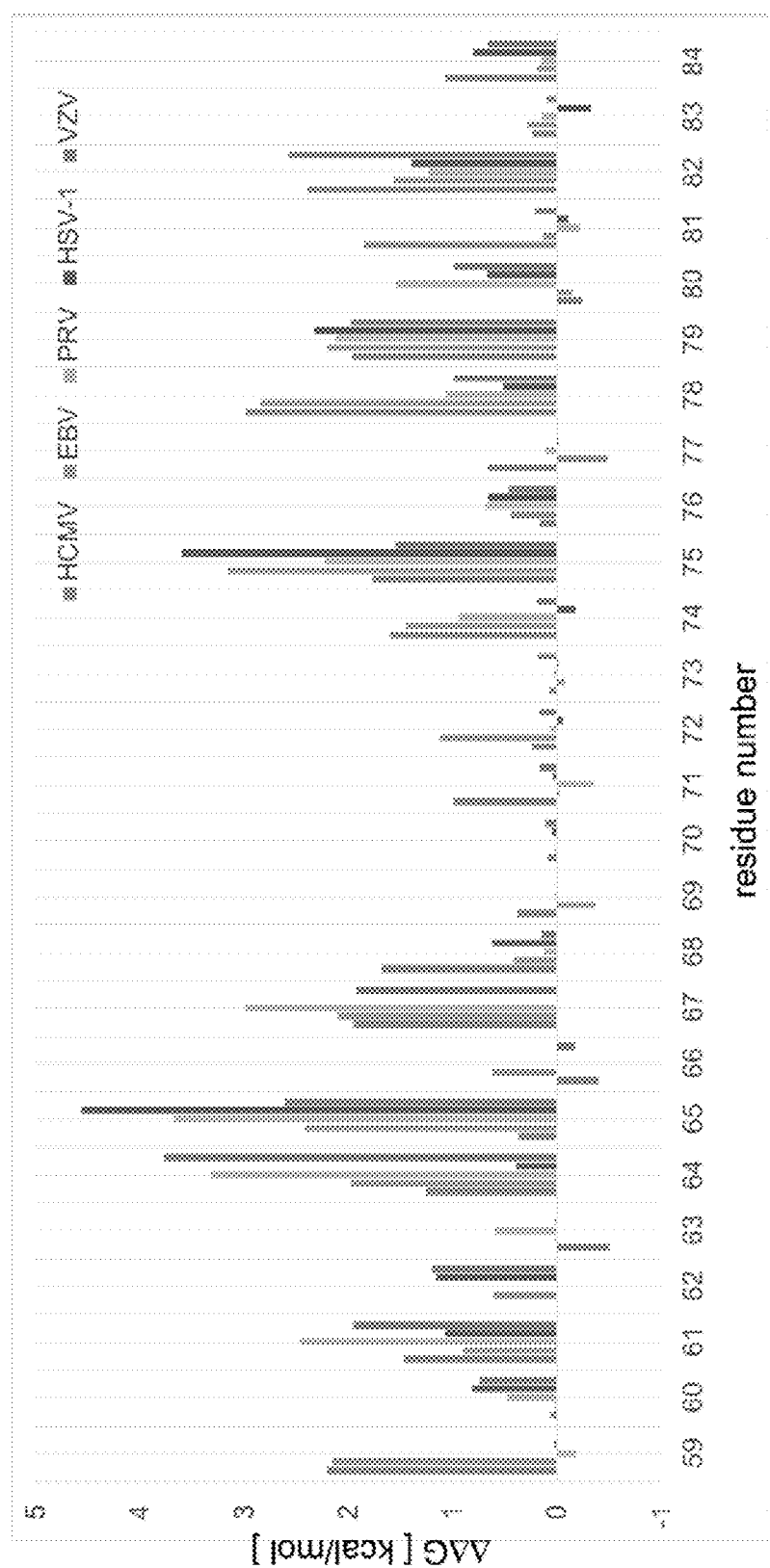

FIG. 13: Calculated energy profiles of the hook-into-groove interaction. The plot shows the loss of binding energy resulting from a replacement of individual hook residues by alanine (large positive values indicate hook residues that are important for groove interaction). Calculations were performed for three alpha-herpesviruses (PRV, HSV-1, and VZV), the gamma-herpesvirus EBV, and the beta-herpesvirus HCMV. The sequence numbering below the alignment refers to HCMV pUL53.

FIG. 14: Sequence comparison of the designed shared hook to the wild-type hooks of the HCMV pUL53 and EBV BFLF2.

SEQ ID No: 67-LTLHDLHDIFREHPELELKYLNMMKMAITG
SEQ ID No: 68-DRSHFSLRDFFRGISANFELGKDFLREMNTPIH
SEQ ID No: 69-FYLWSMFIAIMRYFELGMKYLNMMMKPMIG

Figure 15:
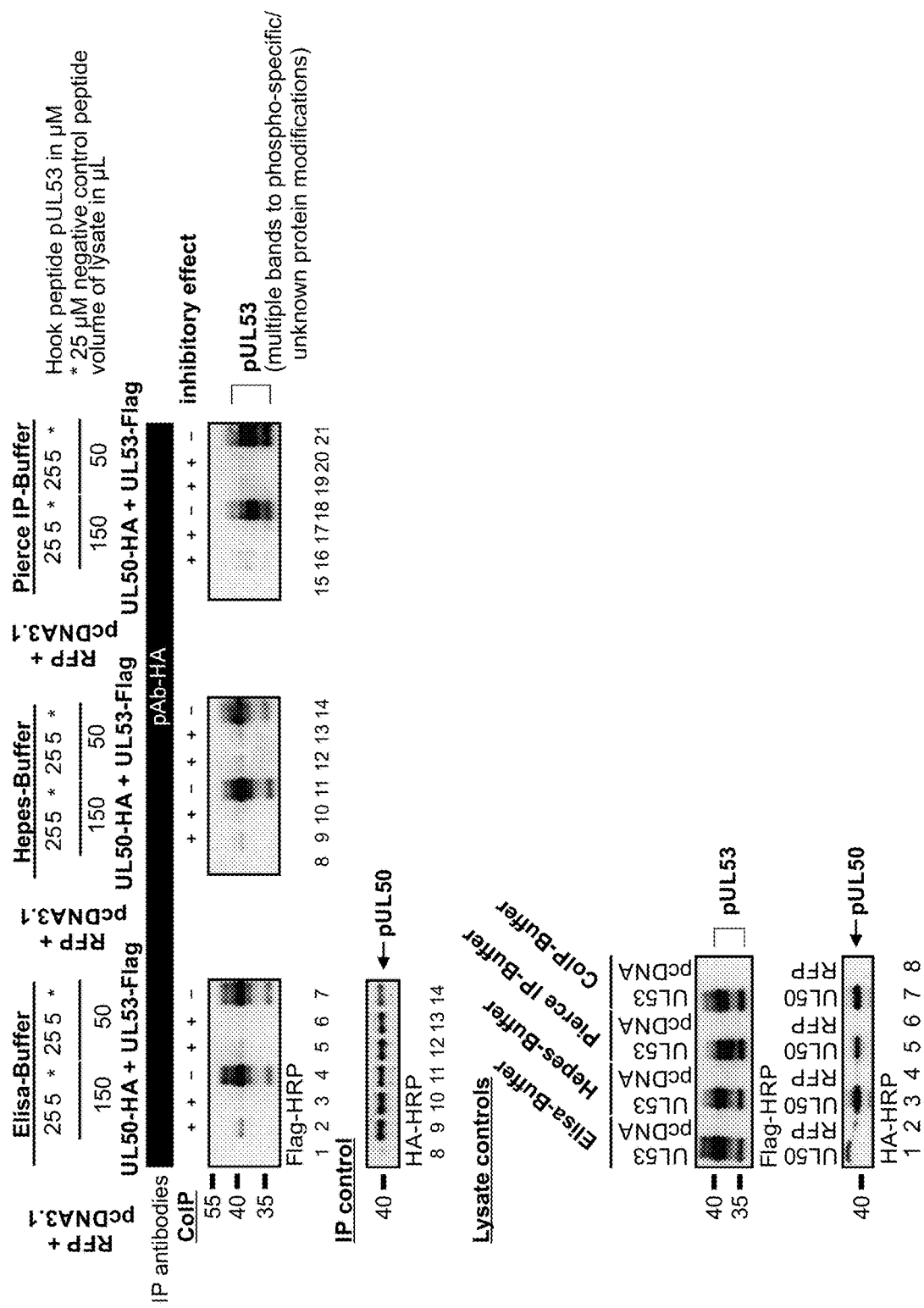

FIG. 15: Coimmunoprecipitation analysis with hook peptide pUL53 in three different buffers FIG. 16: (A) Structural models of the shared hook (marked with arrows) in complex with HCMV pUL50 (left) and EBV BFRF1 (right). (B) Two different views of HCMV pUL50 indicating the degree of surface conservation among the herpesviral pUL50 homologs. The structures are shown in a space-filling representation with conserved and non-conserved regions highlighted in light grey and dark grey, respectively. The most conserved residues involved in pUL53 binding are labelled.

Figure 17:
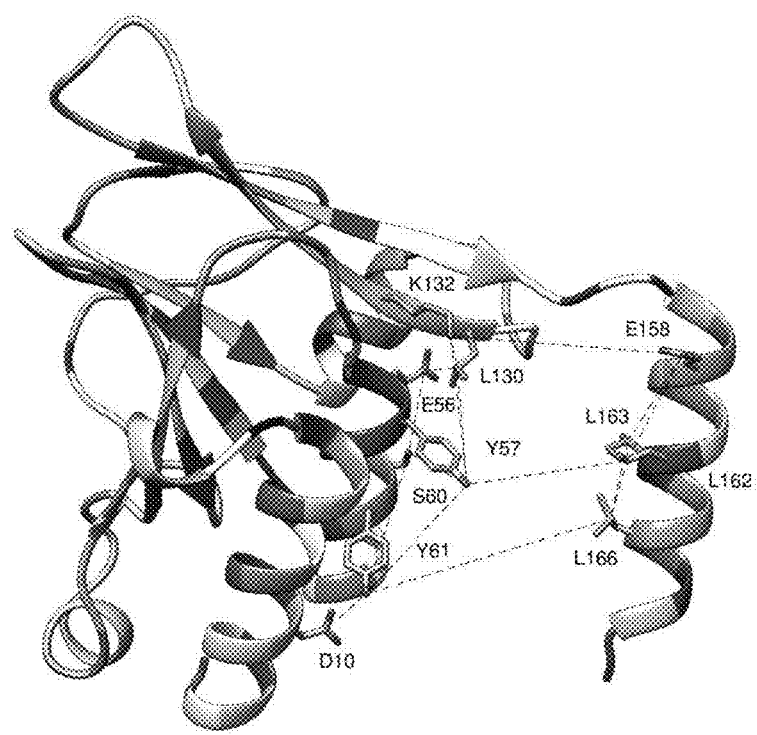

FIG. 17: Ribbon representation of HCMV pUL50 (same greyscale code as in FIG. 16). The most conserved residues involved in pUL53 binding are shown as sticks.

FIG. 18: A) Interaction of soluble Herpesvirus NEC proteins. Left: HCMV pUL50-pUL53 interaction; Right: EBV BFRF1-BFLF2 interaction. B) Design of Herpesvirus NEC hook peptides based on the crystal structures of the HCMV pUL50-PUL53 complex (left) and EBV BFRF1 fused to the hook region of BFLF2 (right). C) Inhibition of the HCMV pUL50-PUL53 (left) and EBV BFRF1-BFLF2 (right) interactions by both HCMV and EBV hook peptides and proteins.

DETAILED DESCRIPTION OF THE INVENTION

The capsids of herpesvirus are generally assembled within the nucleus of infected cells whereas the final maturation takes place in the surrounding cytosol. Hence, to access the final maturation compartment, i.e. the cytoplasm, the pre-formed intranuclear capsids have to cross the nuclear envelope as barrier. This is realized by budding at the inner nuclear membrane, thereby forming a primary enveloped particle residing in the perinuclear cleft. As stated above, a heterodimeric complex of two highly conserved proteins among the Herpesviridae drives the formation of primary envelopes. For instance, in case of herpes simplex virus these proteins forming the core NEC are designated by common nomenclature as pUL34, a tail-anchored transmembrane protein located in the nuclear envelope, and pUL31.

The nuclear egress complex (NEC) recruits viral and cellular kinases to soften the nuclear lamina and for allowing access of DNA packaged capsids to the inner nuclear membrane.

How the capsids are recruited to the budding site and into the primary virus particle is still not completely understood in detail. Fusion of the primary envelope with the outer nuclear membrane then results in translocation of the capsid to the cytosol. It is to be noted that such fusion is distinct from fusion during infectious entry of free virions into target cells, namely in that such infectious entry does not require the highly conserved essential core herpesvirus fusion machinery. Nuclear egress can thus be recognized as a vesicle (primary envelope)-mediated transport of cargo (capsids) through the nuclear envelope.

The detailed crystal structures of EBV heterodimeric proteins BFRF1 and BFLF2 (SEQ ID Nos 3 and 4), of VZV heterodimeric proteins ORF24 and ORF27 (SEQ ID Nos 5 and 6), and of the pUL50-pUL53 heterodimer of HCMV (SEQ ID Nos 1 and 2) and truncated forms thereof, respectively, were determined. It was noted that the proteins adopt a globular fold with mixed α and β secondary structure elements (see FIGS. 1, 2 and particularly FIG. 12).

It was previously described that the pUL53-specific features of a zinc-binding site and a hook N-terminal extension of specific 29 aa (44) are an essential structural element of pUL50-pUL53 interaction in HCMV. The pUL50 structure overall resembles the recently published NMR structure of the murine cytomegalovirus homologue pM50, but surprisingly and unexpectedly the instant inventors found a considerable repositioning of the very C-terminal α-helix of pUL50 upon pUL53 binding. pUL53 was found to show structural resemblance with the GHKL domain of bacterial sensory histidine kinases (see FIG. 2 A).

A more detailed examination of the crystal structure indicated partial assembly of pUL50-pUL53 heterodimers to hexameric ring-like structures (see FIG. 2 C), which are suggested to provide additional scaffolding opportunities for building nuclear egress complexes.

Following this, the inventors combined the herein disclosed structural information on pUL50-pUL53 core NEC proteins and derived a more detailed understanding of the mechanism of the NEC in Herpesviridae in general, and particularly for the species HHV-1 to HHV-8, MCMV and/or PrV, for betaherpesviruses such as HCMV, HHV-6, HHV-7, or for the gammaherpesvirus EBV, or the like.

It was concluded that the mechanism of action based on the hook-into-groove structure represents a unique target for developing novel screening methods, which could result in novel types of more efficient antiviral drugs.

New fusion proteins are provided herein, which provide an even better crystal structure resolution. These proteins are shown in SEQ ID NOs: 1 to 6. Whenever, reference is made to polypeptides according to the present invention, these sequences and homologues thereof are included. These proteins may be used in assays or methods for the identification and analysis of molecules interacting with/inhibiting/modulating the NEC proteins. Specifically, a hook-into-groove structure was found during its interaction/heterodimerization (see FIG. 12), which exists as a conserved mechanism among the Herpesviridae (see FIG. 4) and likely plays a role in the viruses nuclear egress. This feature leads to improved options of broad-spectrum anti-herpesviral therapy through finding novel antiviral agents. A similar structure was found for the NEC proteins of HCMV and EBV as shown in FIG. 12.

Furthermore, it was found that four specific aa-based phospho-sites of the pUL50 protein are positioned outside the pUL50 and pUL53 interacting region (see FIG. 4), and which are decisive for triggering the phosphorylation during heterodimerizations/multimerizations of the NEC, and thus are involved in virion maturation via nuclear egress.

In accordance with the present invention, this may also lead to improved options of broad-spectrum anti-herpesviral therapy through finding novel antiviral agents that bind to/interact with/antagonize or block/mask/shield the identified phospho-site(s), either alone or in combination thereof, to affect/hinder/inhibit phosphorylation during heterodimerizations/multimerizations of the NEC. Such therapy based on specific phospho-sites may be a second line antiviral strategy to the above hook-into-grove structures, or may be combined therewith (see further details below).

Screening Methods for Agents Inhibiting the Hook-into-Groove Mechanism of pUL50-pUL53 and/or EBV BFRF1-BFLF2 and/or VZV ORF24-ORF27

The method may include three following steps:
(i) optionally labeling a protein/peptide and/or its target (e.g. protein, protein fragment, nucleic acid, peptide, peptide fragment and signaling molecule, but not limited thereto) at one or more sites with, e.g., a fluorine isotope, but not limited thereto (i.e., exchanging one or more natural amino acids with fluorine substituted amino acids);
(ii) providing a reaction system comprising
   (a) the protein/peptide or protein fragment/peptide fragment,
   (b) one or more candidate compounds (i.e., potential binding (interacting/antagonizing small molecules), and
   (c) the protein/peptide binding target (e.g. protein, protein fragment, peptide, peptide fragment, nucleic acid, and/or signaling molecule, but not limited thereto),
where at least protein/peptide, at least target or both the protein/peptide and the target are optionally labeled with the fluorine isotope; and
(iii) monitoring interaction of the protein/peptide with its binding target using the changes in a signal (e.g., chemical shift perturbation, line shape, and signal relaxation), and whereby a reduced binding level in the presence of the candidate compound relative to a control binding level is indicative of the modulating/inhibitory activity of the compound in suppressing the protein-protein formation/heterodimerization.

At this stage of the disclosed screening methods, its target (e.g., the pUL53 "hook" or "hook-into-groove") can be prepared by a variety of techniques known in the art. Examples include protein expressions in *Escherichia coli* cells containing a plasmid encoded with said protein.

The peptide targets of the invention are not particularly limited to the peptide itself, but may also comprise fragments thereof as long as it interacts/binds with e.g. the small molecule to be tested in the screening methods of the present invention.

As a second line strategy, that may be combined with the findings for the crystal structure of the core NEC of pUL50 and pUL53 and/or BFRF1-BFLF2 (or NEC counterparts derived from other herpesviruses) as disclosed herein, another key finding of the invention is the detection of specific aa-based phospho-sites of pUL50 that are positioned outside the pUL50-PUL53 and/or EBV BFRF1-BFLF2 interacting region, but are decisive for phosphorylation during NEC-based mechanisms, i.e. the NEC multimerization, and thus provide for another novel target in accordance with the instant invention.

In this regard, the inventors foresee to mask, block or shield said specific aa-based phospho-sites by agents/compounds/small molecules to be identified by the herein disclosed respective screening methods/assays to affect/modulate/inhibit the phospho-sites either alone or in combination to influence structure and/or function of the viral NEC multimerization within the group of Herpesviridae, such as in species selected from a group HHV-1 to HHV-8, MCMV or PrV, for betaherpesviruses, or for the gammaherpesviruses, such as EBV, or the like. This may be also exploited in novel antiviral strategies thereof.

Accordingly, the invention further generally relates to screening methods for identifying small molecules that inhibit the formation of the NEC heterodimer pUL50-pUL53 and/or EBV BFRF1-BFLF2 and/or VZV ORF24 and ORF27, either on the basis of
  i) steric inhibition of pUL50-pUL53 and/or EBV BFRF1-BFLF2 and/or ORF24 and ORF27 interaction/heterodimerization and/or
  ii) protein kinase inhibition to address the phosphorylation aspect during NEC multimerization and/or
  iii) masking/shielding/blocking of the specific phosphosites of pUL50 and/or EBV BFRF1 ORF24 and ORF27 either alone or in combinations thereof (see further below).

In specific embodiments of the invention, the inventors applied two screening methods, which allow the measurement of pUL50-pUL53 and/or EBV BFRF1-BFLF2 and/or ORF24 and ORF27 interaction in human cultured cells.

I) Confocal Microscopy-Based Method

In a first aspect of said screening methods a confocal microscopy-based method is applied, which comprises the following steps:
  a) a BFRF1 and BFLF2 (SEQ ID Nos 3 or 4), and/or ORF24 and ORF27 (SEQ ID Nos 5 or 6) heterodimer of EBV and VZV, respectively, and/or pUL50-pUL53 heterodimer of HCMV (SEQ ID Nos 1 and 2) is produced either by co-transfection of two expression constructs for these two proteins, either
    a1) in the absence of EBV, VZV, and/or HCMV infection, or
    a2) in EBV, VZV, and/or HCMV-infected human primary cells, preferably human fibroblasts (HFF) or other HCMV permissive cells to be examined,
  b) a double staining of said proteins by indirect immunofluorescence or comparable techniques follows, which allows a determination of the formation of the heterodimers BFRF1-BFLF2 of EBV and/or ORF24-ORF27 of VZV and/or pUL50-pUL53 of HCMV on the nuclear rim (i.e. annular co-localization of the two proteins).

II) Co-Immunoprecipitation-Based Method

In a second aspect a co-immunoprecipitation-based method can be used for the detection of BFRF1-BFLF2 and/or ORF24-ORF27 and/or pUL50-pUL53 interactions (44). This method is adapted to investigate blocking the interaction of the two proteins by NEC-incubation with the tested small molecules in solution. Proof of BFRF1-BFLF2 and/or ORF24-ORF27 and/or pUL50-pUL53 interaction and/or inhibition thereof preferably takes place in a non-radioactive manner. In an alternative embodiment of the invention the detection of BFRF1-BFLF2 and/or ORF24-ORF27 and/or pUL50-pUL53 interaction is conducted in a more sensitive manner by means of radioactively labeled proteins on Western blots or autoradiograms. A quantification of the signals can be made by densitometry.

Agent Screening

Agent screening in the context of the invention identifies agents that modulate/inhibit function and/or structure of the EBV polypeptides/proteins BFRF1 and/or BFLF2 and/or VZV polypeptides/proteins ORF24 and/or ORF27 and/or HCMV polypeptides/proteins pUL50 and/or pUL53. Of particular interest are screening assays for agents that have a low toxicity for human cells.

The present invention provides new fusion proteins comprising pUL50 and pUL53 (in the fused sequences of SEQ ID NOs. 1 and 2), BFRF1 and BFLF2 (in the fused sequences of SEQ ID NOs. 3 and 4) and/or ORF24-ORF27 (in the fused sequences SEQ ID NOs. 5 and 6), or homologues thereof. The amino acid residues comprising the respective subunits of the NEC are explicitly referred to in the below embodiments. The two subunits of the fusion proteins may be linked by a suitable linker sequence, e.g., as depicted in the sequence listing. Functional homologues of the fusion proteins are those that are capable of heterodimerization with its cognate NEC partner protein, e.g., functional homologues of pUL50 and/or pUL53 should be able to form a dimer of sufficient stability to use the same in the herein described screening methods, wherein sufficient stability means that they form a heterodimer that is at least 50% as stable (does not dissociate) as the herein described new fusion proteins under identical assay conditions. Assays for the determination of the stability/strength of protein-protein interactions are known in the art. As used herein, the term "homologue of any of the herein described polypeptides" means that such polypeptide is a "functional homologue". The term "functional" does not necessarily mean that the proteins would be functional under in vivo conditions, i.e. that they function as NEC proteins permitting the maturation of virions. The functional homologues are, however, at least suitable to determine the structure of the proteins, e.g. the respective polypeptides in the heterodimer, and to function as matrices or tools in the modelling and identification of compounds (in in silico methods) that are interacting, modulating and/or inhibiting the NEC proteins, in particular in more than one herpesvirus derived NEC. Homologues according to the present invention also designate polypeptides derived from other viral strains of the above-mentioned herpesviruses. Polypeptides of the NEC of different strains may also differ from the explicitly mentioned sequences hereinbelow. These differences may be the result of modifications of the nucleic acid sequence encoding these polypeptides so that one or more amino acid residues may be different from the herein disclosed sequences. These modifications may be deletions, additions, substitutions, inversions, et cetera, as long as they are derived from NEC polypeptides of herpesviruses. With respect to the herein disclosed sequences, in particular sequences in SEQ ID NOs: 1 to 6, the modifications may result in the peptide sequences that are slightly different from the previously mentioned sequences, i.e. they may be at most 20% different, or at most 15% different, or at most 10% different, or at most 9% different, or at most 8% different, or at most 7% different, or at most 6% different, or at most 5% different, or at most 4% different, or at most 3% different, or at most 2% different, or at most 1% different, provided that they encode NEC (derived-) polypeptides that are capable of heterodimerization. Therefore, whenever reference is made to homologues of the sequences according to the present invention, the modified sequences as explained above are also meant.

The linker amino acids may, for example, be glycine-rich amino acid sequences comprising 3 to 12 amino acids.

The person skilled in the art is aware, a wide variety of assays may be used for this purpose, as for instance binding assays of a candidate agent/compound to a target protein, target protein fragment, target polypeptide, target peptide, target peptide fragment, and determining/detecting the effect of said tested candidate agent/compound on replication of viruses selected from a group of the Herpesviridae, such as among the species HHV-1 to HHV-8, MCMV and/or PrV, but not limited thereto, determining/detecting the effect on tissue specificity, or determining/detecting functional and/or structural changes of the target or its interactions with other protein(s), protein fragment(s), polypeptide(s), peptide(s), peptide fragment(s) and the like.

Candidate agents/compounds may be assayed for inhibitory efficacy on viral replication, for inhibitory efficacy of hindering the viral DNA-packaged capsid export from nucleus to cytoplasm (i.e. nuclear egress) of a virus, inducing temperance of viral infection, for preventing infection in general, and for preventing virion maturation in general, e.g. in betaherpesviruses, but not limited thereto.

With the context of the invention, for the person skilled in the art it is readily apparent that the agent/compound screening extends particularly to screening putative agents/compounds that are useful in broad-spectrum antiviral agents within the group of the Herpesviridae, and specifically, among the species HHV-1 to HHV-8, MCMV and/or PrV, but not limited thereto, based on its high degree of homology in respect to the peptide target motive of SEQ ID NOs: 1 to 6 of the invention.

For the person skilled in the art it is readily apparent that the herein disclosed N-terminal hook structure of the pUL53 protein (SEQ ID NO: 7), is highly conserved among the species HHV-1 to HHV-8, MCMV and/or PrV, but not limited thereto, in view of its respective peptide target motives of specific strains thereof depicted in FIG. 4 and shown in the respective sequences.

Hence, it is reasonable for the skilled person, in view of the entire disclosure of the invention, to screen for candidate agents/compounds that affect/inhibit the NEC core interaction/heterodimerization of the proteins BFRF1 and BFLF2 and/or of the proteins ORF24 and ORF27 and/or of the proteins pUL50 and pUL53 depicted in the sequence listing or other herpesviral counterparts, as disclosed herein.

Accordingly, in the context of the invention the screening for agents/compounds that affect/inhibit either of the components of the heterodimers comprising BFRF1 and BFLF2 and/or ORF24 and ORF27 and/or pUL50 or pUL53 alone or their respective interaction/heterodimerization may be performed using an in vitro model or an in vivo model, or a cell permissive for or infected with a virus selected from a group of Herpesviridae, particularly among the species HHV-1 to HHV-8 of the betaherpesviruses, or gammaherpesviruses (such as EBV), and PrV, but not limited thereto, said cell optionally being further mutated, or a panel of cells permissive for or infected with said virus selected from a group of Herpesviridae, particularly among the species HHV-1 to HHV-8 and/or PrV, in particular among the betaherpesviruses, but not limited thereto, said cell optionally being further mutated, or on the basis of purified proteins, protein fragments, peptides, peptide fragments corresponding to the above herpesvirus NEC proteins either alone or in combination or corresponding to homologues thereof or on the basis of the purified N-terminal hook region spanning the aa 59-87 according to SEQ ID NO: 7 or any homologue thereof, according to any suitable method apparent to the person skilled in the art. The person skilled in the art generally is aware how to identify e.g. ligands, agents, small molecules or substrates that bind to, modulate, inhibit or mimic the interaction of BFRF1 and/or BFLF2 and/or ORF24 and/or ORF27 and/or pUL50 and/or pUL53 or respective homologues thereof.

Where the screening method/assay is a binding assay, one or more of the molecules may be joined to a label, where the label can directly or indirectly provide a detectable signal. Various labels include, but not limited thereto, radioisotopes, fluorescers, chemiluminescers, enzymes, peptides, specific binding molecules, particles, e.g. magnetic particles, and the like.

Specific binding molecules include, but not limited thereto, pairs, such as biotin and streptavidin, digoxin and antidigoxin, etc. For the specific binding members, the complementary member would normally be labeled with a molecule that provides for detection, in accordance with known procedures.

The person skilled in the art is aware that a variety of other reagents may be included in the screening methods/assays of the instant invention for testing agents/compounds/small molecules vis-à-vis the mechanisms disclosed herein and/or vis-à-vis the blocking/masking/shielding of one or more specific phospho-sites as disclosed herein, e.g. in betaherpesviruses, and/or in the gammaherpesvirus EBV.

These include exemplarily reagents like salts, neutral proteins, e.g. albumin, detergents, etc. that are used to facilitate optimal protein-protein or protein-peptide or peptide-antibody binding and/or reduce non-specific or background interactions. Reagents that improve the efficiency of the assay, such as protease inhibitors, nuclease inhibitors, anti-microbial agents, etc. may be used. The mixture of components is added in any order that provides for the requisite binding. Incubations are performed at any suitable temperature, typically between 4 and 40° C., but not limited thereto. Incubation periods are selected for optimum activity, but may also be optimized to facilitate rapid high-throughput screening. Typically between 0.01 and 24 hours will be sufficient, but not limited thereto.

Preliminary screens can be conducted by screening for compounds/agents capable of binding to BFRF1 and/or BFLF2 and/or ORF24 and ORF27 and/or pUL50 and/or pUL53 either alone or in combination, or on the basis of blocking/masking/shielding of one or more specific phospho-sites as disclosed herein. The binding assays usually involve contacting BFRF1 and/or BFLF2 and/or ORF24 and ORF27 and/or pUL50 and/or pUL53, either alone or in combination as disclosed herein, with one or more test compounds and allowing sufficient time for the protein/peptide or a fragment thereof and test compounds to form a binding complex. Any binding complexes formed can be detected using any of a number of established analytical techniques. Protein/peptide binding assays include, but are not limited to, methods that measure co-precipitation, co-migration on non-denaturing SDS-polyacrylamide gels, and co-migration on Western blots (see, e.g., Bennet, J. P. and Yamamura, H. I. (1985) "*Neurotransmitter, Hormone or Drug Receptor Binding Methods,*" in *Neurotransmitter Receptor Binding* (Yamamura, H. I., et al., eds.), pp. 61-89.

Agents to be Tested with the Context of the Invention

The terms "agent", "small molecules", "compound(s) to be tested" or similar expressions as used herein describe any molecule, e.g. protein, peptide or pharmaceutical, with the capability of altering, inhibiting or mimicking the physiological function of an EBV polypeptide/protein BFRF1 and/or BFLF2 and/or VZV polypeptide/protein ORF24 and ORF27 and/or HCMV polypeptide/protein pUL50 and/or pUL53. Generally a plurality of assay mixtures are run in parallel with different agent concentrations to obtain a differential response to the various concentrations for modulating or inhibiting the EBV polypeptide/protein BFRF1 and/or BFLF2 and/or VZV polypeptide/protein ORF24 and ORF27 and/or pUL50-pUL53 interaction either in vitro or in vivo. Typically one of these concentrations serves as a negative control, i.e. at zero concentration or below the level of detection.

Candidate agents within the context of the instant invention encompass numerous chemical, biochemical and biological classes, though preferably they are organic molecules or inorganic molecules, more preferably small organic compounds or small inorganic molecules having a molecular weight of more than 10 and less than about 2.500 daltons, preferably more than 50 and less than 1.500 daltons molecular weight, more preferably more than 50 and less than 1000 daltons molecular weight, even more preferably more than 50 and less than 800 daltons molecular weight.

Candidate agents with the context of the invention may further comprise functional groups necessary for structural interaction with proteins, peptides, i.e. particularly hydrogen bonding, and preferably include at least an amine, carbonyl, hydroxyl or carboxyl group, more preferably at least two of the functional chemical groups, but not limited thereto. The candidate agents of the invention may further comprise cyclical carbon or heterocyclic structures and/or aromatic or polyaromatic structures substituted with one or more of the above functional groups. Candidate agents within the context of the invention may also be found among biomolecules including in silico designed biomolecules, synthesized biomolecules, proteins, peptides, polypeptides, saccharides, fatty acids, steroids, purines, pyrimidines, derivatives thereof, and structural analogs or combinations thereof.

With the context of the invention candidate agents are to be obtained from a wide variety of sources including in silico designed libraries, libraries of synthetic or natural compounds. For example, the person skilled in the art is aware that numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Test agents, with the context of the invention, can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642.

In case the tested agents/compounds/small molecules are certain peptides or polypeptides, as well as nucleic acids that, by virtue of the degeneracy of the genetic code, are not identical in sequence, these also include variants thereof. Variant polypeptides can include aa substitutions, additions or deletions. The amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. With the context of the invention variants can be designed so as to retain or have enhanced biological inhibitory activity of a particular region of the pUL50 and/or the pUL53 protein (e.g., a functional domain and/or, where the polypeptide is a member of a protein family, a region associated with a consensus sequence). Variants within the context of the invention also include fragments of the polypeptides to be tested, particularly biologically active fragments (i.e. those influencing, inhibiting or modulating the activity of the NEC and consequently, virus release from the cell, virus maturation and/or any other step in the production of infectious viruses, particularly the herein described Herpesviridae) and/or fragments corresponding to functional domains. Fragments of interest will typically be at least about 5 aa, 10 aa to at least about 15 aa in length, usually at least about 50 aa in length, and can be as long as 300 aa in length or longer, but will usually not exceed about 500 aa in length, where the fragment will have a contiguous stretch of amino acids that is identical to the provided polypeptide sequence.

Active test agents/compounds/small molecules identified by the screening methods/assays as described herein that affect/modulate/inhibit pUL50 and/or pUL53 activity or from homologues thereof, preferably on the basis of the herein disclosed hook-like mechanism, and/or herpesvirus growth, preferably HCMV growth, can serve as lead compounds for the synthesis of further analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs for implementing these techniques are available. See, e.g., Rein et al., (1989) *Computer-Assisted Modeling of Receptor-Ligand Interactions* (Alan Liss, New York).

In a specific embodiment of the invention, the test agents/compounds/small molecules are antibodies, IgG scaffolds, non-IgG scaffolds.

An antibody according to the present invention is a protein including one or more polypeptides substantially encoded by immunoglobulin genes that specifically binds an antigen. The recognized immunoglobulin genes include the kappa, lambda, alpha (IgA), gamma (IgG1, IgG2, IgG3, IgG4), delta (IgD), epsilon (IgE) and mu (IgM) constant region genes, as well as the myriad immunoglobulin variable region genes. Full-length immunoglobulin light chains are generally about 25 Kd or 214 amino acids in length. Full-length immunoglobulin heavy chains are generally about 50 Kd or 446 amino acid in length. Light chains are encoded by a variable region gene at the N-terminus (about 110 amino acids in length) and a kappa or lambda constant region gene at the C-terminus. Heavy chains are similarly encoded by a variable region gene (about 116 amino acids in length) and one of the other constant region genes.

The basic structural unit of an antibody is generally a tetramer that consists of two identical pairs of immunoglobulin chains, each pair having one light and one heavy chain. In each pair, the light and heavy chain variable regions bind to an antigen, and the constant regions mediate effector functions. Immunoglobulins also exist in a variety of other forms including, for example, Fv, Fab, and (Fab')2, as well as bifunctional hybrid antibodies and single chains (e.g., Lanzavecchia et al., Eur. J. Immunol. 17:105, 1987; Huston et al, Proc. Natl. Acad. Sci. U.S.A., 85:5879-5883, 1988; Bird et al, Science 242:423-426, 1988; Hood et al, Immunology, Benjamin, N.Y., 2nd ed., 1984; Hunkapiller and Hood, Nature 323:15-16, 1986). An immunoglobulin light or heavy chain variable region includes a framework region interrupted by three hypervariable regions, also called complementarity determining regions (CDRs) (see, Sequences of Proteins of Immunological Interest, E. Kabat et al, U.S. Department of Health and Human Services, 1983). As noted above, the CDRs are primarily responsible for binding to an epitope of an antigen. An immune complex is an antibody, such as a monoclonal antibody, chimeric antibody, humanized antibody or human antibody, or functional antibody fragment, specifically bound to the antigen.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody can be joined to human constant segments, such as kappa and gamma 1 or gamma 3. In one example, a therapeutic chimeric antibody is thus a hybrid protein composed of the variable or antigen-binding domain from a mouse antibody and the constant or effector domain from a human antibody, although other mammalian species can be used, or the variable region can be produced by molecular techniques. Methods of making chimeric antibodies are well known in the art, e.g., see U.S. Pat. No. 5,807,715. A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor" and the human immunoglobulin providing the framework is termed an "acceptor". In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical.

Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions, which have substantially no effect on antigen binding or other immunoglobulin functions. Exemplary conservative substitutions are those such as Gly, Ala; Val, Ile, Leu; Asp, Glu; Asn, Gln; Ser, Thr; Lys, Arg, Phe, and Tyr. Humanized immunoglobulins can be constructed by means of genetic engineering (e.g., see U.S. Pat. No. 5,585,089). A human antibody is an antibody wherein the light and heavy chain genes are of human origin. Human antibodies can be generated using methods known in the art. Human antibodies can be produced by immortalizing a human B cell secreting the antibody of interest. Immortalization can be accomplished, for example, by EBV infection or by fusing a human B cell with a myeloma or hybridoma cell to produce a trioma cell. Human antibodies can also be produced by phage display methods (see, e.g., Dower et al., PCT Publication No. WO91/17271; McCafferty et al, PCT Publication No. WO92/001047; and Winter, PCT Publication No. WO92/20791), or selected from a human combinatorial monoclonal antibody library (see the Morphosys website). Human antibodies can also be prepared by using transgenic animals carrying a human immunoglobulin gene (for example, WO93/12227; WO91/10741).

Thus, the antibody may have the formats known in the art. Examples are human antibodies, monoclonal antibodies, humanized antibodies, chimeric antibodies, CDR-grafted antibodies. In a preferred embodiment antibodies according to the present invention are recombinantly produced antibodies as e.g. IgG, a typical full-length immunoglobulin, or antibody fragments containing at least the F-variable domain of heavy and/or light chain as e.g. chemically coupled antibodies (fragment antigen binding) including but not limited thereto Fab-fragments including Fab minibodies, single chain Fab antibody, monovalent Fab antibody with epitope tags, e.g. Fab-V5Sx2; bivalent Fab (mini-antibody) dimerized with the CH3 domain; bivalent Fab or multivalent Fab, e.g. formed via multimerization with the aid of a heterologous domain, e.g. via dimerization of dHLX domains, e.g. Fab-dHLX-FSx2; F(ab')2-fragments, scFv-fragments, multimerized multivalent or/and multispecific scFv-fragments, bivalent and/or bispecific diabodies, BITER (bispecific T-cell engager), trifunctional antibodies, polyvalent antibodies, e.g. from a different class than G; single-domain antibodies, e.g. nanobodies derived from camelid or fish immunoglobulins and numerous others. In addition to antibodies other biopolymer scaffolds are well known in the art to complex a target molecule and have been used for the generation of highly target specific biopolymers. Examples are aptamers, spiegelmers, anticalins and conotoxins. In a preferred embodiment the antibody format is selected from the group comprising Fv fragment, scFv fragment, Fab fragment, scFab fragment, (Fab) 2 fragment and scFv-Fc Fusion protein. In another preferred embodiment the antibody format is selected from the group comprising scFab fragment, Fab fragment, scFv fragment and bioavailability optimized conjugates thereof, such as PEGylated fragments. One of the most preferred formats is the scFab format.

According to the invention the binder to the NEC proteins or homologues thereof is selected from the group consisting of antibodies e.g. IgG, a typical full-length immunoglobulin, or antibody fragments containing at least the F-variable domain of heavy and/or light chain as e.g. chemically coupled antibodies (fragment antigen binding) including but not limited thereto Fab-fragments including Fab minibodies, single chain Fab antibody, monovalent Fab antibody with epitope tags, e.g. Fab-V5Sx2; bivalent Fab (mini-antibody) dimerized with the CH3 domain; bivalent Fab or multivalent Fab, e.g. formed via multimerization with the aid of a heterologous domain, e.g. via dimerization of dHLX domains, e.g. Fab-dHLX-FSx2; F(ab')2-fragments, scFv-fragments, multimerized multivalent or/and multispecific scFv-fragments, bivalent and/or bispecific diabodies, BITE® (bispecific T-cell engager), trifunctional antibodies, polyvalent antibodies, e.g. from a different class than G; single-domain antibodies, e.g. nanobodies derived from camelid and fish immunoglobulines.

Non-IgG scaffolds may be protein scaffolds and may be used as antibody mimics as they are capable to bind to ligands or antigens. Non-IgG scaffolds may be selected from the group comprising tetranectin-based non-IgG scaffolds (e.g. described in US 2010/0028995), fibronectin scaffolds (e.g. described in EP 1266025); lipocalin-based scaffolds (e.g. described in WO 2011/154420); ubiquitin scaffolds (e.g. described in WO 2011/073214), transferring scaffolds (e.g. described in US 2004/0023334), protein A scaffolds (e.g. described in EP 2231860), ankyrin repeat based scaffolds (e.g. described in WO 2010/060748), microproteins, preferably microproteins forming a cystine knot) scaffolds (e.g. described in EP 2314308), Fyn SH3 domain based scaffolds (e.g. described in WO 2011/023685) EGFR-A-domain based scaffolds (e.g. described in WO 2005/040229) and units domain based scaffolds (e.g. described in EP 1941867).

Throughout the specification the "antibodies", or "antibody fragments" or "IgG-scaffolds" or "non-Ig scaffolds" in accordance with the invention are capable of binding NEC proteins, e.g., the specific aa-based phospho-sites either alone or in combination of the instant invention.

In addition to the antibodies described above other biopolymer scaffolds are well known in the art to complex a target molecule within the context of the invention either alone or in combination of the instant invention and have been used for the generation of highly target specific biopolymers. Examples are aptamers, spiegelmers, anticalins and conotoxins.

In a preferred embodiment the antibody format is selected from the group comprising Fv fragment, scFv fragment, Fab fragment, scFab fragment, F(ab)2 fragment and scFv-Fc Fusion protein. In another preferred embodiment the antibody format is selected from the group comprising scFab fragment, Fab fragment, scFv fragment and bioavailability optimized conjugates thereof, such as PEGylated fragments. One of the most preferred formats is the scFab format.

Providing a Reaction System

The herein disclosed screening methods/assay, either (labeled) test agent/compound/small molecules, its target EBV polypeptide/protein BFRF1 and/or BFLF2 and/or VZV polypeptide/protein ORF24 and ORF27 and/or pUL50 and/or pUL53 protein or homologues thereof as defined above and infra (e.g. of the sequences SEQ ID NOs: 1 to 6), or fragments thereof are at least combined in a solution and may be optionally further combined with one or more candidate agents/compounds/small molecules, but not limited thereto. The candidate agents/compounds/small molecules is/are a molecule that, for example, may inhibit viral growth/replication of viruses selected from a group of Herpesviridae, particularly among the species HHV-1 to HHV-8, MCMV and PrV, but not limited thereto, and the resultant symptoms of such viral infections, more preferably inhibit HCMV growth and the symptoms of such viral infections.

The candidate agents/compounds/small molecules may be—without being construed as limitation to the invention—a protein or fragment thereof, a peptide or a fragment thereof, an in silico designed synthetic peptide or fragment thereof that does not occur in nature (e.g. a peptide containing D amino acid residues or a stapled peptide), a small molecule, or even a nucleic acid molecule or ribonucleic acid molecule. The skilled person is aware of various commercial sources of small molecule libraries that meet the basic criteria for useful drugs in an effort to "brute force" the identification of useful candidate compounds/agents/small molecules with the context of the instant invention.

Screening of such libraries, including libraries generated combinatorially (e.g., peptide libraries, aptamer libraries, small molecule libraries) or being generated on the basis of in silico designed small molecule libraries, is a rapid and efficient way to screen large number of related (and unrelated) compounds for activity within the context of the instant invention.

Combinatorial approaches also lend themselves to rapid evolution of potential drugs by the creation of second, third and fourth generation compounds modeled of active, but otherwise undesirable compounds. Candidate compounds may be screened from large libraries of synthetic or natural compounds. One example of a candidate compound library is an FDA-approved library of compounds that can be used by humans. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.) and a rare chemical library is available from Aldrich (Milwaukee, Wis.). Combinatorial libraries are available or can be prepared. Alternatively, libraries of natural candidate compounds in the form of bacterial, fungal, plant and animal extracts are also available from, for example, Pan Laboratories (Bothell, Wash.) or MycoSearch (N.C.), or can be readily prepared by methods well known in the art. Candidate compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical, biochemical, biological compositions or man-made compounds.

In one embodiment of the invention, the reaction system contains at least one candidate compound/agent/small molecule. In another embodiment, the reaction system can contain two or more candidate compounds/agents/small molecules, preferably between 2 and 200 compounds/agents/small molecules per batch/cavity, more preferably between 2 and 100 compounds/agents/small molecules per batch/cavity, most preferred between 2 and 50 compounds/agents/small molecules per batch/cavity because the assay does not rely on labeling of candidate compounds and can provide high efficiency screening by testing multiple candidate compounds in parallel. The person skilled in the art is aware that these indications are not to be construed as limiting in view of the wide varieties of designing suitable reaction systems to fully exploit the screening assays/methods of the instant invention. Once a batch/cavity with a BFRF1-BFLF2 and/or ORF24-ORF27 and/or pUL50-pUL53 heterodimer or both individual proteins or homologues thereof modulating and/or inhibiting compound/agent/small molecule is identified, each compound can be tested further to assess its modulating or inhibitory activity, e.g. in suitable anti-viral assays for viruses selected from a group of Herpesviridae, particularly among the species HHV-1 to HHV-8, MCMV and/or PrV, but not limited thereto, such as e.g. any suitable anti-HCMV assay (see Example portion) or any suitable anti-HSV assay, but not limited thereto.

In a preferred embodiment, the tested candidate compound/agent/small molecule is a peptide or a peptide fragment. Peptides are naturally found throughout the body in signaling pathways and hormonal control systems, but may also be in silico designed with the context of the present invention.

In a more preferred embodiment, the tested candidate compound/agent/small molecule is an in silico designed compound/agent/small molecule or a library thereof. The person skilled in the art is aware of a wide variety of methods, programs and institutions that allow for broad-spectrum in silico designs of compounds/agents/small molecules or of libraries thereof.

Types of NEC-Targeted Drugs

The inventors foresee on the basis of the disclosed screening methods/assays the finding of novel drugs that target specifically with high affinity the NEC of Herpesviridae as broad-spectrum antiviral agent (for instance against human herpesvirus HHV-1 to HHV-8) or specific strains of the species HHV-1 to HHV-8, MCMV and/or PrV, or the like (see the FIGS. 1 and 2 for illustration and steric details) or in an alternative embodiment that may be also combined with other embodiments of the instant invention, on the basis of the specific aa-based phospho-site(s) of the respective proteins in accordance with the instant invention as target.

With the context of the invention the novel type of drugs may be characterized by (i) the steric blocking of the nuclear egress complex formation of BFRF1-BFLF2 and/or ORF24-ORF27 and/or pUL50-pUL53 interaction (see the FIGS. 1 and 2) or homologues thereof and/or (ii) the specific modulation/inhibition/interference with protein requirements leading to NEC formation such as BFRF1-BFLF2 and/or ORF24-ORF27 and/or PUL50-PUL53 site-specific phosphorylation, i.e. modulation/inhibition/interference of BFRF1-BFLF2 and/or ORF24-ORF27 and/or pUL50-pUL53 phosphorylation in general and/or (iii) the drug-mediated inhibition of protein phosphorylation in the NEC formation, achievable by the inhibition of the viral protein kinase (i.e. known CDK ortholog pUL97 in case of HCMV, or pUL97 homologues of other herpesviruses), and/or (iv) one or a group of cellular protein kinases (in particular CDKs or other kinases possibly stimulating CDK activity), and/or (v) by the use of a putative new generation of drugs termed within the context of the invention as phospho-site blockers (PSB), while shielding/masking/blocking the specifically identified phospho-sites of respective proteins as disclosed herein (see below).

With the context of the invention, the inventors foresee on the basis of the information that the EBV and/or VZV and/or HCMV-specific NEC is a target structure, which is highly conserved among herpesviruses, the herein disclosed targeting strategies may either provide for candidate agents/compounds/small molecules for a EBV-, VZV- and/or cytomegalovirus-specific drug, preferably for HCMV, and/or for antiherpesviral broad-spectrum drugs in general for various viral species of the group of Herpesviridae.

Modes of the Inhibitory Activity of Phospho-Site Blockers

The inventors foresee that PSB covers the respective aa-based phospho-site as disclosed in the present invention, so that phosphorylation is prevented and thus no phosphorylation-mediated activation of the herein disclosed interaction of herpesvirus protein heterodimers or of homologues thereof occurs.

PSB allows phosphorylation but then masks/shields/blocks one or more phospho-sites of the invention, which results in no recognition of the required phosphorylation signal by interactors/ligands/complexes of the NEC. This avoids NEC formation/multimerization and finally avoids further virion maturation.

PSB may also allow phosphorylation that normally leads to a conformational change, but PSB stalls the protein in an unfortunate, transient state of an inactive conformation.

With the context of the invention, candidates for phospho-site inhibition may be cellular cyclin-dependent protein kinases, CDKs, which may directly phosphorylate pUL50-pUL53 and/or EBV BFRF1-BFLF2 or other homologous NEC proteins.

Reasons that underline this rationale are the findings for pUL97, which is known to phosphorylate the core NEC of HCMV and represents a functional/structural viral ortholog of CDKs. pUL97 and CDKs can dually phosphorylate identical substrate proteins such as pUL69, lamins, Rb, RNAP II, EF-1d. pUL97 directly interacts with cellular cyclins and the inhibition of CDKs can inhibit the core NEC recruitment at the nuclear rim.

Four specific phospho-sites in the respective protein were previously identified in the HCMV-NEC and can be also exploited either alone or in combination in the screening methods of the invention to modulate/inhibit/affect the NEC formation/multimerization of the NEC of viruses of the Herpesviridae in general, and specifically for EBV, VZV, and/or HCMV.

The inventors found that phospho-sites can be inhibited either alone or in combinations thereof for novel antiviral strategies for viruses selected from the group of Herpesviridae, such as the species HCMV, MCMV, HSV, VZV, HHV-6, EBV, PrV, or the like.

These phospho-sites are all outside the interaction surface region of pUL50-pUL53.

Following the above, the inventors provide another mechanism of BFRF1-BFLF2 and/or ORF24-ORF27 and/or pUL50-pUL53 heterodimer interaction to be exploited for novel antiviral strategies for Herpesviridae, and specifically for HHV-1 to HHV-8 and/or PrV, or the like, in particular in betaherpesviruses. This new mechanism is based on the phosphorylation of the NEC protein pUL50, which could be masked/blocked/shielded by small molecules without being necessarily a cellular protein kinase.

The inhibition of cellular protein kinases (especially those with an essential or at least very important cellular function) for the purpose of antiviral strategy is often under controversial debate, since an inhibition of cellular kinases could result in cytotoxic, antiproliferative, cell-cycle-dysregulating or otherwise cell-inhibitory side effects.

In another embodiment of the instant invention, this problem might be resolved by a screening method of the invention for agents/compounds/small molecules with putative activity as the above-mentioned phospho-site blocker (PSB).

With the previously published Rechter et al., 2009, a CDK inhibitor R25 was described that inhibited the core NEC. R25 was found to block the NEC recruitment to the nuclear rim. This was shown in both with (i) with plasmid-transfected cells and (ii) with HCMV infected cells.

These inhibition data for the compound R25 (R25 tested in the confocal-microscopy test and with the co-immunoprecipitation as disclosed herein), may suggest that the now identified phospho-sites (see above) may be a trigger for a putative conformational change of pUL50 by phosphorylation, which is a precondition of hooking the N-terminal hook structure of pUL53 into pUL50 to form the core NEC as disclosed herein in detail. Without phosphorylation at these sites evidently pUL50 does not result in an active conformation and thus is not capable to interact with pUL53, despite the presence of the completely folded hook structure of pUL53 FIGS. 1 and 2), as disclosed herein.

Hence, the phospho-site inhibition of NEC polypeptides, such as pUL50, as described above, appears to also inhibit pUL53 recruitment to promote nuclear egress complex multimerization in general. This results in the absence of an annular "rim-like" colocalization of the heterodimer pUL50-pUL53 at the nuclear envelope/nuclear lamina of/the nuclear rim. Thus, the formation of the entire multimeric NEC from many viral and cellular proteins that are subsequently recruited into the NEC complex may be hereby inhibited (see e.g. FIGS. 3 and 6 for illustrations thereof).

It appears promising that CDKs are the first candidates for cellular protein kinases that phosphorylate the viral core NEC and thus activate virion maturation within HCMV. By analogy and homology as disclosed herein in the FIG. 4 SEQ ID NOs:, this situation could be similar in other viruses within the group of Herpesviridae.

Advantages of the Invention

In view of the outlined invention above, the core of the invention and the advantages can be summarized as follows:

The inventors disclose the BFRF1-BFLF2 and pUL50-pUL53 NEC crystal structure in a very detailed manner with high resolution.

In contrast to the prior art, the inventors expressed a truncated pUL50-pUL53 spanning the aa 1-171 fused via a linker, e.g., a glycine-rich linker, such as GGSGSGGS or the like, to pUL53 of amino acids 59-87 (see SEQ ID NOs: 1 and 2). The aa 59-87 have, according to the best knowledge of the inventors, not been analyzed for its detailed crystal structure, so far. The new crystal structure is available at 1.48 Å.

Similarly, a truncated EBV BFRF1-BFLF2 fusion protein was constructed, wherein EBV BFRF1 1-192 is fused via a linker, e.g., a glycine-rich linker, such as GGSGS or the like to EBV BFLF2 78-110 (see SEQ ID NOs: 3 and 4). The aa 78-110 have, according to the best knowledge of the inventors, not been analyzed for its detailed crystal structure, so far. The new crystal structure was provided at 1.75 Å (see FIG. 12 for illustration).

The inventors found a similar structure in HCMV and in EBV using the above fusion proteins. Therefore, as the structure seems to be conserved among different types of viruses of the Herpesviridae, it is possible to identify compounds affecting the NEC, e.g. Pan Herpes-inhibitors/modulators or the like, provided that these viruses use a NEC for viral replication and virion egress.

The inventors co-expressed the pUL50 and pUL53 of HCMV and BFRF1 and BFLF2 of EBV and the respective proteins of VZV and afterwards co-crystallized and co-purified these.

In is a further key advantage of the present invention, that four specific phospho-sites in pUL50 were identified and can be exploited either alone or in combination in the screening methods of the invention to modulate/inhibit/affect the NEC formation/multimerization of the NEC of viruses of the Herpesviridae in general, and specifically HHV-1 to HHV-8, for betaherpesviruses, such as HCMV and others.

The phospho-sites may be druggable targets, either as second line strategy or to be combined with the findings for the hook-like mechanism for pUL50 and pUL53, while being inhibited either alone or in combinations thereof. As another advantage of the invention this also provides for novel antiviral strategies for viruses selected from the group of Herpesviridae, such as the species HHV-1 to HHV-8, PrV, or the like and its respective strains. It is noted that the phospho-sites are all outside the interaction surface region of pUL50-pUL53 in HCMV NEC.

In view of the above, further and particularly preferred embodiments of the invention can be derived from the following consecutively numbered embodiments:

1. A polypeptide comprising at least two fused domains, wherein a first domain comprises a polypeptide comprising amino acid residues 1 to 171 according to SEQ ID NO: 1 or according to SEQ ID NO: 2, or a homologue thereof, and wherein a second domain comprises a polypeptide comprising amino acid residues 180 to 413 according to SEQ ID NO: 1 or amino acid residues 180 to 208 according to SEQ ID NO: 2, or a homologue thereof.

2. A polypeptide comprising at least two fused domains, wherein a first domain comprises a polypeptide comprising amino acid residues 1 to 192 according to SEQ ID NO: 3 or according to SEQ ID NO: 4, or a homologue thereof, and wherein a second domain comprises a polypeptide comprising amino acid residues 198 to 438 according to SEQ ID NO: 3 or amino acid residues 198 to 230 according to SEQ ID NO: 4, or a homologue thereof.

3. A polypeptide comprising at least two fused domains, wherein a first domain comprises a polypeptide comprising amino acid residues 1 to 174 according to SEQ ID NO: 5 or according to SEQ ID NO: 6, or a homologue thereof, and wherein a second domain comprises a polypeptide comprising amino acid residues 183 to 439 according to SEQ ID NO: 5 or amino acid residues 183 to 215 according to SEQ ID NO: 6, or a homologue thereof.

4. The polypeptide according to any one of embodiments 1 to 3, wherein at least one additional amino acid sequence is inserted between the first and second domain, or between respective homologues thereof.

5. The polypeptide according to any one of embodiments 1 or 4, wherein the first domain comprises a polypeptide comprising amino acid residues 1 to 171 according to SEQ ID NO: 1 or according to SEQ ID NO: 2, or a homologue thereof, corresponds to, or is part of, human cytomegalovirus protein pUL50 comprising amino acid residues 1 to 171 according to SEQ ID NO: 1 or according to SEQ ID NO: 2, or a homologue thereof, and wherein the second domain comprising amino acid residues 180 to 413 according to SEQ ID NO: 1 or amino acid residues 180 to 208 according to SEQ ID NO: 2 corresponds to, or is part of, human cytomegalovirus protein pUL53, or a homologue thereof.

6. The polypeptide according to embodiment 2 or 4, wherein the first domain comprising amino acid residues 1 to 192 according to SEQ ID NO: 3 or according to SEQ ID NO: 4 corresponds to, or is part of, Epstein-Barr virus protein BFRF1 or a homologue thereof, and wherein the second domain comprising amino acid residues 198 to 438 according to SEQ ID NO: 3 or amino acid residues 198 to 230 according to SEQ ID NO: 4 corresponds to, or is part of, Epstein-Barr virus protein BFLF2 or a homologue thereof.

7. The polypeptide according to embodiment 3 or 4, wherein the first domain comprising amino acid residues 1 to 174 according to SEQ ID NO: 5 or according to SEQ ID NO: 6 corresponds to, or is part of, Varizella Zoster Virus protein VZV ORF24 or a homologue thereof, and wherein the second domain comprising amino acid residues 183 to 439 according to SEQ ID NO: 5 or amino acid residues 183 to 215 according to SEQ ID NO: 6 corresponds to, or is part of, Varizella Zoster Virus protein VZV ORF27 or a homologue thereof.

8. The polypeptide according to anyone of embodiments 1, 4 and 5 comprising the amino acid sequence according to SEQ ID NOs: 1 or 2 or a homologue thereof.

9. The polypeptide according to anyone of embodiments 2, 4 and 6 comprising the amino acid sequence according to SEQ ID NOs: 3 or 4 or a homologue thereof.

10. The polypeptide according to anyone of embodiments 3, 4 and 7 comprising the amino acid sequence according to SEQ ID NOs: 5 or 6 or a homologue thereof.

11. Use of a polypeptide as defined in any one of embodiments 1 to 10 as screening tool.

12. Antibody or antibody fragment or IgG scaffold or non-IgG scaffold specifically binding to the polypeptide of any one of embodiments 1 to 10 or a homologue thereof.
13. A method for screening agents that specifically bind to and/or interact with and/or antagonize the polypeptides as defined in any of embodiments 1 to 10 or homologues thereof, comprising the steps of:
   a) providing a reaction system in vitro,
   b) providing at least one polypeptide as defined in any one of embodiments 1 to 10 or a homologue thereof as polypeptide target,
   c) mixing at least one candidate agent,
      wherein either said polypeptide target or said candidate agent or both said polypeptide target and said candidate agent are optionally labelled with a detectable label selected from the group comprising a radioisotope, a chemiluminescent label, a fluorescent label, a bioluminescent label, a peptide, or an enzyme, and
   d) detecting binding and/or interaction of and/or antagonization of said polypeptide target and said candidate agent by monitoring functional and/or structural changes in at least one polypeptide according to any one of SEQ ID NOs: 1 to 6 or a homologue thereof and/or in the candidate agent binding to and/or interacting with and/or antagonizing said polypeptide target or a homologue thereof,
      wherein functional and/or structural changes in the at least one polypeptide target or a homologue thereof and/or increased binding and/or interaction and/or antagonization between said at least one polypeptide target and said candidate agent relative to a control without said candidate agent is indicative of activity of the candidate agent in affecting and/or conformationally influencing said at least one polypeptide target, or a homologue thereof.
14. The method of embodiment 13, wherein said method is selected from the group comprising an immunoprecipitation assay, a microscopy-based assay, a peptide binding assay, an NMR-based assay, an X-ray assay, an in silico assay, an inhibition assay, an immunoassay, and/or a cellular assay.
15. An in silico method of structurally screening agents that specifically bind to and/or interact with and/or antagonize the polypeptides as defined in any one of embodiments 1 to 10, comprising the steps of:
   a) providing crystal structure data of at least one polypeptide as defined in any one of embodiments 1 to 10, or a homologue thereof, as polypeptide target,
   b) calculating whether at least one candidate agent of known structure specifically binds to and/or interacts with and/or antagonizes the polypeptide target, or a homologue thereof.
16. A method of computer-assisted identification of a compound that modulates an activity of a target protein, the method comprising:
   a) providing a crystal structure of at least one target polypeptide as defined in any one of embodiments 1 to 10, or a homologue thereof, in complex with a biomolecule, or a fragment thereof,
   b) performing a long timescale molecular dynamics simulation of the structure,
   c) identifying one or more evolved three dimensional topological features of the target polypeptide of the structure of step a), and
   d) identifying a compound that binds to at least one of the one or more evolved three dimensional topological features identified in step c), wherein binding of the compound to the one or more evolved three dimensional topological features modulates an activity of the target protein.
17. A method of computer-assisted identification of a compound that modulates an interaction between a target polypeptide and a biomolecule, wherein the biomolecule is a binding partner of the target polypeptide, the method comprising:
   a) providing a crystal structure of at least one target polypeptide as defined in anyone of embodiments 1 to 10, or a homologue thereof, in complex with a biomolecule, or a fragment thereof,
   b) performing a long timescale molecular dynamics simulation of the structure,
   c) identifying one or more evolved three dimensional topological features of the target polypeptide of the structure of step a), and
   d) identifying a compound that binds to at least one of the one or more evolved three dimensional topological features identified in step c) wherein binding of the compound to the one or more evolved three dimensional topological features modulates an interaction between the target polypeptide and the biomolecule or fragment thereof.
18. An in vitro method of identifying biologically active agents that reduce virus replication in cells, wherein said virus is a herpesvirus selected from the group of Herpesviridae, said method comprising:
   a) combining a biologically active candidate agent selected from the group comprising polypeptides, proteins, protein fragments, antibodies, antibody fragments, IgG scaffolds, non-IgG scaffolds, peptides, peptide fragments, nucleic acids, ribonucleic acids, RNAi, small molecules, in silico designed small molecules, further characterized in that said biologically active candidate agent is binding to and/or interacting with and/or antagonizing a target polypeptide as defined in any one of embodiments 1 to 10 or a respective homologue thereof, with at least one cell that is infected with said virus, and
   b) determining the effect of said biologically active candidate agent on virus replication.
19. The method of any one of embodiments 13 to 18, wherein said candidate agent is selected from the group comprising polypeptides, proteins, protein fragments, antibodies, antibody fragments, IgG scaffolds, non-IgG scaffolds, peptides, peptide fragments, nucleic acids, ribonucleic acids, RNAi, small molecules and in silico designed small molecules.
20. The method of any one of embodiments 13 to 19, further comprising varying the amount of candidate agent in said reaction system.
21. The method of any one of embodiments 13 to 20, wherein said herpesvirus is Epstein-Barr Virus or Varizella Zoster Virus or HCMV.
22. Antibody or antibody-fragment or IgG-scaffold or non-IgG scaffold that specifically binds to the polypeptides of any one of embodiments 1 to 10 or to homologues thereof.
23. Antibody or antibody-fragment or IgG-scaffold or non-IgG scaffold according to the embodiment 22, wherein said antibody or antibody-fragment is selected from the group comprising Fv fragments, scFv fragments, Fab fragments, scFab fragments, F(ab)2 fragments and scFv-Fc Fusion proteins.

24. Antibody or antibody-fragment or IgG-scaffold or non-IgG scaffold according to embodiments 22 and 23, wherein said antibody or antibody fragment is a monoclonal antibody, an affinity-purified polyclonal antibody or a combination of monoclonal and affinity-purified polyclonal antibodies.

25. Antibody or antibody-fragment or IgG-scaffold or non-IgG scaffold according to any of embodiments 22 to 24 for use in methods of treatment of viral infectious diseases mediated by the group of Herpesviridae, in particular by the group of betaherpesviruses, or by the gammaherpesviruses, particularly EBV.

26. Antibody or antibody-fragment or IgG-scaffold or non-IgG scaffold according to any of embodiments 22 to 25, for use in methods of treatment of viral infectious diseases mediated by the group of betaherpesviruses, e.g., by the group of cytomegaloviruses.

27. Antibody or antibody-fragment or IgG-scaffold or non-IgG scaffold according to any of embodiments 22 to 26, for use in methods of treatment of viral infectious diseases mediated by HCMV.

28. A method for screening agents that specifically bind to and/or interact with and/or antagonize the polypeptides according to any one of embodiments 1 to 10 or homologues thereof, comprising the steps of:
   a) providing a reaction system in vitro,
   b) providing at least one of the above mentioned polypeptides according to any one of embodiments 1 to 10 or homologues thereof as protein target, and
   c) admixing at least one candidate agent,
wherein either said protein target or said candidate agent or both, said protein target and said candidate agent, are optionally labeled with a detectable label selected from the group comprising a radioisotope, a chemiluminescent molecule, a bioluminescent molecule, a fluorescent molecule, a peptide, or an enzymatic label, and
   d) detecting binding and/or interaction and/or antagonization between said protein target and said candidate agent by monitoring functional and/or structural changes in the protein target or a homologue thereof and/or in the candidate agent binding and/or interacting with and/or antagonizing said protein target or a homologue thereof,
wherein functional and/or structural changes in the protein target or a homologue thereof and/or an increased binding and/or interaction and/or antagonization of said protein target and candidate agent relative to a control without said candidate agent is indicative of activity of the candidate agent in affecting and/or inhibiting the protein or a homologue thereof.

29. A method of identifying an agent that specifically binds to and/or interacts with and/or antagonizes the polypeptides of any one of embodiments 1 to 10 or a homologue thereof, comprising the following steps:
   a) providing a reaction system in vitro,
   b) (i) providing at least one NEC or a homologue thereof comprising a polypeptide referred to in any one of embodiments 1 to 10 or a homologue thereof as protein target, or (ii) providing a polypeptide referred to in any one of embodiments 1 to 10 or a homologue thereof as polypeptide target, and
   c) admixing at least one candidate agent, and further
   d) admixing either simultaneously or consecutively said at least one of the polypeptides of any one of embodiments 1 to 10 or a homologue thereof,
wherein either said protein target or said candidate agent or both, said polypeptide target and said candidate agent or both, are optionally labeled with a detectable label selected from the group comprising a radioisotope, a chemiluminescent molecule, a bioluminescent molecule, a fluorescent molecule, a peptide, or an enzymatic label, and
   e) detecting binding and/or interaction and/or antagonization between said protein target and said candidate agent or said polypeptide target and said candidate agent by monitoring functional and/or structural changes in the heterodimerization of a polypeptide referred to in any of embodiments 1 to 10 or of homologues thereof, respectively,
wherein a reduced binding and/or interaction and/or antagonization during heterodimerization in the presence of said candidate agent relative to a control without said candidate agent is indicative of activity of the candidate agent in affecting and/or inhibiting the heterodimerization.

30. The method of any of embodiments 28 and 29, wherein said candidate agent is selected from the group comprising proteins, protein fragments, antibodies, antibody fragments, IgG-scaffolds, non-IgG scaffolds, peptides, peptide fragments, nucleic acids, ribonucleic acids, RNAi, small molecule(s) and in silico designed small molecules.

31. The method of any one of embodiments 28 to 30, further comprising varying the amount of the candidate agent in said reaction system.

32. The method of any one of embodiments 28 to 31, wherein the source for the reaction system is a cell, optionally infected with viruses selected from the group of Herpesviridae, in particular the betaherpesviruses, or selected from a group of EBV and/or VZV and/or CMV strains, more preferably selected from the group of HCMV strains, either expressing polypeptides according to any one of embodiments 1 to 10 or homologues thereof, and wherein a cell contacted with the candidate agent and a corresponding cell expressing polypeptides according to any one of embodiments 1 to 10 or homologues thereof, is not contacted with said candidate agent.

33. The methods of any one of the embodiments 28 to 32, wherein said detecting step is carried out using a kinase assay or a surrogate assay.

34. The method of any one of the embodiments 28 to 33, wherein said detecting step is carried out using an anti-Herpesviridae assay or a surrogate assay.

35. The method of the embodiments 28 to 34, wherein said detecting step is carried out using an anti-EBV, an anti-VZV, and/or an anti-CMV assay or a surrogate assay.

36. The method of embodiment 35, wherein said detecting step is carried out using an anti-EBV, an anti-VZV, and/or an anti-HCMV assay or a surrogate assay.

37. The method of any one of embodiments 28 to 34, wherein said detecting step is carried out using an anti-HSV assay or a surrogate assay.

38. A method for identifying biologically active agents that inhibit virus replication in viruses selected from the group of Herpesviridae, in particular the group of betaherpesviruses, and/or by EBV, VZV, and/or CMV, more preferably by HCMV, the method comprising:
   a) combining a biologically active candidate agent selected from the group comprising proteins, protein fragments, antibodies, antibody fragments, IgG-scaffolds, non-IgG scaffolds, peptides, peptide fragments, nucleic acids, ribonucleic acids, RNAi, small molecule(s) and in silico designed small molecules, further characterized in that said candidate biologically active agent is binding to and/or interacting with and/or antagonizing the polypeptide according to any one of embodiments 1 to 10 or a homologue thereof as target, with at least one cell that is at least permissive for virus infections by viruses of the group of the Herpesviridae, in particular by the group of betaherpesviruses, and/or by EBV, VZV, and/or CMV, more preferably by HCMV and/or is infected with viruses of the group of the Herpesviridae, in particular by the group of betaherpesviruses in vitro, and/or by EBV, VZV, and/or CMV, more preferably by HCMV, and b) determining the effect of said candidate biologically active agent on viral capsid export from the cellular nucleus into the cytoplasm.

39. An immunoassay method for determining the binding of an antibody or antibody fragment or IgG-scaffold or non-IgG scaffold to the polypeptide according to any one of embodiments 1 to 10 or a homologue thereof as target, comprising:
    a) contacting an in vitro sample with at least one antibody or antibody fragment of IgG-scaffold or non-IgG scaffold, which specifically binds to an immunoreactive portion of said polypeptide according to any of the embodiments 1 to 10 or a homologue thereof as target, and
    b) determining the amount of bound antibody or antibody fragment or IgG-scaffold or non-IgG scaffold.

40. The method of embodiment 39, wherein said antibody or antibody fragment is a monoclonal antibody, an affinity-purified polyclonal antibody or a combination of monoclonal and affinity-purified polyclonal antibodies or fragments thereof.

41. The method of any one of embodiments 39 to 40, further comprising a second antibody which specifically binds to an immunoreactive portion of the polypeptide according to any one of embodiments 1 to 10 or of homologues thereof, which is different from the immunoreactive portion to which the first antibody binds, and wherein at least one antibody comprises a detectable label selected from the group comprising a radioisotope, a chemiluminescent molecule, a bioluminescent molecule, a fluorescent molecule, a peptide, or an enzymatic label.

42. The method of embodiment 41, wherein said first and second antibodies or fragments thereof are both monoclonal antibodies, both affinity-purified polyclonal antibodies or a combination of monoclonal and affinity-purified polyclonal antibodies or fragments thereof.

43. The methods of any one of embodiments 39 to 42, wherein said antibody is selected from the group comprising Fv fragment, scFv fragment, Fab fragment, scFab fragment, F(ab)2 fragment and scFv-Fc Fusion protein.

44. The methods of any one of embodiments 39 to 43, wherein the determination is carried out using a sandwich assay.

45. A confocal microscopy-based screening method for identifying agents that specifically bind to and/or interact with and/or antagonize a polypeptide according to any one of embodiments 1 to 10 or a homologue thereof as target, which comprises the following steps:

a) producing a polypeptide heterodimer according to any one of embodiments 1 to 10 or a homologue thereof by transfection of at least one expression construct encoding said polypeptide according to any one of embodiments 1 to 10 or homologues thereof in at least one cell, either
    a 1) in the absence of respective virus infection of said cell, or
    a 2) in virus-infected cells, or
    a 3) in a respective virus permissive cell, and
b) admixing simultaneously or consecutively a candidate agent selected from the group comprising proteins, protein fragments, antibodies, antibody fragments, IgG-scaffolds, non-IgG scaffolds, peptides, peptide fragments, nucleic acids, ribonucleic acids, RNAi, small molecule(s), and/or in silico designed small molecules with said cell(s), and
c) double-staining said polypeptides according to any one of embodiments 1 to 10 or homologues thereof of step a) by indirect immunofluorescence, and
d) determining the formation of the heterodimer of the respective polypeptides according to any one of embodiments 1 to 10 or of homologues thereof on the nuclear rim in said cells, and
e) correlating an annular co-localization of said polypeptides according to any one of embodiments 1 to 10 or homologues thereof of step a) with a specific binding and/or interaction and/or antagonization of the candidate agent of step b).

46. A co-immunoprecipitation-based screening method for identifying agents that specifically bind to and/or interact with and/or antagonize the polypeptide according to any one of embodiments 1 to 10 or a homologue thereof as target, which comprises the following steps:
    a) producing a polypeptide according to any one of embodiments 1 to 10 or a homologue thereof by transfection of at least one expression construct encoding said polypeptide according to any one of embodiments 1 to 10 or a homologue thereof in a cell, either
        a 1) in the absence of herpesvirus infection, or
        a 2) in herpesvirus-infected cells, or
        a 3) in a herpesvirus permissive cell,
    b) admixing simultaneously or consecutively a candidate agent selected from the group comprising proteins, protein fragments, antibodies, antibody fragments, IgG-scaffolds, non-IgG scaffolds, peptides, peptide fragments, nucleic acids, ribonucleic acids, RNAi, small molecule(s) and in silico designed small molecules to said cell(s), and
    c) detecting the interaction of polypeptides according to any one of embodiments 1 to 10 or homologues thereof by co-immunoprecipitation.

47. A method for screening agents that specifically bind to and/or interact with and/or antagonize the phospho-site(s) of a polypeptide according to any one of embodiments 1 to 10 or a homologue thereof as target, comprising the steps of:
    a) providing a reaction system in vitro,
    b) providing i) either at least one polypeptide according to any one of embodiments 1 to 10 or a homologue thereof as protein target, or ii) a heterodimer of a polypeptide according to any one of embodiments 1 to 10 or a homologue thereof as protein target, and
    c) admixing at least one candidate agent,
    whereby either said protein target or said candidate agent or both said protein target and said candidate agent are optionally labeled with a detectable label selected from the group comprising a radioisotope, a chemiluminescent molecule, a bioluminescent molecule, a fluorescent molecule, a peptide, or an enzymatic label, and d) detecting binding and/or interacton with and/or antagonization of said phospho-site(s) of said protein target and said candidate agent by monitoring functional and/or structural changes in the protein target, wherein an increased binding and/or interaction with and/or antagonization of said phospho-site(s) of a polypeptide according to any one of embodiments 1 to 10 or a homologue thereof as protein target and the candidate agent relative to a control without said candidate agent is indicative of activity of the candidate agent in affecting and/or inhibiting the polypeptide according to any one of embodiments 1 to 10 or a homologue thereof.

48. A method for screening agents that specifically mask and/or shield and/or block at least one phospho-site of embodiment 47 as target, comprising the steps of:
    a) providing a reaction system in vitro,
    b) providing either at least one or more phospho-site(s) of a polypeptide according to any one of embodiments 1 to 10 or a homologue thereof as protein target, and
    c) admixing at least one candidate agent, whereby either said protein target or said candidate agent or both said protein target and said candidate agent are optionally labeled with a detectable label selected from the group comprising a radioisotope, chemiluminescent molecule, bioluminescent molecule, fluorescent molecule, peptide or enzymatic label, and
    d) detecting masking and/or shielding and/or blocking of said phospho-site protein target and said candidate agent by monitoring functional and/or structural changes in the phospho-site(s) of a polypeptide according to any one of embodiments 1 to 10 or a homologue thereof, wherein an increased binding and/or interaction between said phospho-site(s) of a polypeptide according to any one of embodiments 1 to 10 or a homologue thereof as protein target and said candidate agent relative to a control without said candidate agent is indicative of effective masking and/or shielding and/or blocking activity of the candidate agent of the phospho-site(s) tested of a polypeptide according to any one of embodiments 1 to 10 or a homologue thereof.

49. Use of a polypeptide or a homologue thereof according to any one of embodiments 1 to 10 for identifying agents that modulate or inhibit functionally and/or structurally the NEC or homologues thereof.

50. Use of a polypeptide or a homologue thereof according to any one of embodiments 1 to 10 for identifying agents that modulate or inhibit functionally and/or structurally the heterodimerization of NEC or homologues thereof.

51. Use of a polypeptide or a homologue thereof according to any one of embodiments 1 to 10 for identifying agents in vitro that modulate or inhibit functionally and/or structurally the heterodimerization of NEC in viruses of the family of Herpesviridae.

52. Use according to embodiment 51 for identifying agents in vitro that modulate or inhibit functionally and/or structurally the the heterodimerization of NEC in CMV, in particular in HCMV.

53. Nucleic acid sequence encoding a polypeptide according to any one of SEQ ID NOs: 1 to 6 or a homologue of any one of these.

54. A vector containing the nucleic acid sequence according to embodiment 53.

55. Host cell genetically engineered with the vector according to embodiment 54.

56. A method of designing a common sequence, particularly a common hook sequence forming part of the nuclear egress complex (NEC) in viruses of the family of Herpesviridae, particularly human cytomegalovirus (HCMV), Epstein-Barr virus (EBV), and/or varicella zoster virus (VZV), comprising the following steps:
    Calculating the energetic contributions of individual amino acid side chains of a polypeptide as defined in any one of embodiments 1 to 10;
    Determining similarities of the energy profiles of the hook sequences in the polypeptides by sub-steps comprising (a) replacement of one or more or each of the amino acid residues in each hook by another amino acid and (b) measuring the interaction energy with corresponding autologous or non-autologous herpesvirus groove proteins of at least one or more of the above polypeptides, wherein optionally negative values of the interaction energy is indicative of increased affinity compared to the wild-type amino acid residue;
    Molecular modelling of a common sequence using molecular dynamics simulation.

57. Use of the common sequence obtainable in a method according to embodiment 56 for identifying agents that modulate or inhibit functionally and/or structurally the heterodimerization of NEC or homologues thereof, particularly in viruses of the family of Herpesviridae, for identifying agents in vitro that modulate or inhibit functionally and/or structurally the the heterodimerization of NEC in CMV, in particular in HCMV.

It is to be understood that this invention is not limited to the particular methodologies, particular assays, protocols, and reagents described may vary. It is also to be understood that the terminology used herein is for the purpose of describing particular embodiments only, and is not intended to limit the scope of the present invention.

It must be noted that as used herein and in the appended claims, the singular forms "a" and "the" or the like include plural referents unless the context clearly dictates otherwise. Thus, for example, reference to "a homologue thereof" includes a plurality of such reasonable homologues known to those skilled in the art, and so forth.

It is noted that the term "comprising" also encompasses the meaning "consisting of", e.g., a group of members comprising said members also encompasses a group of members consisting only of these members.

Unless defined otherwise, all technical and scientific terms used herein have the same meaning as commonly understood to one of ordinary skill in the art to which this invention belongs.

Although any methods, assays, devices, programs and materials similar or equivalent to those described herein can be used in the practice or testing of the invention, the preferred screening methods/assays, devices, programs and materials are described herein.

Definitions

The expressions "druggability" and "druggable" or related terms denote with the subject matter of the present invention a biological target (i.e. within the context of the invention pUL50 and/or pUL53 protein, -protein fragment, -peptide, -peptide fragment or the peptide of SEQ ID NO: 1 and/or the identified phospho-sites disclosed herein) that was found by the inventors and is predicted to bind with high affinity to a drug. Furthermore by definition within the context of the invention, the binding of a drug that is obtainable by the screening methods/assay of the present invention will alter the function/structure of the target with a therapeutic benefit to the patient. The concept of drug-gability in context of the invention is preferably directed to small molecules, but also comprises biologic medical products such as therapeutic monoclonal antibodies.

The expression "small molecule(s)" and related terms with the context of the invention denote low molecular weight molecules that comprise lipids, monosaccharides, second messengers, other natural products and metabolites, as well as drugs and other xenobiotics, but not limited thereto. They are distinct from macromolecules such as proteins. These or similar expressions cover metal ions.

In molecular biology and pharmacology, a small molecule is a low molecular weight (<900 daltons) organic compound that may help regulate a biological process, with a size on the order of $10^{-9}$ m. Most drugs are small molecules.

The upper molecular weight limit for a small molecule is approximately 900 daltons, which allows for the possibility to rapidly diffuse across cell membranes so that they can reach intracellular sites of action. In addition, this molecular weight cutoff is a necessary but insufficient condition for oral bioavailability. Finally, a lower molecular weight cutoff of 500 daltons (as part of the "rule of five") has been recommended for small molecule drug development candidates based on the observation that clinical attrition rates are significantly reduced if the molecular weight is kept below this 500 dalton limit.

Pharmacology usually restricts the term to a molecule that binds to a specific biopolymer such as protein or nucleic acid and acts as an effector, altering the activity or function of the biopolymer. Small molecules can have a variety of biological functions, serving as cell signaling molecules, as drugs in medicine, as pesticides in farming, and in many other roles. These compounds can be natural (such as secondary metabolites) or artificial (such as antiviral drugs); they may have a beneficial effect against a disease (such as drugs) or may be detrimental (such as teratogens and carcinogens). Biopolymers such as nucleic acids and proteins, and polysaccharides (such as starch or cellulose) are not small molecules though their constituent monomers ribo- or deoxyribonucleotides, amino acids, and monosaccharides, respectively are often considered small molecules. Very small oligomers are also usually considered small molecules, such as dinucleotides, peptides such as the antioxidant glutathione, and disaccharides such as sucrose.

Small molecules may also be used as research tools to probe biological function as well as leads in the development of new therapeutic agents. Some can inhibit a specific function of a multifunctional protein or disrupt protein-protein interactions.

The term "inhibit" or similar terms with the context of the invention denote(s) to restrain, hinder, or arrest an action, a structure, a function, an impulse, etc. and/or to prohibit an action, a structure, a function, an impulse, etc. within the context of the invention. Said term or similar terms also denote(s) to decrease the rate of action of or stop a chemical, biochemical, physical, or physico-chemical reaction.

The term "antagonize" or similar terms with the context of the invention denote(s) to act in opposition to something or against something within the context of the present invention.

The term "homologue" or similar terms denote(s) DNA, RNA, amino acid(s), protein/peptide or fragment analogs that are equal or similar in structure and function; see e.g. FIG. 4 for illustration thereof.

The term "Herpesviridae" denotes a viral/virus family, comprising different genera such as e.g. the genus CMV and other genus, the person skilled in the art is aware of. Within a genus different viral/virus species exist, such as within the genus CMV, the human pathogen HCMV and the murine pathogen MCMV exist. Such species further comprise different strains such as for instance HCMV, the strain AD169. Furthermore, with the context of the invention, the person skilled in the art knows how to discriminate between animal pathogens and human pathogens. For instance the skilled person is well aware that HCMV is predominantly a human pathogen and MCMV is predominantly a murine pathogen. Furthermore, the person skilled in the art is aware that e.g. HHV-6, HHV-7, HHV-8 represent an own class of viruses.

The term "target" or similar terms within the context of the invention denote(s) a structure of a protein/polypeptide/peptide or a fragment thereof or an amino acid or more amino acids to be tested for binding/interacting with/antagonizing with the compounds/agents/small molecules by the disclosed screening methods/assays of the instant invention. This definition can be combined with the definition for "druggable" above to define a "druggable target" with the context of the instant invention.

The expression "long timescale molecular dynamics simulation" and variations thereof is known in the art (e.g., from "Long-timescale molecular dynamics simulations of protein structure and function", Literature Review in Current Opinion in Structural Biology 19 (2): 120-7. May 2009).

Abbreviations

The abbreviations used within the context of the instant invention are:
aa—amino acid(s)
CoIP—coimmunoprecipitation
CMV—cytomegalovirus
CR—conserved region
HCMV—human cytomegalovirus
GHKL—ATPase/kinase superfamily
HSV-1—herpes simplex virus type 1
IMAC—immobilized metal ion affinity chromatography
INM—inner nuclear membrane
MCMV—murine cytomegalovirus
NEC—nuclear egress complex
ONM—outer nuclear membrane
ORF—open reading frame
PCR—polymerase chain reaction
PKC—protein kinase C
VZV—varizella-zoster-virus
HSV—herpes simplex virus
HHV—human herpesvirus
EBV—Epstein-Barr-virus
PrV—pseudorabies virus (member of herpesviruses)

EXAMPLES

1. Protein Production and Purification.

The proteins corresponding to SEQ ID NO: 1 to 6 were cloned into either the plasmid pET15b or pET28b. By doing so, the viral protein sequences are N-terminally expanded to include a His-tag and Thrombin cleavage site MGSSHHHHHHSSGLVPRGSH sequence (SEQ ID NO: 40) at the N-terminus to make the production and purification of the fusion proteins easier. The plasmids were transformed into *E. coli* BL21 (DE3) and the cells incubated in TB-medium in the presence of either 100 µg/ml ampicillin or 50 µg/ml kanamycin at 20° C. Protein production was induced with 0.25 to 1 mM IPTG. After cell harvesting and cell disruption using a sonicator or high pressure homogenizer, all protein were purified using a HisTrap affinity chromatography step. The proteins were subsequently cleaved using thrombin. As a result of this step, the purified viral fusion proteins start with a GSH sequence appended to their N-terminus. The proteins were then further purified using a gel filtration chromatography step and depending on the presence of additional contaminants with an additional ion exchange chromatography step.

2. Protein Crystallization.

The two fusion proteins truncated-HCMV-pUL50-pUL53 fusion protein (SEQ ID NO: 2) and truncated-EBV-BMRF1-BMLF2 fusion protein (SEQ ID NO: 4) were screened for crystallization conditions using the sitting drop technique and proteins with concentrations between 10 and 15 mg/ml dissolved in a buffer consisting of 50 mM TrisHCl buffer, 150 mM NaCl and pH 7.4. Diffraction quality crystals of truncated-HCMV-pUL50-pUL53 fusion protein (SEQ ID NO: 2) were obtained at 4° C. with 20% PEG 4000, 10% propanol, 100 mM HEPES, pH 7.5 as a reservoir solution. Diffraction quality crystals of truncated EBV BMRF1-BMLF2 fusion protein (SEQ ID NO: 4) were obtained at 4° C. with 0.2M sodium malonate pH 4.5, 20% PEG 3350 (Peg Rx E2) as a reservoir solution.

3. Crystal Structure Determination

High resolution diffraction data sets from crystals of truncated-HCMV-pUL50-PUL53 fusion protein (SEQ ID NO: 2) and truncated-EBV-BMRF1-BMLF2 fusion protein (SEQ ID NO: 4) were collected at the MX beamlines of the BESSY synchrotron Berlin. Data were processed with program XDS. Initial phases were obtained with the molecular replacement technique with program PHENIX_MRAGE using the previously determined structure of the pUL50-pUL53 complex as a search model (PDB entry code 5D5N.pdb). The structures were completed and corrected using either the PHENIX program AUTOBUILD or manually using program COOT. The structures were refined to convergence with program PHENIX.REFINE. Crystallographic data collection and refinement statistics are summarized below for truncated-HCMV-pUL50-pUL53 fusion protein (SEQ ID NO: 2) and truncated-EBV-BMRF1-BMLF2 fusion protein (SEQ ID NO: 4), respectively.

Data Collection and Refinement Statistics for Truncated-HCMV-pUL50-pUL53 Fusion Protein (SEQ ID NO: 2):

| Data Collection | BESSY II 14.2 |
| --- | --- |
| Wavelength (λ) | 0.9182 |
| Space Group | P 1 21 1 (4) |
| Cell abc (Å), αβγ (°) | 37.27 82.57 63.66, 90 95.1 90 |
| Resolution (Å) | 41.29-1.48 (1.57-1.48) |
| Mosaicity (°) | 0.068 |
| Unique reflections | 120737 |
| Multiplicity | 2.1 |
| $R_{sym}$ (%) | 6.5 (59.4) |
| Mean I/σI | 6.47 (1.06) |
| CC ½ | 99.1 (56.5) |
| Wilson B (Å²) | 25.74 |
| Completeness | 95.6 (94.8) |
| Refinement | |
| $R_{work}/R_{free}$ (%) | 18.8/22.5 |
| Molecules/ASU | 2 |
| Rama. outl./fav. (%) | 0.0/98.95 |
| Rotamer outl. (%) | 1.98 |
| RMS bonds/angles | 0.0096/1.05 |
| Atoms protein/solvent | 3120/241 |
| TLS groups | 4 |

Data Collection and Refinement Statistics for Truncated-EBV-BMRF1-BMLF2 Fusion Protein (SEQ ID NO: 4):

| Data Collection | BESSY II 14.2 |
| --- | --- |
| Wavelength (λ) | 0.9182 |
| Space Group | P6122 (178) |
| Cell abc (Å), αβγ (°) | 59.31 59.31 265.34, 90 90 120 |
| Resolution (Å) | 47.90-1.75 (1.83-1.75) |
| Mosaicity | 0.109 |
| Unique reflections | 22538 |
| Multiplicity | 37.4 |
| $R_{sym}$ (%) | 7.4 (187.5) |
| Mean I/σI | 29.3 (2.66) |
| CC ½ | 100.0 (89.0) |
| Completeness | 77.3 (31.4) spherical 94.0 (100.0) ellipsoidal |
| Refinement | |
| $R_{work}/R_{free}$ (%) | 21.4/25.0 |
| RMS Bonds (Å) | 0.007 |
| RMS Angles (°) | 1.002 |
| Molecules/ASU | 1 |
| Water molecules | 94 |
| Ramachandran outl. (%) | 1.36 |
| Ramachandran fav. (%) | 94.1 |
| RMS bonds (Å) | 0.007 |
| RMS angles (°) | 1.002 |

4. HCMV Replication Assay

The Suitability of the Agents/Compounds/Small Molecules of the Invention for the Treatment of HCMV infections can be exemplarily shown in the following animal model:—HCMV Xenograft Gelfoam®. The person skilled in the art is aware that similar suitable tests can be applied to test the agents/compounds/small molecules to be identified by the invention for, e.g., treatment of HHV-1-HHV-8, or PrV infections, but not limited thereto, such as for instance suitable anti-HSV, anti-HHV- or anti-VZV tests.

5. Animal Model-HCMV Xenograft Gelfoam®

3-4-week old female immunodeficient mice (16-18 g), Fox Chase SCID or Fox Chase SCID-NOD or SCID beige, are purchased from commercial breeders (Taconic M+B, Jackson USA). The animals are housed under sterile conditions (including bedding and feed) in isolators.

6. Virus Growing

Human cytomegalovirus (HCMV), Davis or AD169 strain, is grown in vitro on human embryonic prepuce fibroblasts (NHDF cells). After the NHDF cells have been infected with a multiplicity of infection (M.O.I.) of 0.01-0.03, the virus-infected cells are harvested 5-10 days later and stored in the presence of minimal essential medium (MEM), 10% fetal calf serum (FCS) with 10% DMSO at 40° C. After serial ten-fold dilutions of the virus-infected cells, the titer is determined on 24-well plates of confluent NHDF cells after vital staining with Neutral Red.

7. Preparation of the Sponges, Transplantation, Treatment and Evaluation:

Collagen sponges 1 cm×1 cm×1 cm in size (Gelfoam®; from Peasel & Lorey, order No. 407534; K. T. Chong et al., Abstracts of 39th Interscience Conference on Antimicrobial Agents and Chemotherapy, 1999, p. 439) are initially wetted with phosphate-buffered saline (PBS), the trapped air bubbles are removed by degassing, and then stored in MEM+10% FCS. 1×10$^6$ virus-infected NHDF cells (infection with HCMV Davis or HCMV AD169 M.O.I.=0.01) are detached 3 hours after infection and added in a drop of 20 μl of MEM, 10% of FCS, to a moist sponge. About 16 hours later, the infected sponges are incubated with 25 μl of PBS/0.1% BSA/1 mM DTT with 5 ng/μl basic fibroblast growth factor (bFGF). For the transplantation, the immunodeficient mice are anaesthetized with Avertin or a ketamine/xylazine/azepromazine mixture, the fur on the back is removed using a shaver, the epidermis is opened 1-2 cm, unstressed and the moist sponges are transplanted under the dorsal skin. The surgical wound is closed with tissue glue. 6 hours after the transplantation, the mice can be treated for the first time (on the day of the operation, there is one treatment).

The next days, over a period of 8 days, the mice are treated with substance orally three times a day (7.00 h and 14.00 h and 19.00 h), two times a day (8.00 h and 18.00 h) or once a day (14.00 h). The daily dose is, for example 3 or 10 or 30 or 60 or 100 mg/kg of body weight, but not limited thereto, the volume administered is 10 ml/kg of body weight. The substances are formulated in the form of a 0.5% strength Tylose suspension with 2% DMSO or a 0.5% strength Tylose suspension. 9 days after transplantation and 16 hours after the last administration of substance, the animals are painlessly sacrificed and the sponge is removed.

The virus-infected cells are released from the sponge by collagenase digestion (330 U/1.5 ml) and stored in the presence of MEM, 10% fetal calf serum, 10% DMSO at −140° C.

Evaluation takes place after serial ten-fold dilutions of the virus-infected cells by determining the titer on 24-well plates of confluent NHDF cells after vital staining with Neutral Red. The number of infected cells or infectious virus particles (infectious center assay) after the substance treatment compared with the placebo-treated control is determined.

8. CYP Inhibition Assay

To investigate the mechanism-based (irreversible) inhibition of CYP3A4, different concentrations of the test substance are incubated with human liver microsomes (2 mg/ml of microsomal protein) in potassium phosphate buffer pH 7.4 with addition of an NADPH-generating system (NADP+, glucose 6-phosphate, glucose 6-phosphate dehydrogenase) at 37° C. At various points of time, 2 aliquots are taken from the incubation.

The first aliquot is incubated 1:50 in a new incubation solution (phosphate buffer, NADPH-generating system and 10 μM of Midazolam) at 37° C. for a further 10 min. The incubation is then stopped using acetonitrile on ice, the protein is pelleted in a centrifuge at 15.000 g and the supernatant is analyzed for formation of 1'-hydroxymidazolam using standard HPLC/MS methods. The second aliquot is stopped using acetonitrile on ice and analyzed for remaining test substance using HPLC/UV/MS.

The two sets of analytical data are determined for irreversible-inhibition-typical parameters (kinact, Ki and partition ratio r), and using these data, the test substance is evaluated (cf. A. Madan, et al., in A. D. Rodrigues (ed.) "Drug-Drug Interaction" in "Drugs and the Pharmaceutical Science", Vol. 116, ISBN 0-8247-0283.2, Marcel Dekker Inc., New York, 2002). The person skilled in the art, as stated above, is aware that any suitable anti-HCMV assay or surrogate assay can be used as well as any suitable anti-HSV assay or surrogate assay or similar assays for the viral strains to be tested, to further investigate the antiviral properties of the candidate agents identified by the screening methods/assays disclosed herein.

Cloning of Viral Core NEC Proteins

Materials and Methods

Bacteria
*Escherichia coli* (*E. coli*) DH10B: F-endA1 hsdR17 (rk−, mk+) supE44 thi-1 λ-recA1 gyrA96 relA1 deoRΔ Δ(lacZYA-argF)-U169 80lacAM15 (Grant et al., 1990)

Eukaryotic Cell Cultures
 293T: human embryonic kidney epithelial cells (HEK), transformed by adenovirus type 5 (Ad5), additionally expressing the simian virus 40 (SV40) large tumor antigen (Pear et al., 1993)
 HeLa: human cervical carcinoma cell line, positive for the human papillomavirus type 16 (HPV-16) (Nelson-Rees and Flandermeyer, 1976)

Nucleic Acids

Oligonucleotides

The respective sequences (annotated from 5' to 3') used for PCR cloning, Gateway cloning and nucleotide sequencing are listed below. Sequences corresponding to the gene of interest are underlined, restriction enzyme cleavage sites are highlighted in bold, Flag (DYKDDDDK peptide, SEQ ID NO: 41) and HA (hemagglutinin) epitopes are depicted in italics and start and stop codons are shaded in grey.

Oligonucleotides Used for PCR-Cloning

| Storage number | Designation | Nucleotide sequence |
| --- | --- | --- |
| 52-60 | 5-UL53 (aa50) EcoRI | TAGGAATTCATGC CGTCGCCGGCCGA CGCGCGCCCGCGC CTCACGCTGCACG ACCTGCACGACAT CTTCCGCGAGCAC CCCGAACTGGAGC TC (SEQ ID NO. 42) |
| 52-61 | 3-UL53 (aa292)- Flag XhoI | TAG CTCGAG TCA *CTTGTCGTCATCG TCTTTGTAGTC* GCCGCTGGACTGA CACAGCTC (SEQ ID NO. 43) |
| 52-62 | 5-BFLF2 (aa73) EcoRI | TAG GAATTC ATG ACGGGACTTCTTCA GGGGAATCTCTGCC AACTTTGAGCTGGG CAAAG (SEQ ID NO. 44) |

-continued

| Storage number | Designation | Nucleotide sequence |
|---|---|---|
| 52-63 | 3-BFLF2 (aa318)-Flag XhoI | TAG CTCGAG TCA *CTTGTCGTCATCGT CTTTGTAGTC* CTGTTTATTTTC CAAAATGAGC (SEQ ID NO. 45) |
| 52-64 | 5-UL53 globular (aa88) with BFLF2 Hook (aa95) | TTTGAGCTGGGCAAA GATTTTCTGCGTGAG ATGAACACCCCATA CAT GGCAAAGAGTC CATC (SEQ ID NO. 46) |
| 52-65 | 5-BFLF2 Hook (aa95) with UL53 Hook (aa50) EcoRI | TAG GAATTC ATG CCGTCGCCGGCCGAC GCGCGCCCGCGCCTC ACGCTGCACGACCTG CACGACATCTTCCGC GAGCACTTTGAGCTG GGCAAAG (SEQ ID NO. 47) |
| 52-66 | 5-UL53 Hook (aa72) with BFLF2 Hook (aa73) EcoRI | TAG GAATTC ATG ACGGGACTTCTTCA GGGGAATCTCTGCC AACCCCGAACTGGA GCTC (SEQ ID NO. 48) |
| 52-67 | 5-BFLF2 globular (aa111) with UL53 Hook (aa72) | CCCGAACTGGAGCT CAAGTACCTTAACA TGATGAAGATGCC ATCACGGTCTCAGA GGCCGTGTTTC (SEQ ID NO. 49) |

Oligonucleotides Used for Gateway Cloning

| Storage number | Designation | Nucleotide sequence |
|---|---|---|
| M52-80 | 5-BFRF1 EcoRI attB1 | TAGGAATTCGGGG ACAAGTTTGTACAAA AAAGCAGGCT ACC ATG GCGAGCCCGGAAGAG (SEQ ID NO. 50) |
| M52-81 | 3-BFRF1-Linker BamHI | TAGGGATCCCCGGTCCA CCTCAGAAACATC (SEQ ID NO. 51) |
| M52-82 | 5-BFLF2-Linker BamHI | TAGGGATCCGGGAGC ATGGCCCCGGTCACC CCAGATG (SEQ ID NO. 52) TAG TCTAGA GGGG |
| M52-83 | 3-BFLF2 XbaI attB2-Flag | ACCACTTTGTACAAGA AAGCTGGGT TCA *CTTGTCGTCATCGTC TTTGTAGTC* CTGTTTATTTTC CAAAATGAG (SEQ ID NO. 53) |
| M52-84 | 5-BGLF4 attB1 | GGGG ACAAGTTTGTAC AAAAAAGCAGGCT ACC ATG GATGTGAATATGGC (SEQ ID NO. 54) |

| Storage number | Designation | Nucleotide sequence |
|---|---|---|
| M52-85 | 3-BFLF2 attB2-Flag | GGGG ACCACTTTGTACA AGAAAGCTGGGT TCA *CTTGTCGTCATCGTCT TTGTAGTCTCCACGTCG* GCCATCTGG (SEQ ID NO. 55) |

Oligonucleotides Used for Sequencing

| Storage number | Designation | Nucleotide sequence |
|---|---|---|
| 6-36 | T7 | TTAATACGACT CACTATAGGG (SEQ ID NO. 56) |
| 10-35 | SP6 | CATTTAGGTGA CACTATAG (SEQ ID NO. 57) |
| 52-92 | 5-pInd20seq_pCMV | CCATCCACGCT GTTTTGACC (SEQ ID NO. 58) |
| M52-86 | 5-BFRF1-BFLF2 Seq. | ACTCGTGGTCG GAATCCG (SEQ ID NO. 59) |
| M52-87 | 3-pInducer20 Sequencing | TTACTAAGCGT AGTCTG (SEQ ID NO. 6) |

Vectors and Expression Plasmids

Eukaryotic Cloning Vectors pcDNA3.1 (+): mammalian expression vector containing a multiple cloning site (MCS) in forward (+) orientation for insertion of an ORF of interest under the control of the HCMV immediate early promoter and enhancer; neomycin and ampicillin resistance cassettes enable the selection of transfected cell clones (Invitrogen, Karlsruhe, Germany).

pDONR221: Donor vector for BP recombination reaction for Gateway Cloning (Invitrogen/Life technologies, Karlsruhe, Germany)

pInducer20 cms (pHM4527): pInducer20 CRS mutagenized (pF1037) for LR recombination reaction for Gateway Cloning (kindly provided by the Stamminger laboratory, Virology, FAU Erlangen-Nürnberg).

| Internal clone number | Designation | Description |
|---|---|---|
| pHM1720 | pcDNA-BGLF4-Flag | eukaryotic expression construct encoding the EBV protein kinase BGLF4, C-terminally fused to the Flag epitope |
| pHM2589 | pcDNA-UL50-HA | eukaiyotic expression construct encoding pUL50, C-terminally fused to the HA epitope |
| pHM2590 | pcDNA-UL53-Flag | eukaiyotic expression construct encoding pUL53, C-terminally fused to the Flag epitope |
| pHM3071 | pcDNA-UL27-HA | eukaiyotic expression construct encoding pUL27, C-terminally fused to the HA epitope |
| pHM4717 | pcDNA-M50-HA | eukaiyotic expression construct encoding pM50, C-terminally fused to the HA epitope |
| pHM4718 | pcDNA-M53-Flag | eukaryotic expression construct encoding pM53, C-terminally fused to the Flag |
| pHM4695 | pcDNA-Orf24-HA | eukaryotic expression construct encoding Orf24, C-terminally fused to the HA epitope |
| pHM4696 | pcDNA-Orf27-Flag | eukaryotic expression construct encoding Orf27, C-terminally fused to the Flag epitope |
| pHM4697 | pcDNA-BFRF1-HA | eukaryotic expression construct encoding BFRF1, C-terminally fused to the HA epitope |
| pHM4698 | pcDNA-BFLF2-Flag | eukaryotic expression construct encoding BFLF2, C-terminally fused to the Flag epitope |
| pF626 | pDsRed1-N1 | mammalian expression vector encoding DsRed1 (variant of *Discosoma* sp. red fluorescent protein) under the control of the HCMV IE promoter/enhancer |
| pF720 | pcDNA-UL97 | eukaryotic expression construct encoding the HCMV protein kinase pUL97 |
| pF721 | pcDNA-UL97-Flag | eukaryotic expression construct encoding the HCMV protein kinase pUL97, C-terminally fused to the Flag epitope |
| pF732 | pcDNA-UL44-Flag | eukaryotic expression construct encoding pUL44, C-terminally fused to the Flag epitope |
| — | Lamin Chromobody-TagGFP plasmid | eukaryotic expression construct encoding the marker of the nuclear envelope Lamin-$V_HH$ fused to green fluorescent protein TagGFP2 (Chromo Tek GmbH, Planegg-Martinsried) |

Newly Generated Plasmids
Domain Swap Constructs

The following expression plasmids encode for the domain swap constructs of HCMV pUL53 and EBV BFLF2. The domain swaps were generated by PCR/PCR amplification of pcDNA-UL53-Flag and pcDNA-BFLF2-Flag using oligonucleotides depicted above. The fragments were inserted into pcDNA3.1 (+) via EcoRI and XhoI.

Domain Swap Constructs Generated

| Internal clone number | Designation | Description | PCR primers | Template |
|---|---|---|---|---|
| pHM4762 | pcDNA-UL53 Hook- UL53 globular domain - Flag | eukaryotic expression construct encoding the hook structure of pUL53 (aa 50-87) and the main globular domain of pUL53 (aa 88-292), C-terminally fused to the Flag epitope | 52-60, 52-61 | pHM2590 |
| pHM4763 | pcDNA-BFLF2 Hook -UL53 globular domain - Flag | eukaryotic expression construct encoding the hook structure of BFLF2 (aa 73-110) and the main globular domain of pUL53 (aa 88-292), C-terminally fused to the Flag epitope | 52-61, 52-62, 52-64 | pHM2590 |
| pHM4764 | pcDNA-UL53 Hook - BFLF2 Hook - UL53 globular domain - Flag | eukaryotic expression construct encoding the N-terminal hook structure of pUL53 (aa 50-71), the C-terminal hook structure of BFLF2 (aa 95-110) and the main globular domain of pUL53 (aa 88-292), C-terminally fused to the Flag epitope | 52-61, 52-64, 52-65 | pHM2590 |

-continued

| Internal clone number | Designation | Description | PCR primers | Template |
|---|---|---|---|---|
| pHM4765 | pcDNA-BFLF2 Hook - UL53 Hook - UL53 globular domain - Flag | eukaryotic expression construct encoding the N-terminal hook structure of BFLF2 (aa 73-94), the C-terminal hook structure of pUL53 (aa 72-87) and the main globular domain of pUL53 (aa 88-292), C-terminally fused to the Flag epitope | 52-61, 52-66 | pHM2590 |
| pHM4766 | pcDNA-BFLF2 Hook - BFLF2 globular domain - Flag | eukaryotic expression construct encoding the hook structure of BFLF2 (aa 73-110) and the main globular domain of BFLF2 (a 111-318), C-terminally fused to the Flag epitope | 52-62, 52-63 | pHM4698 |
| pHM4767 | pcDNA-UL53 Hook - BFLF2 globular domain - Flag | eukaryotic expression construct encoding the hook structure of pUL53 (aa 50-87) and the main globular domain of BFLF2 (aa 111-318), C-terminally fused to the Flag epitope | 52-60, 52-63, 52-67 | pHM4698 |
| pHM4768 | pcDNA-BFLF2 Hook-UL53 Hook-BFLF2 globular domain - Flag | eukaryotic expression construct encoding the N-terminal hook structure of BFLF2 (aa 73-94), the C-terminal hook structure of pUL53 (aa 72-87) and the main globular domain of BFLF2 (aa 111-318), C-terminally fused to the Flag epitope | 52-63, 52-66, 52-67 | pHM4698 |
| pHM4769 | pcDNA-UL53 Hook-BFLF2 Hook-BFLF2 globular domain - Flag | eukaryotic expression construct encoding the N-terminal hook structure of pUL53 (aa 50-71), the C-terminal hook structure of BFLF2 (aa 95-110) and the main globular domain of BFLF2 (aa 111-318), C-terminally fused to the Flag epitope | 52-63, 52-65 | pHM4698 |

Gateway Cloning

The following plasmids encode for BFRF1-BFLF2 and BGLF4 constructed by the Gateway® Technology. The constructs were generated by PCR amplification of BFRF1, BFLF2 and BGLF4 using oligonucleotides listed in Table 2.2. The fusion construct of BFRF1-BFLF2 was initially cloned into pcDNA3.1 (+) via EcoRI, BamHI and XbaI. The fragments of BFRF1-BFLF2 (cutted out from vector via EcoRI and XbaI) and BGLF4 (PCR-product) were firstly inserted into pDONR221 and subsequently into pInducer20 via homologueous recombination.

Gateway Cloning Constructs

| Internal clone number | Designation | Description | PCR primers | Template |
|---|---|---|---|---|
| pM4776sh | pcDNA-BFRF1-BFLF2-Flag | eukaryotic expression construct encoding a fusion of BFRF1 and BFLF2, C-terminally fused to the Flag epitope and with attB1 and attB2-site | M52-80, M52-81 and M52-82, M52-83 | pHM4697 and pHM4698 |
| pM4782sh | pDONR221-BFRF1-BFLF2-Flag | entry clone that contains BFRF1-BFLF2-Flag with attL1 and attL2-site | | pM4776sh |
| pM4783sh | pDONR221-BGLF4-Flag | entry clone that contains BGLF4-Flag with attL1 and attL2-site | M52-84 M52-85 | pHM1720 |

-continued

| Internal clone number | Designation | Description | PCR primers | Template |
|---|---|---|---|---|
| pM4786sh | pInducer-BFRF1-BFLF2-Flag | lentiviral vector construct encoding BFRF1-BFLF2-Flag | | pM4782sh |
| pM4787sh | pInducer-BGLF4-Flag | lentiviral vector construct encoding BGLF4-Flag | | pM4783sh |

Indirect Immunofluorescence Staining and Confocal Laser-Scanning Microscopy

To investigate the impact of distinct herpesviral proteins on the NE, HeLa cells ($3.5 \times 10^5$) were grown on coverslips in 6-well dishes. At two dpt the cells were washed twice with PBSo and fixed with a 4% paraformaldehyde solution for 10 min at RT and subsequently washed three times with PBSo. Permeabilization of the plasma membrane was achieved by incubation with 0.2% Triton X-100 in PBSo at 4° C. for 15 min and subsequently washed again with PBSo five times. For staining of transiently expressed proteins, cells were incubated with the appropriate antibodies diluted in 100 µl PBSo/1% FCS at 37° C. for 60 min. Subsequently, cells were washed three times and incubated with the respective fluorescence-coupled secondary antibodies diluted in PBSo/1% FCS for 30 min at 37° C. Finally, cells were mounted with Vectashield mounting medium with/without DAPI. The cells were analyzed using a TCS SP5 confocal laser-scanning microscope (Leica) and images were processed by LAS AF software (Leica Microsystems) and Photoshop CS5.

Coimmunoprecipitation

CoIP analyses were performed to investigate specific protein-protein interactions (Bannister and Kouzarides, 1996). To this end, 293T cells ($5 \times 10^6$) were transfected with the plasmids coding for the proteins of interest. One day before CoIP, 50 mg/ml protein A sepharose or 25 µl of dynabeads Protein A were incubated with the appropriate antibody in 500 µl CoIP buffer at 4° C. overnight. Two or three dpt cells were harvested. Lysis was performed using 500 µl CoIP buffer containing protease inhibitors and PMSF on ice for 20 min, sonificated (20 impulses, 80%) and centrifuged (14000 rpm, 10 min, 4° C.). For expression controls 50 µl aliquots of each supernatant were taken and boiled in 50 µl 2× boiling mix for 10 min at 95° C. The antibody-loaded dynabeads or sepharose beads (washed three times with CoIP buffer) were incubated with the lysates for 1.5 h at 4° C. Thereafter, samples were washed with CoIP buffer five times, resuspended in 30 µl 2× boiling mix and boiled 10 min at 95° C. Separation and analyzation of protein complexes were performed using SDS-PAGE and Wb.

Western Blot Analysis

Protein samples obtained from CoIP or cell lysates were separated by SDS-PAGE and transferred to a nitrocellulose membrane by electroblotting (200-300 mA for 80 min). The membranes were saturated for at least 1 h with 5% skim milk powder solution to prevent unspecific antibody binding, followed by the binding of the primary antibody diluted in 2.5% skim milk solution at 4° C. overnight. Next day, membranes were washed three times with PBSo/0.1% Tween for 30 min and subsequently incubated with the respective HRP-coupled secondary antibody (in 2.5% skim milk solution) for 1 h at RT. Finally, the membranes were washed again three times with PBSo over 30 min, shortly incubated within a freshly prepared ECL solution (10 ml ECL solution A, 100 µl ECL solution B and 3.1 µl $H_2O_2$) and the proteins were detected by the use of the FUJIFILM Luminescent Image Analyzer LAS-1000 (FUJIFILM Europe GmbH, Düsseldorf, Germany). A prestained molecular weight marker was used to determine the molecular weight and consequently the specification of the protein bands. For further staining of relevant proteins, the membranes were incubated for 20 min at 56° C. in Roti-Free stripping buffer to remove the linked antibodies. After removal of the antibodies, membranes were washed and saturated followed by an additional round of antibody binding.

Generation of Inducible, Stably Expressing Cells

To generate an inducible stably expressing cell line, the Gateway® technology from Invitrogen/Life technologies (Karlsruhe, Germany) was performed according to the manufacturer's protocol to obtain a lentiviral vector with the gene of interest. After successful Gateway cloning lentiviral transduction of HFF cells can be processed.

Combined Results Obtained from Coimmunoprecipitation Analyses (CoIP) Using Proteins from Transient Transfection

| | α-herpesvirus | β-herpesvirus | | γ-herpesvirus |
|---|---|---|---|---|
| | VZV Orf27 | HCMV pUL53 | MCMVpM53 | EBV BFLF2 |
| VZV Orf24 | + | − | − | nd |
| HCMV Pul50 | − | + | + | − |
| MCMV pM50 | nd | + | + | − |
| EBV BFRF1 | nd | − | nd | + |

+ = positive for CoIP interaction;
− = negative for CoIP interaction;
nd = not determined Interaction Analysis of Herpesviral Core NEC Proteins 293T cells were transiently transfected with constructs coding for HA-tagged pUL50, pM50 or pUL27 (negative control) in combination with pUL53 or pM53. At three dpt, cells were lysed and HA-tagged proteins were precipitated using pAb-HA or a rabbit antibody Fc fragment as specificity control. Lysate controls taken prior to the IP and CoIP samples were subjected to standard Wb analysis using tag-specific antibodies as indicated. Similarly, pUL50 or pM50 binding to the EBV-specific core protein BFLF2 was investigated. 293T cells were transiently transfected with constructs coding for HA-tagged pUL50, pM50, pUL44 and BFRF1 or for RFP. Interaction of these proteins with transiently coexpressed Flag-tagged BFLF2, pUL53 or pM53 was investigated by CoIP analysis. At two dpt, cells were lysed and HA-tagged proteins were immunoprecipitated using mAb-HA, mAb-BFRF1 or a mouse antibody Fc fragment as a specificity control. Lysate controls taken prior to the IP and CoIP samples were subjected to standard Wb analysis and protein expression was analyzed using tag- or protein-specific antibodies. Finally, an analysis of Orf27 and pUL50 interaction was performed. Constructs coding for HA-tagged pUL50, Orf24 (positive control) or pUL44 and RFP (negative controls) were transiently cotransfected with Flag-tagged Orf27 in 293T cells. At two dpt, cells were lysed and Orf27 was immunoprecipitated using mAb-Orf27 or a mouse antibody Fc fragment as a specificity control. Lysate controls taken prior to the IP and CoIP samples were examined by standard Wb analysis using the indicated tag-specific and protein-specific antibodies.

Investigation of the Core NEC Formation Using Domain Swap Constructs

It was further analyzed whether the structural elements, mediating the interaction between the two core NEC proteins, of HCMV and EBV are conserved. In order to investigate whether BFLF2 forms a hook structure, which mediates the interaction with BFRF1, we generated several domain swap constructs. These constructs harbor exchanges of the hook structural elements and the N-terminal part of the globular domains according to alignments of a previous study (Milbradt et al., J Biol Chem, 2012). Generation of domain swap constructs was performed using the hook structures and N-terminal part of the globular domains of pUL53 and BFLF2. For the detection of these constructs, a Flag-tag was C-terminally linked. Thereby the hook structure (aa 50-87) or the further N-terminal portion of the globular domain (aa 88-292) of pUL53 was exchanged against the respective predicted sequences of BFLF2 (aa 73-110 or aa 111-318). Furthermore, the hook structure was subdivided into a C-terminal (aa 50-71 of pUL53 or aa 73-94 of BFLF2) and N-terminal (aa 72-87 of pUL53 or aa 95-110 of BFLF2) part and was additionally exchanged in several combinations. In the following sections, the N-terminal part of the hook is abbreviated HN and the C-terminal part HC, whereas the globular domain is termed GLOB. Parts of pUL53 are given in capital letters and BFLF2 in small letters (see FIG. 8).

Conclusion Drawn from the CoIP Findings Obtained with HCMV-EBV Core NEC Domain Swap Constructs Combined, this first series of domain swap constructs did not achieve the desired stability of expressed proteins. For this reason, the CoIP data remained incomplete (e.g. see lack of positive signal in the positive control lane 8 in FIG. 8 panel C) and thus, the drawing of direct conclusions was limited. We obtained a reaction of three of the hook domain swap constructs with HCMV pUL50-HA (containing the HCMV NEC groove), i.e. FIG. 8, panel B, lanes 2, 4 and 7, albeit a clear conclusion about the importance the individual swapped protein fragments could not be drawn. No or only low-level reaction (specificity of the reaction unclear) of the hook domain swap constructs was obtained with EBC BFRF1-HA (containing EBV NEC the groove), i.e. FIG. 8, panel C.

Additional CoIP experiments with other combination of proteins of HCMV, MCMV, EBV and VZV did also not allow a clear conclusion so far about the importance the individual protein domains on homologous or heterologous protein domains at this stage of analysis.

At present, a second series of domain swap constructs has been cloned (containing complete, unmodified N-termini of the hook protein fragments, in order to improve protein stability) and has now been started to be analyzed in a similar manner in CoIP experiments.

Figure 9:
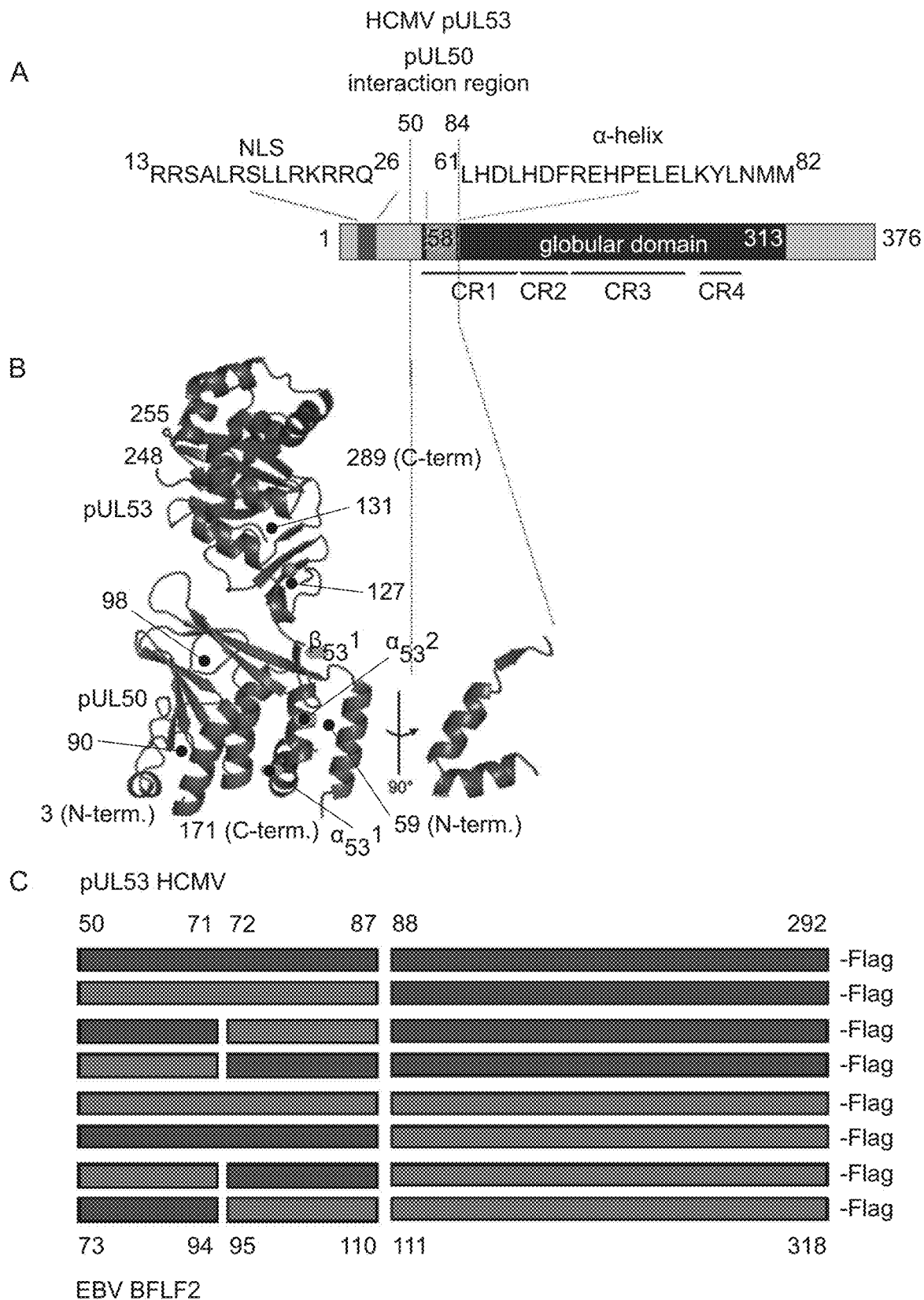

Also, the analysis of the recruitment of the transiently expressed HCMV protein kinase pUL97 by the various herpesviral core NEC proteins did not provide a fully conclusive result (FIG. 9).

Importantly, this kind of experimentation, based on the data shown in FIGS. 7 to 11 and Table 1, led to the preliminary information that a very limited similarity of the viral core NEC proteins is given on the levels of protein biochemistry and CoIP interaction, as compared between HCMV, MCMV, EBV and VZV. One would speculate that no basis is given to find identical NEC protein regions as a putative target for the positioning of putative pan-herpesviral NEC inhibitors. However, this prejudice has been surprising overcome, after taking into account the new crystal structure data.

Crystallization of New NEC Fusion Proteins

The newly identified procedure of cloning two herpesviral NEC fragments into fusion constructs, i.e. fusing a hook region (such as EBV BFLF2 or HCMV pUL53) directly to a groove region (such as EBV BFRF1 or HCMV pUL50), opened strongly improved possibilities of protein crystallization.

The two novel 3D crystal structures of the fusion constructs

EBV BFRF1-BFLF2 and

HCMV pUL50-pUL53 resulted in substantially improved structural information of the core NEC complexes.

Sequences of the Herein Used Polypeptides

```
HCMV pUL50-pUL53 fusion protein for
structural and functional investigations.
In this construct the pUL50 protein
consisting of pUL50 (1-171) is
fused via a GGSGSGGS linker (bold)
to pUL53 (59-292).
                                          SEQ ID NO: 1
MEMNKVLHQDLVQATRRILKLGPSELRVTDA

GLICKNPNYSVCDAMLKTDTVYCVEYLLSYW

ESRTDHVPCFIFKNTGCAVSLCCFVRAPVKL

VSPARHVGEFNVLKVNESLIVTLKDIEEIKP

SAYGVLTKCVVRKSNSASVFNIELIAFGPEN

EGEYENLLRELYAKKAGGSGSGGSLTLHDLH

DIFREHPELELKYLNMMKMAITGKESICLPF

NFHSHRQHTCLDISPYGNEQVSRIACTSCED
```

-continued
NRILPTASDAMVAFINQTSNIMKNRNFYYGF

CKSSELLKLSTNQPPIFQIYYLLHAANHDIV

PFMHAEDGRLHMHVIFENPDVHIPCDCITQM

LTAAREDYSVTLNIVRDHVVISVLCHAVSAS

SVKIDVTILQRKIDEMDIPNDVSESFERYKE

LIQELCQSSG

Truncated HCMV pUL50-pUL53 fusion protein
for structural and functional investigations.
In this construct the pUL50 protein
consisting of pUL50 (1-171) is fused
via a GGSGSGGS linker (bold) to
pUL53 (59-87).
SEQ ID NO: 2

MEMNKVLHQDLVQATRRILKLGPSELRVTDA

GLICKNPNYSVCDAMLKTDTVYCVEYLLSYW

ESRTDHVPCFIFKNTGCAVSLCCFVRAPVKL

VSPARHVGEFNVLKVNESLIVTLKDIEEIKP

SAYGVLTKCVVRKSNSASVFNIELIAFGPEN

EGEYENLLRELYAKKAGGSGSGGSLTLHDLH

DIFREHPELELKYLNMMKMAIT

EBV BMRF1-BMLF2 fusion proteins for
structural and functional investigations.
In this construct EBV BFRF1 consisting
of EBV BFRF1 (Uniprot entry: V5KTU9,
1-MASPEERLLD . . . SDMSQQLS-192)
is fused via a GGSGS linker (bold)
to EBV BFLF2 (Uniprot entry: K9UT32,
78-DRSHFSLRD . . . INYTQLILENKQ-318).
SEQ ID NO: 3

MASPEERLLDELNNVIVSFLCDSGSLEVERC

SGAHVFSRGSSQPLCTVKLRHGQIYHLEFVY

KFLAFKLKNCNYPSSPVFVISNNGLATTLRC

FLHEPSGLRSGQSGPCLGLSTDVDLPKNSII

MLGQDDFIKFKSPLVFPAELDLLKSVVWCRA

YITEHRTTMQFLVFQAANAQKASRVMDMISD

MSQQLSGGSGSDRSHFSLRDFFRGISANFEL

GKDFLREMNTPIHVSEAVFLPLSLCTLSPGR

CLRLSPFGHSLTLGSHCEICINRSQVHVPQE

FSSTQLSFFNNVHKIIPNKTFYVSLLSSSPS

AVKAGLSQPSLLYAYLVTGHFCGTICPIFST

NGKGRLIMHLLLQGTSLHIPETCLKLLCENI

GPTYELAVDLVGDAFCIKVSPRDTVYEKAVN

VDEDAIYEAIKDLECGDELRLQIINYTQLIL

ENKQ

Truncated EBV BMRF1-BMLF2 fusion protein for
structural and functional investigations.
In this construct EBV BFRF1 consisting of
EBV BFRF1 (Uniprot entry: V5KTU9,
1-MASPEERLLD . . . SDMSQQLS-192)
is fused via a GGSGS linker (bold)
to EBV BFLF2(Uniprot entry: K9UT32,
78-DRSHFSLRD . . . -110).
SEQ ID NO: 4

-continued
MASPEERLLDELNNVIVSFLCDSGSLEVERC

SGAHVFSRGSSQPLCTVKLRHGQIYHLEFVY

KFLAFKLKNCNYPSSPVFVISNNGLATTLRC

FLHEPSGLRSGQSGPCLGLSTDVDLPKNSII

MLGQDDFIKFKSPLVFPAELDLLKSMVVCRA

YITEHRTTMQFLVFQAANAQKASRVMDMISD

MSQQLSGGSGSDRSHFSLRDFFRGISANFEL

GKDFLREMNTPIH

VZV ORF24-ORF27 fusion protein for
structural and functional investigations.
In this construct VZV orf24 consisting
of VZV orf24 (Uniprot entry: Q6QCN1,
16-GDNLLQRI . . . TDAYM-189) is fused
via a GGSGSGGS linker (bold) to VZV
orf27 (Uniprot entry: Q6QCM8,
77-SKERSV . . . FDDFVPPR-333).
SEQ ID NO: 5

GDNLLQRIRLVVPSALQCCDGDLPIFDPQRP

PARCVFQFNGEDNVSEAFPVEYIMRLMANWA

QVDCDPYIKIQNTGVSVLFQGFFFRPTNAPV

AEVSIDSNNVILSSTLSTGINLSALESIKRG

GGIDRRPLQALMWVNCFVRMPYVQLSFRFMG

PEDPSRTIKLMARATDAYMGGSGSGGSSKER

SVYRHYFNYIARSPPEELATVRGLIVPIIKT

TPVTLPFNLGQTVADNCLSLSGMGYHLGLGG

YCPTCTASGEPRLCRTDRAALILAYVQQLNN

IYEYRVFLASILALSDRANMQAASAEPLLSS

VLAQPELFFMYHIMREGGMRDIRVLFYRDGD

AGGFMMYVIFPGKSVHLHYRLIDHIQAACRG

YKIVAHVWQTTFLLSVCRNPEQQTETVVPSI

GTSDVYCKMCDLNFDGELLLEYKRLYALFDD

FVPPR

Truncated VZV ORF24-ORF27 fusion protein
for structural and functional investigations.
In this construct VZV orf24 consisting
of VZV orf24 (Uniprot entry: Q6QCN1,
16-GDNLLQRI . . . TDAYM-189) is fused via
a GGSGSGGS linker (bold) to VZV orf27
(Uniprot entry: Q6QCM8,
77-SKERSV . . . RGLIVPII 109).
SEQ ID NO: 6

GDNLLQRIRLVVPSALQCCDGDLPIFDPQRP

PARCVFQFNGEDNVSEAFPVEYIMRLMANWA

QVDCDPYIKIQNTGVSVLFQGFFFRPTNAPV

AEVSIDSNNVILSSTLSTGINLSALESIKRG

GGIDRRPLQALMWVNCFVRMPYVQLSFRFMG

PEDPSRTIKLMARATDAYMGGSGSGGSSKER

SVYRHYFNYIARSPPEELATVRGLIVPII

SEQ ID NO: 7

LTLHDLHDIFREHPELELKYLNMMKMAIT

Amino acid sequence of the HCMV pUL53 N-terminal hook structure (strain AD169; accession number P16794). From said primary structure or from homologues thereof, the secondary, tertiary and quaternary-structures of the disclosed N-terminal hook structure are derived (see FIGS. 1 and 2).

SEQ ID NO: 8

MSSVSGVRTPRERRSALRSLLRKRRQRELAS

KVASTVNGATSANNHGEPPSPADARPRLTLH

DLHDIFREHPELELKYLNMMKMAITGKESIC

LPFNFHSHRQHTCLDISPYGNEQVSRIACTS

CEDNRILPTASDAMVAFINQTSNIMKNRNFY

YGFCKSSELLKLSTNQPPIFQIYYLLHAANH

DIVPFMHAEDGRLHMHVIFENPDVHIPCDCI

TQMLTAAREDYSVTLNIVRDHVVISVLCHAV

SASSVKIDVTILQRKIDEMDIPNDVSESFER

YKELIQELCQSSGNNLYEEATSSYAIRSPLT

ASPLHVVSTNGCGPSSSSQSTPPHLHPPSQA

TQPHHYSHHQSQSQQHHHRPQSPPPPLFLNS

IRAP

Amino acid sequence of the HCMV pUL53 protein shown as primary-structure (strain AD169; accession number P16794). Within the SEQ ID NO: 8 the primary-structure of the N-terminal hook structure, disclosed by the invention (see FIGS. 1 and 2), is highlighted in bold.

SEQ ID NO: 9

MEMNKVLHQDLVQATRRILKLGPSELRVTDA

GLICKNPNYSVCDAMLKTDTVYCVEYLLSYW

ESRTDHVPCFIFKNTGCAVSLCCFVRAPVKL

VSPARHVGEFNVLKVNESLIVTLKDIEEIKP

SAYGVLTKCVVRKSNSASVFNIELIAFGPEN

EGEYENLLRELYAKKAASTSLAVRNHVTVSS

HSGSGPSLWRARMSAALTRTAGKRSSRTASP

PPPPRHPSCSPTMVAAGGAAAGPRPPPPPMA

AGSWRLCRCEACMGRCGCASEGDADEEEEEL

LALAGEGKAAAAAGQDVGGSARRPLEEHVS

RRRGVSTHHRHPPSPPCAPSLERTGYRWAPS

SWWRARSGPSRPQSGPWLPARFATLGPLVLA

LLLVLALLWRGHGQSSSPTRSAHRD

Amino acid sequence of the HCMV pul50 protein shown as primary structure (strain AD169; accession number P16794).

Homologues of HCMV pUL53 protein

SEQ ID NO: 10

MYDTDPHRRGSRPGPYHGKERRRSRSSAAGG

TLGVVRRASRKSLPPHARKQELCLHERQRYR

GLFAALAQTPSEEIAIVRSLSVPLVKTTPVS

LPFCLDQTVADNCLTLSGMGYYLGIGGCCPA

CNAGDGRFAATSREALILAFVQQINTIFEHR

AFLASLVVLADRHNAPLQDLLAGILGQPELF

FVHTILRGGGACDPRLLFYPDPTYGGHMLYV

IFPGTSAHLHYRLIDRMLTACPGYRFVAHVW

QSTFVLVVRRNAEKPTDAEIPTVSAADIYCK

MRDISFDGGLMLEYQRLYATFDEFPPP

Amino acid sequence of UL31 of HSV-1 strain 17 (P10215). Within the SEQ ID NO: 10 the homologous primary structure of the N-terminal hook structure, disclosed by the invention (see FIGS. 1 and 2), is highlighted in bold.

SEQ ID NO: 11

MYDIAPRRSGSRPGPGRDKTRRRSRFSAAGN

PGVERRASRKSLPSHARRLELCLHERRRYRG

FFAALAQTPSEEIAIVRSLSVPLVKTTPVSL

PFSLDQTVADNCLTLSGMGYYLGIGGCCPAC

SAGDGRLATVSREALILAFVQQINTIFEHRT

FLASLVVLADRHSTPLQDLLADTLGQPELFF

VHTILRGGGACDPRLFYPDPTYGGHMLYVI

FPGTSAHLHYRLIDRMLTACPGYRFAAHVWQ

STFVLVVRRNAEKPADAEIPTVSAADIYCKM

RDISFDGGLMLEYQRLYATFDEFPPP

Amino acid sequence of UL31 of HSV-2 strain HG52 (P89454). Within the SEQ ID NO: 11 the homologous primary structure of the N-terminal hook structure, disclosed by the invention (see FIGS. 1 and 2), is highlighted in bold.

SEQ ID NO: 12

MHLKPTRFFHANQPPMPHSYEMEDLCFDDMQ

YRWSPSNTPYRSMSRRYKSVSRSGPSMRVRS

RTPCRRQTIRGKLMSKERSVYRHYFNYIARS

PPEELATVRGLIVPIIKTTPVTLPFNLGQTV

ADNCLSLSGMGYHLGLGGYCPTCTASGEPRL

CRTDRAALILAYVQQLNNIYEYRVFLASILA

LSDRANMQAASAEPLLSSVLAQPELFFMYHI

MREGGMRDIRVLFYRDGAGGFMMYVIFPGK

SVHLHYRLIDHIQAACRGYKIVAHVWQTTFL

LSVCRNPEQQTETVVPSIGTSDVYCKMCDLN

FDGELLLEYKRLYALFDDFVPPR
Amino acid sequence of ORF27 of VZV strain Dumas (P09283). Within the SEQ ID NO: 12 the homologous primary structure of the N-terminal hook structure, disclosed by the invention (see FIGS. 1 and 2), is highlighted in bold.

SEQ ID NO: 13

MTVHKSRIRRSRSLSVTHRIQKRPDHREKTK

LYLQLKLHDLHTVFNLFPEYEQKFLAII

KLPITGKEPIDVPFSLSNHHQHTCLEFSPYA

NEQISKSACLHCESVSVPTSSDAMVAHLNQV

NNVMQNRLYFYGFRKDMELIRMSAKQPTIFQ

IFYIVHNTINNIFPIMFERKQKLGMHIVFQS

RTLHIPCEC1KQIVAVSSGYNVYLDILQESV

ILTVLCETLDTNTNIHIDIGMLQKKLEEMDI

PNEISDRLEKYKGHLIGFH
Amino acid sequence of U37 of HHV-6A strain Uganda-1102 (P28865). Within the SEQ ID NO: 13 the homologous primary structure of the N-terminal hook structure, disclosed by the invention (see FIGS. 1 and 2), is highlighted in bold.

SEP ID NO: 14

MTVHKNRFRRSRSLSVTHRIQKRPDHREKTK

LYLQLKLHDLHAVFNLFPEYEQKFLAIIKLP

ITGKEPIDVPFSLSNHHQHTCLEFSPYANEQ

ISKSACLHCESVSVPTSSDAMVAHLNQVTNV

MQNRFYFYGFRKDMELIRMSAKQPTIFQIFY

IVHNTINNIFPIMFEKKQKLGMHIVFQSRTL

HIPCECIKQIIAVSSGYNVYLDILQDSVILT

VLCETLDTNTNIHIDIGMLQKKLEEMDIPNE

ISDRLEKYKGHLIGFH
Amino acid sequence of UL37 of HHV-6B strain HST (Q9WT27). Within the SEQ ID NO: 14 the homologous primary structure of the N-terminal hook structure, disclosed by the invention (see FIGS. 1 and 2), is highlighted in bold.

SEQ ID NO: 15

MAIQSTRRLRRASSLLKKSKPYNKEKTNLSL

SLSLKELHSVFKLFPEYELKFLNMMKLPITG

KEPIKIPFDLSLHHQHTCLDLSPYANEQVSK

SACVNCGTTNIPTASDAMVAYMNQISNVMQN

RLYYYGFQKKVELIRMSAKQPTLFQIFYILS

SIASNFPLPIMFENNEKLNMYVVFQTRTLHIP

CECINQIMTVSSGYTVLLDILHDSIVLHVLC

KTIETSNIQIDINVLQRKIEEMDVPDEIGDK

FEKLKHILPFI
Amino acid sequence of UL37 of HHV-7 strain JI (P52361). Within the SEQ ID NO: 15 the homologous primary structure of the N-terminal hook structure, disclosed by the invention (see FIGS. 1 and 2), is highlighted in bold.

SEQ ID NO: 16

MAPVTPDAVNARQQRPADPALRRLMHPHHRN

YTASKASAHSVKSVSRCGKSRSELGRMERVG

SVARSICSRHTRHGVDRSHFSLRDFFRGISA

NFELGKDFLREMNTPIHVSEAVFLPLSLCTL

SPGRCLRLSPFGHSLTLGSHCEICINRSQVH

VPQEFSSTQLSFFNNVHKIIPNKTFYVSLLS

SSPSAVKAGLSQPSLLYAYLVTGHFCGTICP

IFSTNGKGRLIMHLLLQGTSLHIPETCLKLL

CENIGPTYELAVDLVGDAFCIKVSPRDTVYE

KAVNVDEDAIYEAIKDLECGDELRLQIINYT

QLILENKQ
Amino acid sequence of BFLF2 of EBV strain P95-8 (PoCK47). Within he SEQ ID NO: 16 the homologous primary structure of the N-terminal hook structure, disclosed by the invention (see FIGS. 1 and 2), is highlighted in bold.

SEQ ID NO: 17

MPKSVSSHISLATSTGRSGPRDIRRCLSSRL

RSVPPGARSASVSSKHRNGLRKFISDKVFFS

ILSHRHELGVDFLREMETPICTSKTVMLPLD

LSTVAPGRCVSLSPFGHSSNMGFQCALCPST

ENPTVAQGSRPQTMVGDALKKNNELCSVALA

FYHHADKVIQHKTFYLSLLSHSMDVVRQSFL

QPGLLYANLVLKTFGHDPLPIFTTNNGMLTM

CILFKTRALHLGETALRLLMDNLPNYKISAD

CCRQSYVVKFVPTHPDTASIAVQVHTICEAV

AALDCTDEMRDDIQKGTALVNAL
Amino acid sequence of ORF67 of HHV-8 strain GK18 (F5H982). Within the SEQ ID NO: 17 the homologous primary structure of the N-terminal hook structure, disclosed by the invention (see FIGS. 1 and 2), is highlighted in bold.

SEQ ID NO: 18

MFERRRLLRRKSSAARRKTLTRAARDRYAPY

FAYAAAQPSDEVTTVRGLSNPLIKTAPVTLP

FDLGQAVADNCLSLSGMGYYLGLGGCCPTCA

-continued

AAEPRLGRSDRAALVLAYVQQLNSIYEYRVF

LASVAARDPSERALEEVLAHPELFFAYYVLR

DGGLRDVRVLFFEDPDAQGALMMYVVFPEKS

VHVHHRVLDRLLGACAGHRIVAHVWQTMFVL

VVRKKGDGRPADDVPAVSASDIYCKMRDISF

DGELLLEYKRLYAAFEDFRPPRP
Amino acid sequence of UL34 of
PrV strain Kaplan (Q911V7).
Within the SEQ ID NO: 18 the
homologous primary structure
of the N-terminal hook structure,
disclosed by the invention
(see FIGS. 1 and 2),
is highlighted in bold.

SEQ ID NO: 19

MFRSPEGEERDAADREEEEGGEARRRSRMMM

SPRRVKRARHRPAGSGLRTPLRSPSACRC

SSPSPERQWQQRRRAEKRSTTPTDPPPPKR

SAASAAAGAAAPESEYLNVKLSELHDVFQ

RHPDLEQKYLKIMKLPITGKESIRLPFDFKS

HRQHTCLDLSPYGNDQVSRSACTTCKETT

RLPTASDSMVAFINQTSNVMKHRKFYFGFRK

NMELLKMAANQPQLFQIYYIVQSCVQEIVPL

IYYDREMAHMQLIFEKETVHIPSQCIEQILT

VAKDAYGVSLDIAHQRITLTARCLRLESSSL

RIDVLMLQRKVDELEIPNETNEKFESYSL
Amino acid sequence of pM53 of
MCMV (H2A291). Within the
SEQ ID NO: 19 the homologous
primary structure of the
N-terminal hook structure,
disclosed by the invention
(see FIGS. 1 and 2), is
highlighted in bold.

HOMOLOGUES OF HCMV PUL50 PROTEIN

SEQ ID NO: 20

MAGLGKPYTGHPGDAFEGLVQRIRLIVPSTL

RGGDGEAGPYSPSSLPSRCAFQFHGHDGSDE

SFPIEYVLRLMNDWAEVPCNPYLRIQNTGVS

VLFQGFFHRPHNAPGGAITPERTNVILGSTE

TTGLSLGDLDTIKGRLGLDARPMMASMWISC

FVRMPRVQLAFRFMGPEDAGRTRRILCRAA

EQAITRRRRTRRSREAYGAEAGLGVAGTGFR

ARGDGFGPLPLLTQGPSRPWHQALRGLKHL

RIGPPALVLAAGLVLGAAIWWWGAGARL
Amino acid sequence of UL34
of HSV-1 strain 17 (p10218).

SEQ ID NO: 21

MAGMGKPYGGRPGDAFEGLVQRIRLIVPATL

RGGGGESGPYSPSNPPSRCAFQFHGQDGSD

EAFPIEYVLRLMNDWADVPCNPYLRVQNTGV

SVLFQGFFNRPHGAPGGAITAEQTNVILHS

TETTGLSLGDLDDVKGRLGLDARPMMASMWI

SCFVRMPRVQLAFRFMGPEDAVRTRRILC

RAAEQALARRRRSRRSQDDYGAVWAAAHHSS

GAPGPGVAASGPPAPPGRGPARPWHQAV

QLFRAPRPGPPALLLLAAGLFLGAAIWWAVG

ARL
Amino acid sequence of UL34
of HSV-2 strain HG52 (P89457).

SEQ ID NO: 22

MSRRTYVRSERRRGCGDNLLQRIRLWPSALQ

CCDGDLPIFDPQRPPARCVFQFNGEDNVSEA

FPVEYIMRLMANWAQVDCDPYIKIQNTGVSV

LFQGFFFRPTNAPVAEVSIDSNNVILSSTLS

TGINLSALESIKRGGGIDRRPLQALMWVNCF

VRMPYVQLSFRFMGPEDPSRTIKLMARATD

AYMYKETGNNLDEYIRWRPSFRSPPENGSPN

TSVQMQSDIKPALPDTQTTRVWKLALPVAN

VTYALFIVIVLVWLGAVLFWK
Amino acid sequence of ORF24
of VZV strain Dumas (P09280).

SEQ ID NO: 23

MANVLKEKMYDELLSATCRILKLGSHDYRIT

ERNLLSKNPKFPLCDIILKLDYAYNLEYLLS

LWEHVTKQEPRFVFKNTGGAVSMSCYLHAPV

KVEGHHAVRECNILRVNECLTVRMSDIVAM

KPSTFAVFTKCIIRRNRDDTYWEFVAFGPEN

ESEYISLLKAIFLKKCSMGKQHLESNRFCQG

LRRRSSHVLEKGRFESSGKWNKASAWTSQES

IKQFYEKEKSLLSGVKFWRLSERHCRFAL

VGICFLLALYFCYVLLKKTPTPASGSVV
Amino acid sequence of U34 of
HHV-6A strain Uganda-1102
(P52465).

SEQ ID NO: 24

MANVLKEKMYDELLSATCRILKLGSHDYRMT

ERNLLSKNPKFPLCDIILKLDYAYNLEYLLS

LWEHVTKQEPRFVFKNTGGAVSMSCYLHAPV

KAEGHHAVRECNILRVNECLTVRMSDIVA

MKPSTFAVFTKCIIRRNRDETYWEFVAFGPE

NESEYISLLKAIFLKKCSMGKQHLESNRFCQ

```
GLRRRSSHVLEKGQLGSSGEIANKASAVVTS

QESINQFYEKEKSFLSGVKFSRLSERHCRVA

IVSICFLLALYFCYVLLKKTPTPASGPVV
Amino acid sequence of U34
of HHV-6B strain Z29 (Q9QJ35).

SEQ ID NO: 25

MLKEKMYDELILSTCRVLKLGPADFRVTDKN

LFSKNPKFPLCDILLKLDFAYSLEYLLSLWE

DLTKQEARFIFKNTGGAVSMSCYLHAPIKQE

SQNIVKECNILNVNECLSVCLNDIEAIKPSS

SGVLTKCIIRRNRDAAFIVEFVAFGPESESE

YIALLKAIILKKKFLERQDLEKHRAARHIKK

PLRLQLKSVGEMTSFRSINYMGNTKDAAVFP

VTVPIFARRNNILCGFLVAALLIVCYVIFKE

FALSADFSAV
Amino acid sequence of U34
of HHV-7 strain JI (P52466).

SEQ ID NO: 26

MASPEERLLDELNNVIVSFLCDSGSLEVERC

SGAHVFSRGSSQPLCTVKLRHGQIYHLEFVY

KFLAFKLKNCNYPSSPVFVISNNGLATTLRC

FLHEPSGLRSGQSGPCLGLSTDVDLPKNSII

MLGQDDFIKFKSPLVFPAELDLLKSMWCRAY

ITEHRTTMQFLVFQAANAQKASRVMDMISDM

SQQLSRSGQVEDTGARVTGGGGPRPGVTHS

GCLGDSHVRGRGGWDLDNFSEAETEDEASYA

PWRDKDSWSESEAAPWKKELVRHPIRRHRTR

ETRRMRGSHSRVEHVPPETRETVVGGAW

RYSWRATPYLARVLAVTAVALLLMFLRWT
Amino acid sequence of BFRF1
of EBV strain B95-8 (P03185).

SEQ ID NO: 27

MSVVGKRWDELCRVVSSYLGQSGQSLDLERC

IDGAPVYAKGGATAICTVRMQHGCVYHLE

FVYKFWAHLLEEMHYPFSPCFVISNNGLSTT

LKCFLCRPSDAVSQFGHVLPVESDVYLAKNT

SVVLGQDDFTKFKASLVFSKNLGVYNSMVIC

RTYFTDYRQVLQFLVVTPKSHKRLKSLLETV

YCLAAPVADSAAQGGAGFPTNGRDARACTSD

VTAVYWAGQGGRTVRILGAFQWSLGRAVAL

VRRSWPWISAGIAFLCLGLVWMRPS
Amino acid sequence of ORF67
of HHV-8 strain GK18 (Q76RF3).

SEQ ID NO: 28

MSGTLVQRLKLILSGGNLRCSDGETACDPER

PPTRCVFQVHGQDGSNDTFPLEYVLRLMRS

WAHVPCDPYVRVQNTGVSVLFQGFFFRPADA

PLAAITAEHNNVILASTHSTGMSLSALDDIK

RAGGVDTRPLRAMMSVSCFVRMPRVQLSFRF

MGPDDASQTQRLLDRAEMRQRSVSRPGGGA

GGGDDGEGPSPRAPIRPTVISPVPGHAAAA

FVGQAAYPPPARFPASLLHTLLGLRRLAGY

AVACVTGALAIVIILNMR
Amino acid sequence of UL34
of PrV strain Kaplan (Q9ICS7).

SEQ ID NO: 29

MEIDKNVGADLISNTRRILRLDENELRITDTA

LICKNPNYSLCDAMLTTDIVYPVEYLLSYWE

CRSGRTACFVFKNTGCRVSLSCYIGFPERLK

DLKRVCDFNFLSVNEALVVTLADIERIKPCD

KGVLTNCVVRKSNSGMSYNIEVVAFGPDNEA

EYQALLRDIYARRMTSVPTDCGSLICRRARC

LAAAPPRRPPPPPPPGQRWGSLRKHGPVLTR

RYAGGGGAAKNQPAAASPTSTSTSSPAAPSR

DQDQTQRPPPAGDTNVTAAETTYSERTISFL

TRHANAIHCALILAAAIALVLLWLLYWHAAR

SAGHP
Amino acid sequence of pM50
of MCMV (H2A365).

Homologues of HCMV pUL53 sequences
for the N-terminal hook structure
of the peptide target of the invention

SEQ ID NO: 30

RYRGLFAALAQTP3EEIAIVRSLSVPLV
Predicted amino acid sequence of HSV-1
UL31 N-terminal hook structure based
on homology to the HCMV pUL53
sequence SEQ ID NO: 7.

SEQ ID NO: 31

RYRGFFAALAQTPSEEIAIVRSLSVPLV
Predicted amino acid sequence of HSV-2
UL31 N-terminal hook structure based
on homology to the HCMV pUL53 sequence
SEQ ID NO: 7.

SEP ID NO: 32

VYRHYFNYIARSPPEELATVRGLIVPII
Predicted amino acid sequence of
VZV ORF27 N-terminal hook
structure based on homology to the
HCMV pUL53 sequence SEQ ID NO: 7.

SEP ID NO: 33

KLHDLHTVFNLFPPEYEQKFLAIIKLPIT
Predicted amino acid sequence of
HHV-6A U37 N-terminal hook
structure based on homology
to the HCMV pUL53 sequence
SEQ ID NO: 7.

SEQ ID NO: 34

KLHDLHAVFNLFPPEYEQKFLAIIKLPIT
Predicted amino acid sequence of
HHV-6B U37 N-terminal hook
structure based on homology
to the HCMV pUL53 sequence
SEQ ID NO: 7.
```

-continued

SEQ ID NO: 35
SLKELHSVFKLFPEYELKFLNMMKLPIT
Predicted amino acid sequence
of HHV-7 U37 N-terminal hook
structure based on homology
to the HCMV pUL53 sequence
SEQ ID NO: 7.

SEP ID NO: 36
SLRDFFRGISANFELGKDFLREMNTPIH
Predicted amino acid sequence
of EBV BFLF2 N-terminal hook
structure based on homology
to the HCMV pUL53 sequence
SEQ ID NO: 7.

SEQ ID NO: 37
SDKVFFSILSHRHELGVDFLREMETPIC
Predicted amino acid sequence
of HHV-8 ORF67 N-terminal hook
structure based on homology to
the HCMV pUL53 sequence
SEQ ID NO: 7.

SEP ID NO: 38
RYAPYFAYAAAQPSDEVTTVRGLSNPLI
Predicted amino acid sequence of
PrV UL34 N-terminal hook
structure based on homology to
the HCMV pUL53 sequence
SEQ ID NO: 7.

SEQ ID NO: 39
KLSELHDVFQRHPDLEQKYLKIMKLPIT
Predicted amino acid sequence of
MCMV pM53 N-terminal hook
structure based homologuey to the
HCMV pUL53 sequence SEQ ID NO: 7.

Bioinformatics Analyses for the Patent Application

The crystal structures of the HCMV pUL50-pUL53, EBV BFRF1-BFLF2, and VZV orf24-orf27 complexes, which are part of this patent application, revealed a high structural similarity of the hook-into-groove interaction despite a low level of sequence similarity. This raises the question whether the residues present at equivalent sequence positions in the different herpesviral hook proteins play similar roles in the respective groove interactions of the core NECs of the three herpesviruses. For that purpose, bioinformatics was used to calculate the energetic contributions (ΔΔG values in FIG. 13) of the individual amino acid side chains in the respective herpesviral hook proteins for the interaction. Energetic analyses were done using the program Fold-X (46). FIG. 13 shows that the energy profile is highly conserved between the hook proteins from different herpesviruses indicating the presence of common hot-spots of the interaction that can be exploited for ligand design.

The similarity in the energy profiles of the hook proteins (FIG. 13) suggests that the design of a common hook sequence ("shared hook") that fits into the grooves of different herpesviral proteins should be feasible. Therefore, a computational workflow was established that allows the design of such shared hooks. For the development of the methods, the HCMV pUL50-pUL53, EBV BFRF1-BFLF2 complexes, which are part of this patent application, were used as model systems. The basic idea of the approach is to replace each residue in each hook by one of the existing 20 amino acid types and to measure the interaction energy with the corresponding autologous or non-autologous groove proteins. For the sequence of the shared hook those amino acid types are suggested that fit both into the grooves of HCMV pUL50 and EBV BFRF1.

The results for this approach are explained in more detail using sequence position 59 of HCMV pUL53 as an example (FIG. 14). The respective residue in HCMV pUL53 is a leucine, and the structurally equivalent residue in EBV BFLF2 is a phenylalanine. The computational scan (Table 1) shows that a phenylalanine is both tolerated in HCMV pUL53 and EBV BFLF2 (−0.65 kcal/mol and 0.00 kcal change in binding energy, respectively, compared to the wild-type hook sequences). For the C-terminally adjacent sequence position (threonine in HCMV and serine in EBV; FIG. 14), a tyrosine represents a good compromise amino acid for a shared hook. It does not affect the interaction in EBV (0.00 kcal/mol) and leads only to a moderately reduced affinity (0.88 kcal/mol) for HCMV. Application of this approach to all sequence positions of the hook results in the shared hook sequence shown in FIG. 14. However, there exist multiple shared hook sequences, which exhibit similar energies requiring further investigation. Therefore, in the final step of the workflow, molecular modeling is used to generate structure predictions of the shared hook in complex with different groove proteins (FIG. 15) and to investigate the binding properties by molecular dynamics simulations. This type of analysis allows assessing the conformational stability of the complex and a more accurate calculation of the interaction energies.

TABLE 1

Computational amino acid scans for the design of a shared hook that fits into the grooves of HCMV pUL50 and EBV BFRF1. The first column shows the position of the hook (HCMV numbering). The second column gives the preferential amino acid type that fits both into the grooves of HCMV and EBV. Changes in interaction energy (kcal/mol) compared to the respective wildtype residue are given in columns 3 and 4. Negative values denote an increase in affinity upon mutation.

| Position | AA | HCMV | EBV |
|---|---|---|---|
| 59 | PHE | −0.65 | 0.00 |
| 60 | TYR | 0.88 | 0.00 |
| 61 | LEU | 0.00 | 0.00 |
| 62 | TRP | −1.32 | −0.30 |
| 63 | SER | 0.07 | −0.02 |
| 64 | MET | 0.05 | 0.04 |
| 65 | PHE | 0.43 | 0.00 |
| 66 | ILE | 0.92 | −0.25 |
| 67 | ALA | 2.15 | 2.09 |
| 68 | ILE | 0.34 | 4.30 |
| 69 | MET | −0.02 | −0.37 |
| 70 | ARG | −0.11 | −0.21 |
| 71 | TYR | −2.20 | −0.22 |
| 72 | PHE | 0.28 | 0.05 |
| 73 | GLU | 0.00 | 0.00 |
| 74 | LEU | −0.02 | 0.00 |
| 75 | GLY | 1.86 | 0.00 |
| 76 | MET | −0.01, | −0.03 |
| 77 | LYS | 0.00 | −0.99 |
| 78 | TYR | 0.00 | −1.00 |
| 79 | LEU | 0.08 | 0.00 |
| 80 | ASN | 0.00 | −0.16 |
| 81 | MET | 0.00 | −1.93 |
| 82 | MET | 0.00 | 0.00 |
| 83 | MET | −0.05 | −0.66 |
| 84 | LYS | −0.69 | −0.96 |
| 85 | PRO | −1.23 | 0.00 |
| 86 | MET | −0.33 | 0.26 |
| 87 | ILE | 0.33 | −0.01 |
| 88 | GLY | 0.00 | 0.00 |

The computational analyses above focused on the properties of the hooks and exploited them for the design of a shared hook as prototype of an inhibitory peptide.

In alternative embodiments of the present invention, the grooves of different herpesviral NEC proteins could be targeted by small organic compounds. In order to allow binding to multiple different groove proteins, such organic compounds should target conserved sites of the groove. These conserved sites were identified from an analysis of the evolutionary conservation of the surface region among different herpesviral groove proteins. The results from this analysis are shown in FIG. 16. The next step of the computational prediction method according to embodiments of the present invention comprises the identification of those conserved residues that are located sufficiently close in space to be targeted by the same small organic compound. In some embodiments of the present invention relating to computational analysis methods of the present invention, based on the degree of conservation and the presence of functional side chain groups, E56/Y57 are subject to these methods, because they represent a promising docking site for small organic ligands to interfere with the pUL53 interaction (FIG. 17). In addition, or alternatively, a larger ligand that may contact the highly conserved hydrophobic residues L162/L163 can increase binding affinity, so that these residues may be subject to the computational analysis methods of the present invention, too.

Co-Immunoprecipitation Analysis with Hook Peptide pUL53 in Three Different Buffers million 293T cells were grown in a 10 cm-dish, and harvested 3 days post transfection with 5 μg/construct. The cells were subjected to a lysis in respective buffer (1×10 cm dish in 500 μL). In parallel reactions, beads (DynaBeads Protein A (ThermoFisher) were incubated with pAb-HA and rotated for 30 minutes at ambient temperature and then washed three times with a standard co-immunoprecipitation washing buffer. For immunoprecipitation experiments, UL50-HA (150 μl or 50 μl) or RFP were added to beads and then filled up to 500 μl with buffer and rotated for 1 hour at ambient temperature before a further washing step of the beads was performed. For the peptide incubation peptide (5 or 25 μM) in 350 or 450 μl buffer were added and rotated for 1 hour at ambient temperature. For coimmunoprecipitation UL53-Flag (150 or 50 μl) or pcDNA3.1 were added to bead-peptide-mix and rotated for 1 hour at ambient temperature. Subsequently, the beads were washed five times and then mixed with 30 μl 2× Boiling-Mix for 10 min 95° C.

Structure Determination of VZV QRF24-ORF27 Fusion Protein

VZV ORF24-ORF27 fusion protein for structural and functional investigations comprises VZV orf24 consisting of VZV orf24 (Uniprot entry: Q6QCN1, 16-GDNLLQRI . . . TDAYM-189) fused via a GGSGSGGS linker to VZV orf27 (Uniprot entry: Q6QCM8, 77-SKERSV . . . FDDFVPPR-333) and is depicted in SEQ ID NO:5.

Protein Crystallization of VZV ORF24-ORF27 Fusion Protein

The fusion protein consisting of VZV ORF24-ORF27 (SEQ ID NO:5) was screened for crystallization conditions using the sitting drop technique and proteins with concentrations between 10 and 15 mg/ml dissolved in a buffer consisting of 50 mM TrisHCl buffer, 50 mM NaCl, pH 8.0 and 5 mM DTT). Diffraction quality crystals of VZV ORF24-ORF27 fusion protein (SEQ ID NO: 5) were obtained at 20° C. with 0.09 M Bis-Tris pH 5.5, 0.91 M(NH4)2SO4, 2.72% PEG 3350, 3.64% formamid as a reservoir solution. Crystallization droplets were set up while mixing 2 μl protein and 1 μl reservoir solution. Crystals grew within five to ten days to sizes of 300×20×10 μm³. The crystals were flash-frozen in liquid nitrogen upon addition of 20% ethylene glycol to a protein droplet.

Crystal Structure Determination

A 2.4 resolution diffraction data set was collected at beamline P13 at DESY synchrotron in Hamburg from crystals of VZV ORF24-ORF27 (SEQ ID NO: 5). Data were processed with program XDS. Initial phases were obtained with the molecular replacement technique with program PHENIX_PHASER using the structure of the HSV-1 nuclear egress complex as a search model (PDB entry code 4ZXS.pdb). The structure was completed and corrected using either the PHENIX program AUTOBUILD or manually using program COOT. Crystallographic data collection and refinement statistics are summarized in Table 2.

TABLE 2

| Data collection and refinement statistics | |
|---|---|
| VZV ORF24-ORF27 fusion protein. Data collection | DESY 2.12.2018, Beamline P13 (LL__cgt3) |
| Resolution range (Å) | 19.68-2.4 (2.46-2.4) |
| Space group | P21 |
| Unit cell dimensions | 76.135.2 157.8 90 93.91 90 |
| Multiplicity | 15.8 |
| Unique reflections | 33224 |
| Completeness (%) | 98.8 (95.9) |
| Wilson B-factor | 61.3 |
| Rmeas (%) | 16.7 (163.4) |
| Mean I/σI | 9.97 (0.72) |
| Reflections used in | 33100 |

Figure 18A:
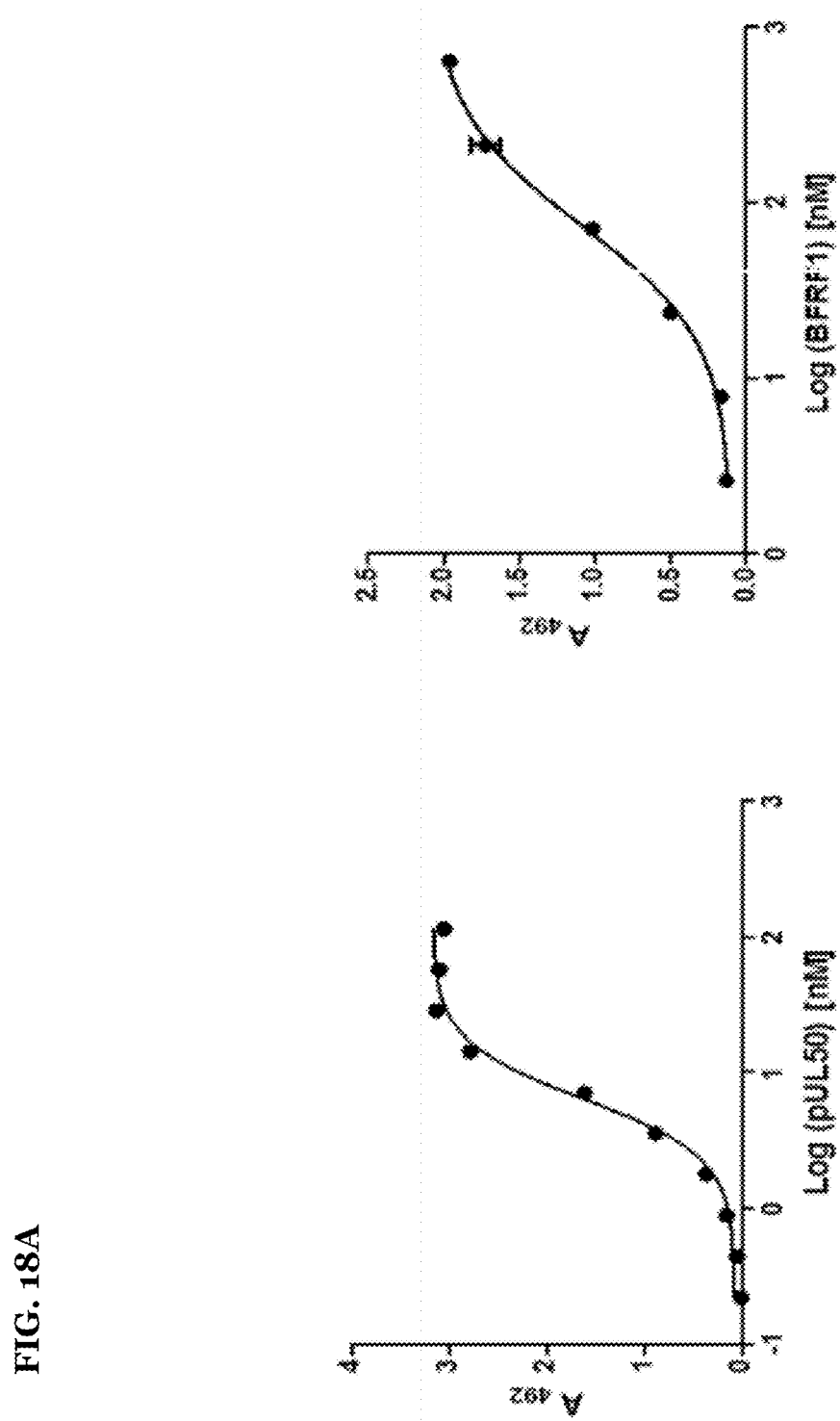
Figure 18B:
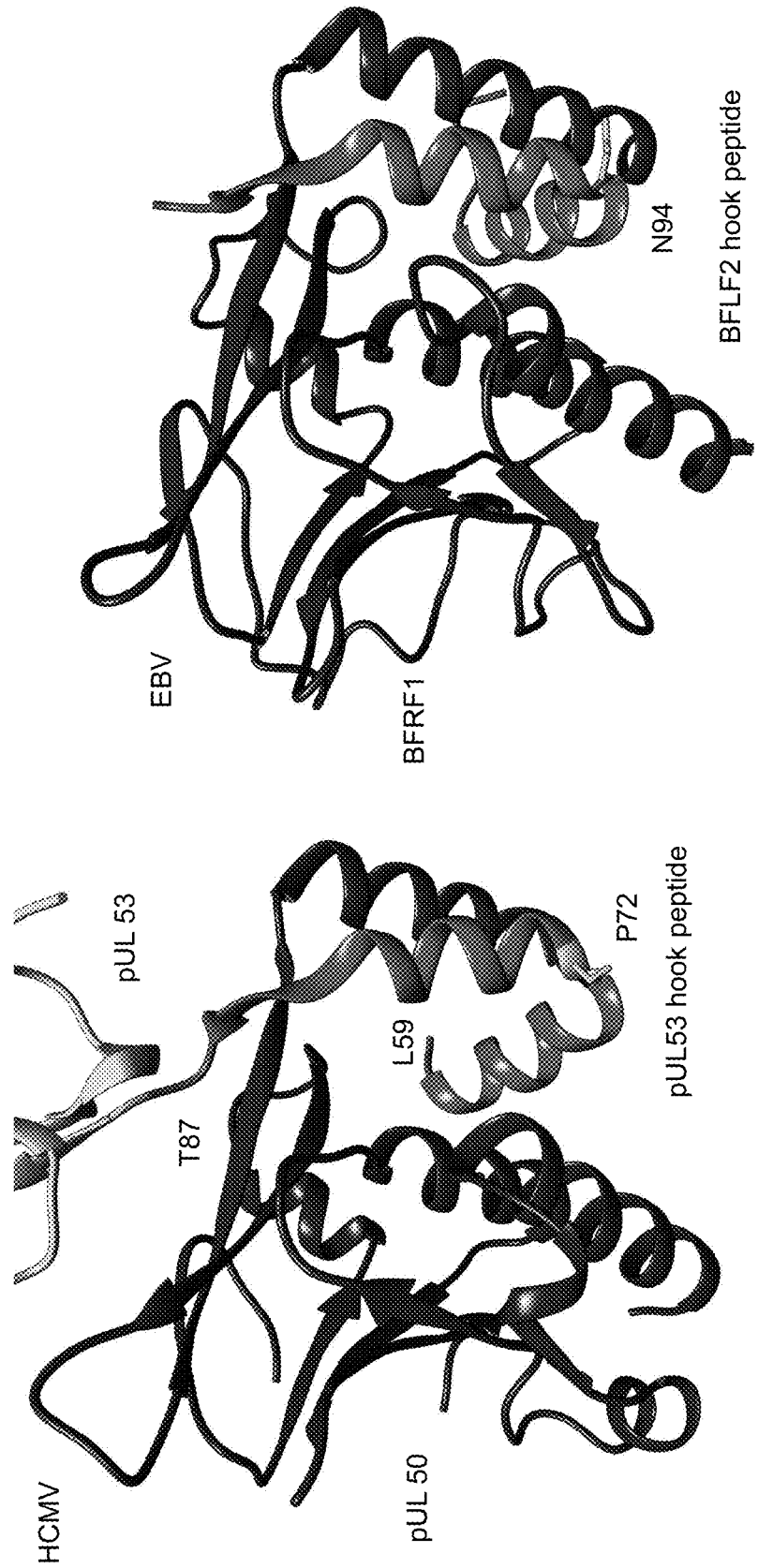

Interaction and Cross-Reactivity of HCMV and EBV NEC Proteins and Derived Peptides The hook-groove protein interactions of the HCMV and EBV NECs was analyzed at the level of soluble recombinant proteins, using a direct ELISA type binding assay, in which the hook protein was coated to microtiter plates, and the His-tagged groove proteins added at different concentration. For NEC protein complexes, dose-dependent binding of the respective proteins could be shown, however, the pUL50-pUL53 interaction of HCMV is approximately 20-fold stronger (EC50=6.2 nM) (FIG. 18A, left) than the BFRF1-BFLF2 interaction of EBV (EC50=122 nM) (FIG. 18A, right)

These protein interactions then served as the basis for competitive assays, in which the HCMV and EBV hook proteins (pUL53 and BFLF2), as well as peptides that present the helical hook regions of these proteins (FIG. 18B, Table 3), were tested for their ability to inhibit the pUL50-pUL53 and BFRF1-BFLF2 interactions, respectively. These experiments were designed to address the peptide-protein interactions for each virus, as well as the ability of the hook peptides and proteins to cross-interact with the groove proteins of the respective other virus.

Figure 18C:
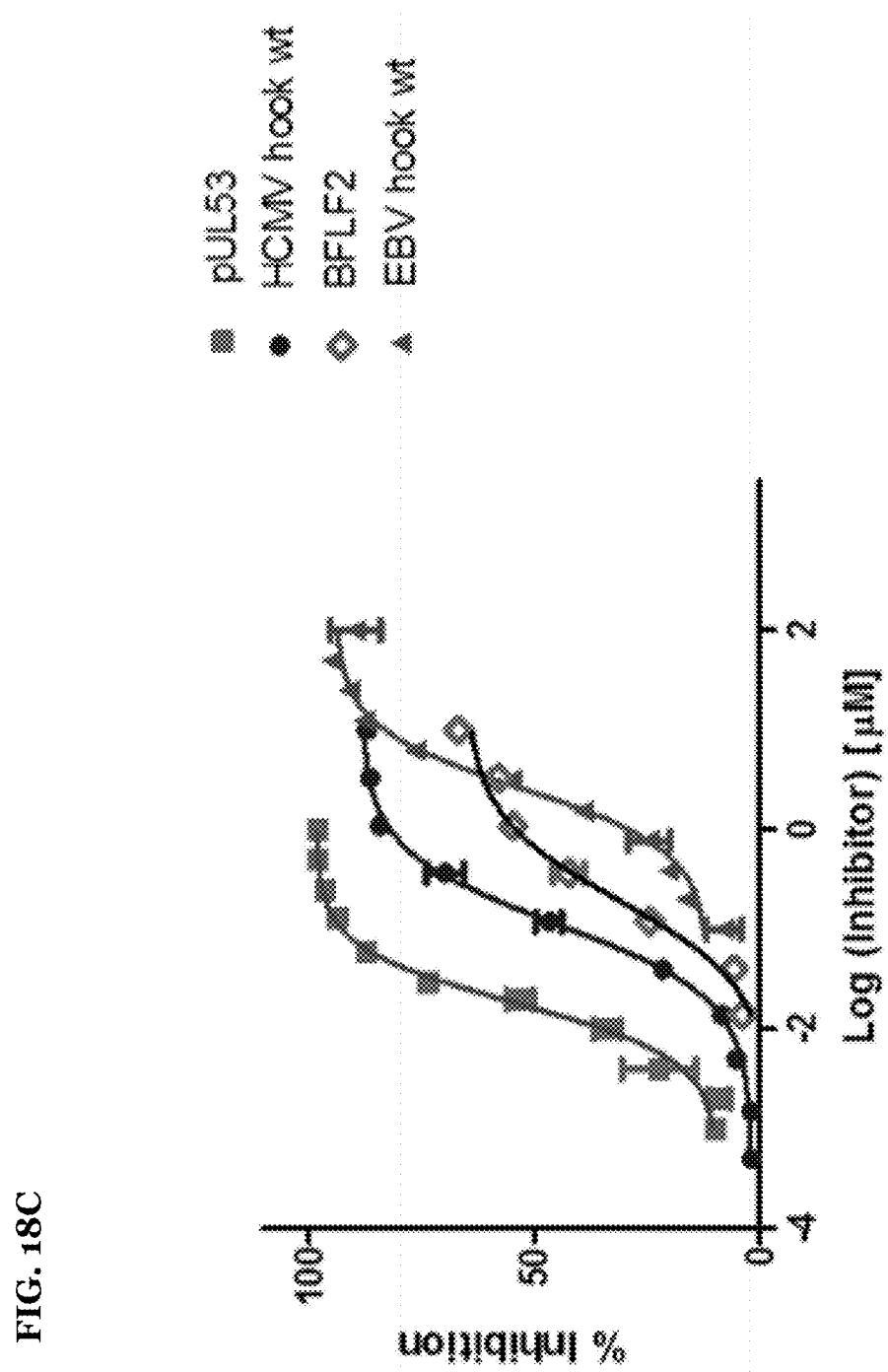

Interestingly, both hook peptides and proteins were able to interfere with the pUL50-pUL53 interaction (HCMV NEC), albeit to a varying extent (FIG. 18C). While the HCMV hook protein (pUL53) was the strongest inhibitor of that interaction (IC50=18 nM), the EBV hook protein BFLF2 had an approximately 11-fold lower activity (IC50=198 nM). This result is in agreement with the inhibitory activities of the peptides presenting the hook regions of both hook proteins, which is approximately 22-fold lower for the EBV hook peptide (IC50=2.6 μM) than for the HCMV hook peptide (IC50=114 nM).

Apart from indicating a moderate cross-reactivity of the HCMV and EBV NEC proteins, these data also demonstrate the utility of the HCMV pUL53 and EBV BFLF2 hook peptides to serve as starting points in the search for Herpesvirus NEC inhibitors as a novel antiviral strategy.

Methods in Peptide Biochemistry

Peptide Synthesis

Peptides (see Table 3 for sequences) were synthesized as C-terminal amides by Fmoc/t-Bu-based solid-phase synthesis, (Groβ et al, DOI: 10.1002/cbic.201402545). Biotin was introduced by coupling of Fmoc-Lys (biotin). Crude peptides were purified by preparative HPLC, and purified peptides were then characterized by analytical HPLC with online ESI mass spectrometry detection (LC-MS). Stock solutions of purified peptides were prepared at 5 mM in 50% acetonitrile/water.

TABLE 3

Sequences of HCMV and EBV hook peptides

| | Peptide Sequence |
|---|---|
| HCMV hook peptide | Ac[a]-59LTLHDLHDIFREHPELE LKYLNMMKMAIT87-Aoa[b]-Lys(Bio[c])-NH2 |
| EBV hook peptide | Ac-80SHFSLRDFFRGISANFEL GKDFLREMNTP108-Aoa-Lys(Bio)-NH2 |

[a]Ac, acetyl; [b]Aoa, 8-amino-3,6-dioxaoctanoic acid; [c]Bio, biotin.

Direct Binding Assay

High binding Immulon microtiter plates were coated overnight at 4° C. with the HCMV (pUL53) and EBV (BFLF2) hook proteins, respectively, (2 μg/mL in 0.1 M sodium carbonate buffer pH 9.5, 100 μL/well). Unspecific binding was blocked with 1% BSA in 0.1 M phosphate buffer pH 7.2 (200 μL/well, one hour). Plates were then incubated with 100 μL/well of His-tagged groove protein solution (pUL50 and BFRF1, respectively) at serial dilutions, starting from 2.5 μg/mL and 15 μg/mL, respectively, for one hour. Bound protein was detected using 100 μL/well anti-His-HRP conjugate from Sigma at a 1:10.000 dilution. All proteins and antibodies were in 0.1 M phosphate buffer pH 7.2, containing 0.1% BSA and 0.01% Tween20. Plates were washed four times with 0.01% Tween 20 in 0.1 M phosphate buffer pH 7.2 (300 μL/well) after each incubation step. Plates were developed with 100 μL/well OPD (1 mg/mL) in the presence of 0.03% $H_2O_2$ for approximately 10 minutes in the dark. After the reaction was stopped with 50 μL/well 2M H2SO4, absorbance was read at 492 nm. All data points present means of duplicates.

Competitive Binding Assay

High binding Immulon microtiter plates were coated with pUL53 and BFLF2, respectively, as described above for the direct binding assay. After blocking with BSA plates were incubated with 50 μL/well of inhibitor solutions at different concentration ranges, and 50 μL/well of His-tagged pUL50 (0.16 μg/mL) and BFRF1 (5 μg/mL), respectively. His-tagged pUL50 and BFRF1 were detected and plates developed as described above. IC50-values were determined using the regression wizard of GraphPad Prism. All data points present means of duplicates. Inhibition was calculated according to the following formula:

% Inhibition=[1−(Apeptide−Ablank1)/(A100%−Ablank2)]×100, in which "100%" is a sample without inhibitor, "blank1" is a sample without coated hook protein and "blank2" is a sample without coated hook protein and without inhibitor.

REFERENCES CITED HEREIN

Throughout the description portion, the numbers in brackets referring to cited literature, denote the following references:

1. Griffiths. P., et al.; J. Pathol. 235, 288-297
2. Mocarski, E. S., Jr., Shenk, T., Griffiths, P. D., and Pass, R. F. (2013) Cytomegaloviruses. Fields Virology, 6th Ed. (eds. Knipe, D. M., and Howley, P.M.), Lippincott Williams & Wilkins, 1960-2014
3. Hamilton, S. T., (2014) et al.; Rev. Med-Virol. 24, 420-433
4. Marschall, M., and Stamminger, T. (2009); Future Microbiol. 4, 731-742
5. Lee, C. P., and Chen, M. R. (2010); Rev. Med. Virol. 20, 214-230
6. Marschall, M., Feichtinger, S., and Milbradt, J. (2011); Adv. Virus Res. 80, 69-101
7. Tandon, R., and Mocarski, E. S. (2012); Trends Microbiol. 20, 392-401
8. Mettenleiter, T. C., Müller, F., Granzow, H., and Klupp, B. G. (2013); Cell. Microbiol. 15, 170-178
9. Leigh, K. E., et al.; (2015), Proc. Natl. Acad. Sci. USA 112, 9010-9015
10. Muranyi, W., et al.; (2002), Science 297, 854-857
11. Hamirally, S., et al.; PLOS Pathog. 5, e1000275 (2009)
12. Milbradt, J., Auerochs, S., Sticht, H., and Marschall, M. (2009); J. Gen. Virol. 90, 579-590
13. Milbradt, J., et al.; (2010) J. Biol. Chem. 285, 13979-13989
14. Milbradt, J., et al.; J. Biol. Chem. 287, 24004-24016
15. Milbradt, J., et al.; (2014), Mol. Cell. Proteomics 13, 2132-2146
16. Marschall, M., et al.; (2005), J. Biol. Chem. 280, 33357-33367
17. Kuny, C. V., et al.; (2010); PLOS Pathog. 6, e1001092
18. Lemnitzer, F., et al.; (2013); Cell. Microbiol. 15, 335-351
19. Schmeiser, C., (2013), J. Gen. Virol. 94, 2056-2069
20. Studier, F. W., et al.; (1990), Methods Enzymol. 185, 60-89
21. Laskowski, R. A., et al.; (1993), J. Appl. Cryst. 26, 283-291
22. Kabsch, W. (2010) Xds. Acta Crystallogr. D. Biol. Crystallogr. 66, 125-132
23. Pape, T., and Schneider, T. R. (2004), J. Appl. Cryst. 37, 843-844
24. Sheldrick, G. M. (2010), Acta Crystallogr. D. Biol. Crystallogr. 66, 479-485
25. Schneider, T. R., and Sheldrick, G. M. (2002), D. Biol. Crystallogr. 58, 1772-1779
26. Adams, P. D., et al.; et al.; (2010); Acta Crystallogr. D. Biol. Crystallogr. 66, 213-221
27. Emsley, P., et al., (2010); Acta Crystallogr. D. Biol. Crystallogr. 66, 486-501
28. Winn, M. D., et al., (2011); D. Biol. Crystallogr. 67, 235-242
29. Schrödinger, L. L. C. (2010) et al.; J. Gen. Virol. 88, 2642-2650.
31. Funk, C., et al.; PLOS Pathog. 11, e1004957 (2015)
32. Harding, M. M. (2004) et al.; Acta Crystallogr. D. Biol. Crystallogr. 60, 849-859
33. Thompson, J. D., Higgins, D. G., and Gibson, T. J. (1994); Nucleic Acids Res. 22, 4673-4680
34. Lötzerich, M., et al.; Nucleic Acids Res. 43, D345-356
36. Krissinel, E., and Henrick, K. (2004); Acta Crystallogr. D. Biol. Crystallogr. 60, 2256-2268
37. Dutta, R., and Inouye, M. (2000); Trends Biochem. Sci. 25, 24-28
38. Sam, M. D., et al.; J. Virol. 83, 2996-3006
39. Gres, A. T., et al.; Science 349, 99-103 (2015)
40. Ruiz, F. M., et al.; PLOS One 10, e0129691 (2015)
41. Bigalke, J. M., et al.; Nat. Commun. 5:4131, 1-12
42. Sharma, M., and Coen, D. M. (2014); J. Virol. 88, 10982-10985
43. Sharma, M., et al.; J. Virol. 89, 523-34
44. Milbradt, J., et al.; Mol. Cell. Proteomics 13, 2132-2146
45. Walzer, Sascha, A., et al.; The Journal of Biological Chemistry, Vol. 290, No. 46, 27452-27458 (2015)
46. Schymkowitz et al., 2005, Nucleic Acids Res. 33: W382-8

The invention claimed is:

1. A polypeptide comprising at least two fused domains, wherein
   a) a first domain comprises a polypeptide comprising amino acid residues 1 to 171 according to SEQ ID NO: 1 or according to SEQ ID NO: 2, or a homologue thereof, and wherein a second domain comprises a polypeptide comprising amino acid residues 180 to 413 according to SEQ ID NO: 1 or amino acid residues 180 to 208 according to SEQ ID NO: 2, or a homologue thereof;
   or
   b) a first domain comprises a polypeptide comprising amino acid residues 1 to 192 according to SEQ ID NO: 3 or according to SEQ ID NO: 4, or a homologue thereof, and wherein a second domain comprises a polypeptide comprising amino acid residues 198 to 438 according to SEQ ID NO: 3 or amino acid residues 198 to 230 according to SEQ ID NO: 4, or a homologue thereof;
   or
   c) a first domain comprises a polypeptide comprising amino acid residues 1 to 174 according to SEQ ID NO: 5 or according to SEQ ID NO: 6, or a homologue thereof, and wherein a second domain comprises a polypeptide comprising amino acid residues 183 to 439 according to SEQ ID NO: 5 or amino acid residues 183 to 215 according to SEQ ID NO: 6, or a homologue thereof.

2. The polypeptide according to claim 1, wherein in a), b) and c) at least one additional amino acid sequence is inserted between the first and second domains, or between respective homologues thereof.

3. The polypeptide according to claim 1, wherein a) is selected and wherein in a) the first domain comprising amino acid residues 1 to 171 according to SEQ ID NO: 1 or according to SEQ ID NO: 2, or a homologue thereof corresponds to, or is part of, human cytomegalovirus protein pUL50 or a homologue thereof, and wherein the second domain comprising amino acid residues 180 to 413 according to SEQ ID NO: 1 or amino acid residues 180 to 208 according to SEQ ID NO: 2 corresponds to, or is part of, human cytomegalovirus protein pUL53 or a homologue thereof.

4. The polypeptide according to claim 1, wherein b) is selected and wherein in b) the first domain comprising amino acid residues 1 to 192 according to SEQ ID NO: 3 or according to SEQ ID NO: 4 corresponds to, or is part of, Epstein-Barr virus protein BFRF1 or a homologue thereof, and wherein the second domain comprising amino acid residues 198 to 438 according to SEQ ID NO: 3 or amino acid residues 198 to 230 according to SEQ ID NO: 4 corresponds to, or is part of, Epstein-Barr virus protein BFLF2 or a homologue thereof.

5. The polypeptide according to claim 1, wherein c) is selected and wherein in c) the first domain comprising amino acid residues 1 to 174 according to SEQ ID NO: 5 or according to SEQ ID NO: 6 corresponds to, or is part of, Varizella Zoster Virus protein VZV ORF24 or a homologue thereof, and wherein the second domain comprising amino acid residues 183 to 439 according to SEQ ID NO: 5 or amino acid residues 183 to 215 according to SEQ ID NO: 6 corresponds to, or is part of, Varizella Zoster Virus protein VZV ORF27 or a homologue thereof.

6. The polypeptide according to claim 1 comprising in a) the amino acid sequence according to SEQ ID NO: 1 or 2 or a homologue thereof.

7. The polypeptide according to claim 1, comprising in b) the amino acid sequence according to SEQ ID NO: 3 or 4 or a homologue thereof.

8. The polypeptide according to claim 1 comprising in c) the amino acid sequence according to SEQ ID NO: 5 or 6 or a homologue thereof.

9. A method for screening, which is achieved by the polypeptide as defined in claim 1.

10. An antibody or antibody fragment or IgG scaffold or non-IgG scaffold specifically binding the polypeptide of claim 1 or a homologue thereof.

11. A method for screening agents that specifically bind to and/or interact with and/or antagonize the polypeptides as defined in claim 1, comprising the steps of:
   a) providing a reaction system in vitro,
   b) providing at least one polypeptide as defined in a), b) or c) of claim 1, or a homologue thereof as polypeptide target,
   c) mixing at least one candidate agent,
      wherein either said polypeptide target or said candidate agent or both said polypeptide target and said candidate agent are optionally labelled with a detectable label selected from a group comprising a radioisotope, a chemiluminescent label, a fluorescent label, a bioluminescent label, a peptide, or an enzyme, and
d) detecting binding and/or interaction and/or antagonization between said polypeptide target and said candidate agent by monitoring functional and structural changes in at least one polypeptide according to any one of SEQ ID NOs: 1 to 6 or a homologue thereof and/or in the candidate agent binding to and/or interacting with and/or antagonization of said polypeptide target or a homologue thereof,
wherein functional and/or structural changes in the at least one polypeptide target or a homologue thereof and/or increased binding and/or interaction and/or antagonization between said at least one polypeptide target and said candidate agent relative to the control without said candidate agent is indicative of activity of the candidate agent in affecting and/or conformationally influencing said at least one polypeptide target or homologue thereof.

12. The method of claim 11, wherein said method is an immunoprecipitation assay, a microscopy-based assay, a peptide binding assay, an NMR-based assay, an X-ray assay, an in silico assay, an inhibition assay, an immunoassay, and/or a cellular assay.

13. An in silico method of structural screening agents that specifically bind to and/or interact with and/or antagonize the polypeptides as defined in claim 1, comprising the steps of:
a) providing crystal structure data of at least one polypeptide as defined in any one of a), b) or c) of claim 1, or a homologue thereof, as polypeptide target, and
b) calculating whether at least one candidate agent of known structure specifically binds to and/or interacts with and/or antagonizes the polypeptide target or a homologue thereof.

14. A method of computer-assisted identification of a compound that modulates an activity of a target protein, the method comprising:
a) providing a crystal structure of at least one target polypeptide as defined in claim 1, or a homologue thereof, in complex with a biomolecule, or a fragment thereof,
b) performing a long timescale molecular dynamics simulation of the structure,
c) identifying one or more evolved three dimensional topological features on the target polypeptide of the structure of step (a), and
d) identifying a compound that binds to at least one of the one or more evolved three dimensional topological features identified in step (c), wherein binding of the compound to the one or more evolved three dimensional topological features modulates an activity of the target protein.

15. A method of computer-assisted identification of a compound that modulates an interaction between a target polypeptide and a biomolecule, wherein the biomolecule is a binding partner of the target polypeptide, the method comprising:
a) providing a crystal structure of at least one target polypeptide as defined in claim 1, or a homologue thereof, in complex with a biomolecule, or a fragment thereof,
b) performing a long timescale molecular dynamics simulation of the structure,
c) identifying one or more evolved three dimensional topological features on the target polypeptide of the structure of step (a), and
d) identifying a compound that binds to at least one of the one or more evolved three dimensional topological features identified in step (c) wherein binding of the compound to the one or more evolved three dimensional topological features modulates an interaction between the target polypeptide and the biomolecule or fragment thereof.

16. An in vitro method of identifying biologically active agents that reduce virus replication in cells, wherein said virus is a herpesvirus selected from the group of Herpesviridae, said method comprising:
a) combining a biologically active candidate agent selected from the group comprising polypeptides, proteins, protein fragments, antibodies, antibody fragments, IgG scaffolds, non-IgG scaffolds, peptides, peptide fragments, nucleic acids, ribonucleic acids, RNAi, small molecules, in silico designed small molecules, further characterised in that said biologically active candidate agent is binding to and/or interacting with and/or antagonizing a target polypeptide as defined in claim 1 or a respective homologue thereof, with at least one cell that is infected with said virus, and
b) determining the effect of said biologically active candidate agent on virus replication.

17. The method of claim 11, wherein said candidate agent is selected from the group comprising polypeptides, proteins, protein fragments, antibodies, antibody fragments, IgG scaffolds, non-IgG scaffolds, peptides, peptide fragments, nucleic acids, ribonucleic acids, RNAi, small molecules and in silico designed small molecules.

18. The method of claim 11, further comprising varying the amount of candidate agent in said reaction system.

19. The method of claim 16, wherein said herpesvirus is Epstein-Barr Virus or Varizella Zoster Virus or human cytomegalovirus.

20. The method of claim 1, wherein said homologue thereof is a functional homologue which encodes nuclear egress complex (NEC) polypeptides or NEC-derived polypeptides that are capable of heterodimerization to form a heterodimer that is at least 50% as stable as said polypeptides as defined in any one of a), b) or c) of claim 1 under identical assay conditions.

21. The method of claim 1, wherein two subunits of the fusion proteins are linked by a glycine-rich amino acid sequence comprising 3 to 12 amino acids.

* * * * *